US008252749B2

(12) United States Patent
Steinberg et al.

(10) Patent No.: US 8,252,749 B2
(45) Date of Patent: Aug. 28, 2012

(54) METHODS, KITS, AND COMPOSITIONS FOR GENERATING NEW HAIR FOLLICLES AND GROWING HAIR

(75) Inventors: David Steinberg, Milton, MA (US);
Kevin Pojasek, Cambridge, MA (US);
Stephen Prouty, Doylestown, PA (US);
George Cotsarelis, Berwyn, PA (US);
Mayumi Ito, Philadelphia, PA (US)

(73) Assignees: Follica, Inc., Waltham, MA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/443,122

(22) PCT Filed: Sep. 27, 2007

(86) PCT No.: PCT/US2007/020842
§ 371 (c)(1),
(2), (4) Date: Jan. 26, 2010

(87) PCT Pub. No.: WO2008/042216
PCT Pub. Date: Apr. 10, 2008

(65) Prior Publication Data
US 2010/0120768 A1 May 13, 2010

Related U.S. Application Data

(60) Provisional application No. 60/847,854, filed on Sep. 28, 2006.

(51) Int. Cl.
*A61K 38/00* (2006.01)
(52) U.S. Cl. .................................. 514/20.7; 514/9.6
(58) Field of Classification Search .................. None
See application file for complete search history.

(56) References Cited

U.S. PATENT DOCUMENTS

| 4,490,365 | A | 12/1984 | Panaretto et al. |
| 5,124,354 | A | 6/1992 | Green |
| 5,457,105 | A | 10/1995 | Barker |
| 5,486,509 | A | 1/1996 | Jimenez et al. |
| 5,747,498 | A | 5/1998 | Schnur et al. |
| 5,752,949 | A | 5/1998 | Tankovich et al. |
| 5,772,990 | A | 6/1998 | Hocquaux et al. |
| 5,972,929 | A | 10/1999 | Kobayashi et al. |
| 6,113,926 | A | 9/2000 | Soler et al. |
| 6,121,269 | A | 9/2000 | Henry et al. |
| 6,283,956 | B1 | 9/2001 | McDaniel |
| 6,491,904 | B1 | 12/2002 | Lee et al. |
| 6,492,395 | B1 | 12/2002 | Scheiwe et al. |
| 6,629,971 | B2 | 10/2003 | McDaniel |
| 6,720,427 | B2 | 4/2004 | Sanner et al. |
| 6,764,493 | B1 | 7/2004 | Weber et al. |
| 6,831,186 | B2 | 12/2004 | Bauman et al. |
| 6,884,427 | B1 | 4/2005 | Barrows |
| 6,936,044 | B2 | 8/2005 | McDaniel |
| 7,198,641 | B2 | 4/2007 | Barrows |
| 2002/0065314 | A1 | 5/2002 | Nielsen et al. |
| 2002/0114772 | A1 | 8/2002 | Morgan et al. |
| 2002/0132792 | A1 | 9/2002 | Prien et al. |
| 2003/0219464 | A1 | 11/2003 | Incando et al. |
| 2004/0127470 | A1 | 7/2004 | Masferrer |
| 2004/0153131 | A1 | 8/2004 | Yorke |
| 2004/0242612 | A1 | 12/2004 | Moussy et al. |
| 2005/0214344 | A1 | 9/2005 | Barrows et al. |
| 2006/0062770 | A1 | 3/2006 | Zheng et al. |
| 2006/0105006 | A1 | 5/2006 | Jarrousse et al. |
| 2007/0092496 | A1 | 4/2007 | Zheng et al. |
| 2007/0122387 | A1 | 5/2007 | Cochran et al. |
| 2007/0148138 | A1 | 6/2007 | Barrows et al. |

FOREIGN PATENT DOCUMENTS

| EP | 0236014 | 7/1991 |
| EP | 0648488 | 11/2000 |
| JP | 2003 081866 A | 3/2003 |
| WO | WO 00/31134 | 6/2000 |
| WO | WO 01/74164 | 10/2001 |
| WO | 02060396 | 8/2002 |
| WO | WO 02/092771 | 11/2002 |
| WO | WO 2005/017107 | 2/2005 |
| WO | 2005091891 | 10/2005 |
| WO | 2006105109 | 6/2006 |
| WO | WO 2006105109 A2 * | 10/2006 |

OTHER PUBLICATIONS http://www.mesotheliomaweb.org/mesothelioma/treatment/egfr accessed on Sep. 22, 2011.*
Du Cros et al., "Fibroblast Growth Factor and Epidermal Growth Factor in Hair Development" J Invest Dermatol 101:106S-113S 1993.
Jahoda and Reynolds, "Dermal-Epidermal Interactions. Adult Follicle-Derived Cell Populations and Hair Growth" Dermalogic Clinics:573-583 1996.
Kwak et al., "Irreversible Inhibitors of the EGF Receptor May Circumvent Acquired Resistance to Gefitinib" Proc Natl Acad Sci USA 102:7665-7670 2005.
Lo Celso et al., "Transient Activation of Beta-Catenin Signaling in Adult Mouse Epidermis is Sufficient to Induce New Hair Follicles but Continuous Activation is Required to Maintain Hair Follicle Tumours" Development 131:1787-1799 2004.
Powell et al., "Growth Inhibition of Psoriatic Keratinocytes by Quinazoline Tyrosine Kinase Inhibitors" Br J Dermatol 141:802-810 1999.
Takada et al., "Hepatic Transport of Pki166, an Epidermal Growth Factor Receptor Kinase Inhibitor of the Pyrrolo-Pyrimidine Class, and its Main Metabolite, ACU154" Drug Metab Dispos. 32:1272-1278 2004.
Wood et al., "A Unique Structure for Epidermal Growth Factor Receptor Bound to GW572016 (Lapatinib): Relationships Among Protein Conformation, Inhibitor Off-Rate, aAnd Receptor Activity in Tumor Cells" Cancer Res 64:6652-6659 2004.
International Search Report Mailed on Aug. 8, 2008 for PCT/US07/20842.
Argyris, "Kinetics of Epidermal Production during Epidermal Regeneration Following Abrasion in Mice," *Am. J. Pathol.* 83(2): 329-340, 1976.

(Continued)

*Primary Examiner* — Anand Desai
*Assistant Examiner* — Melissa Mercier
(74) *Attorney, Agent, or Firm* — Clark & Elbing LLP

(57) ABSTRACT

The invention features methods, kits, and compositions for generating new hair follicles and growing hair on a subject.

17 Claims, 43 Drawing Sheets

OTHER PUBLICATIONS

Ley and Applegate, "Hair Growth Induction by Ultraviolet Radiation in the Marsupial *Monodelphis domestica*," *Arch. Dermatol.* 123(8): 1032-1035, 1987.

Li et al., "Early Epidermal Destruction with Subsequent Epidermal Hyperplasia is a Unique Feature of the Papilloma-Independent Squamous Cell Carcinoma Phenotype in PKCepsilon Overexpressing Transgenic Mice," *Toxicol. Pathol.* 33(6): 684-694, 2005.

Van Mater et al., "Transient Activation of β-Catenin Signaling in Cutaneous Keratinocytes is Sufficient to Trigger the Active Growth Phase of the Hair Cycle in Mice," *Genes Dev.* 17(10): 1219-1224, 2003.

Office Action from U.S. Appl. No. 11/887,104, dated May 6, 2010.

Supplementary European Search Report for EP07838926.9 dated Apr. 27, 2011.

Botchkarev and Fessing, "Edar signaling in the control of hair follicle development" *J. Investig. Dermatol. Symp. Proc.*, 10(3):247-51 (2005).

Fuchs and Segre, "Stem cells: a new lease on life" *Cell*, 100(1):143-55 (2000).

Huelsken et al., "β-Catenin controls hair follicle morphogenesis and stem cell differentiation in the skin" *Cell*, 105(4):533-45 (2001).

Millar, "Molecular mechanisms regulating hair follicle development" *J. Invest. Dermatol.*, 118(2):216-25 (2002).

Moore et al., "Epidermal hyperplasia and wool follicle regression in sheep infused with epidermal growth factor" *J. Invest. Dermatol.*, 84(3):172-5 (1985).

Botchkarev et al., "Noggin is a Mesenchymally Derived Stimulator of Hair-Follicle Induction," *Nat. Cell. Biol.* 1:158-164 (1999).

Botchkarev et al., "Noggin is Required for Induction of the Hair Follicle Growth Phase in Postnatal Skin," *FASEB J.* 15:2205-2214 (2001).

Danilenko et al., "Keratinocyte Growth Factor is an Important Endogenous Mediator of Hair Follicle Growth, Development, and Differentiation: Normalization of the Nu/Nu Follicular Differentiation Defect and Amelioration of Chemotherapy-Induced Alopecia," *Am. J. Pathol.* 147:145-154 (1995).

Hallmans et al., "Regeneration of Hair Follicles from Experimental Wounds of the Rabbit Ear," *Scand. J. Plast. Reconstr. Surg.* 8:207-210 (1974).

Han et al., "Effect of Minoxidil on Proliferation and Apoptosis in Dermal Papilla Cells of Human Hair Follicle," *J. Dermatol. Sci.* 34:91-98 (2004).

Hotta, "Effect of T-Flavanone on Hair Growth," *Fragrance Journal* 31:33-40 (2003) (English Language Abstract).

Jahoda et al., "Cellular and Extracellular Involvement in the Regeneration of the Rat Lower Vibrissa Follicle," *Development* 114:887-897 (1992).

Kashiwagi et al., "Specific Inhibition of Hair Follicle Formation by Epidermal Growth Factor in an Organ Culture of Developing Mouse Skin," *Dev. Biol.* 189:22-32 (1997).

Mak and Chan, "Epidermal Growth Factor as a Biologic Switch in Hair Growth Cycle," *J. Biol. Chem.* 278:26120-26126 (2003).

Mattar et al., "Inhibition of the Epidermal Growth Factor Receptor Tyrosine Kinase Activity by Leflunomide," *FEBS Lett.* 334:161-164 (1993).

Ota et al., "Fibroblast Growth Factor 5 Inhibits Hair Growth by Blocking Dermal Papilla Cell Activation," *Biochem. Biophys. Res. Commun.* 290:169-176 (2002).

Saito, "Effects of Epidermal Growth Factor and Transforming Growth Factor on Cultured Hair Follicle Cells from Human Scalp," *Skin* 36:125-133 (1994) (English Language Abstract).

Srivastava et al., "Ectodysplasin-A1 is Sufficient to Rescue Both Hair Growth and Sweat Glands in Tabby Mice," *Hum. Mol. Gene.* 10:2973-2981 (2001).

Tanabe et al., "Wound Treatment-Related Factor and Hair Growth," in Basic Technology Meeting of the Japanese Orthopaedic Association, Program & Abstract 12:118 (2003) (English Language Abstract).

Japanese Notice of Reasons for Rejection for Japanese Patent Application No. 2008-504257, mailed Sep. 6, 2011 (English Language Translation Provided).

* cited by examiner

K 17 immuno-stain

Cuticle, cortex : S100A3          IRS, medulla: S100A6

11 days after wound

AP stain K17 immunostain

FIGURE 22A

| probe set | SEQ ID NO | bs-line mean | bs-line SE | expt mean | expt SE | fold change | lower bound:FC | upper bound:FC | diff. of mean |
|---|---|---|---|---|---|---|---|---|---|
| 160841_at | 1 | -4.59 | 7.45 | 117.99 | 26.08 | 117.99 | 8.2 | 1000000000 | 122.57 |
| 103589_at | 2 | -1.28 | 6.58 | 112.41 | 43.53 | 112.41 | 7.13 | 1000000000 | 113.68 |
| 103562_f_at | 3 | 23.45 | 12.4 | 220.55 | 110.78 | 9.4 | 1.52 | 75.74 | 197.1 |
| 97527_at | 4 | 27.15 | 14.75 | 173.81 | 24.11 | 6.4 | 3.2 | 60.38 | 146.66 |
| 160909_at | 5 | 115.74 | 46.42 | 706.06 | 192.98 | 6.1 | 2.8 | 18.81 | 590.32 |
| 93285_at | 6 | 132.73 | 53.69 | 782.45 | 138.65 | 5.89 | 3.17 | 17.98 | 649.72 |
| 98988_at | 7 | 119.09 | 33.93 | 650.75 | 97.47 | 5.46 | 3.38 | 10.62 | 531.65 |
| 161903_f_at | 8 | 33.82 | 7.85 | 183.08 | 42.87 | 5.41 | 3.03 | 9.65 | 149.26 |
| 97542_at | 9 | 199 | 149.69 | 1009.76 | 317.31 | 5.07 | 1.71 | 1000000000 | 810.76 |
| 104701_at | 10 | 181.01 | 54.87 | 893.77 | 110.08 | 4.94 | 3.1 | 10.04 | 712.76 |
| 94057_g_at | 11 | 194.15 | 36.67 | 895.05 | 169.8 | 4.61 | 2.91 | 7.29 | 700.89 |
| 160092_at | 12 | 142.8 | 67.19 | 637.32 | 153.3 | 4.46 | 2.08 | 20.18 | 494.52 |
| 93527_at | 13 | 55.64 | 18 | 246.09 | 25.21 | 4.42 | 2.77 | 9.57 | 190.46 |
| 92978_s_at | 14 | 208.74 | 82.76 | 904.6 | 260.29 | 4.33 | 1.93 | 13.15 | 695.86 |
| 93985_at | 15 | 117.48 | 43.72 | 505.43 | 102.78 | 4.3 | 2.29 | 11.47 | 387.95 |
| 97197_f_at | 16 | 238.01 | 60.95 | 975.35 | 226.41 | 4.1 | 2.27 | 7.7 | 737.34 |
| 160606_r_at | 17 | 105.16 | 32.48 | 420.67 | 154.57 | 4 | 1.47 | 9.32 | 315.51 |
| 92925_at | 18 | 257.38 | 102.47 | 1023.17 | 152.45 | 3.98 | 2.22 | 11.7 | 765.8 |
| 99849_at | 19 | 611.78 | 159.55 | 2401.77 | 484.37 | 3.93 | 2.29 | 7.33 | 1790 |
| 96295_at | 20 | 147.89 | 44.65 | 548.52 | 112.75 | 3.71 | 2.08 | 7.76 | 400.63 |
| 101554_at | 21 | 561.24 | 162.46 | 1994.33 | 289.7 | 3.55 | 2.2 | 6.99 | 1433.09 |
| 101964_at | 22 | 136.05 | 40.77 | 481.38 | 53.63 | 3.54 | 2.25 | 7.09 | 345.33 |
| 93974_at | 23 | 129.04 | 15.59 | 454.75 | 88.15 | 3.52 | 2.31 | 5.03 | 325.71 |
| 93573_at | 24 | 705.68 | 193.8 | 2449.83 | 87.02 | 3.47 | 2.38 | 6.34 | 1744.15 |
| 162206_f_at | 25 | 283.3 | 111.46 | 948.01 | 188.26 | 3.35 | 1.77 | 9.75 | 664.71 |
| 94056_at | 26 | 380.59 | 72.3 | 1264.27 | 225.61 | 3.32 | 2.14 | 5.22 | 883.68 |
| 101019_at | 27 | 50.97 | 13.15 | 169.04 | 59.25 | 3.32 | 1.32 | 6.77 | 118.07 |
| 160894_at | 28 | 234.87 | 60.8 | 773.72 | 130.11 | 3.29 | 2.04 | 6.01 | 538.85 |
| 102363_r_at | 29 | 483.67 | 195.98 | 1579.93 | 198.13 | 3.27 | 1.86 | 9.9 | 1096.27 |
| 104156_r_at | 30 | 461.52 | 147.14 | 1505.8 | 282.6 | 3.26 | 1.86 | 7.14 | 1044.27 |
| 98083_at | 31 | 265.71 | 64.72 | 829.49 | 157.14 | 3.12 | 1.89 | 5.55 | 563.79 |
| 98589_at | 32 | 237.6 | 42.69 | 733.9 | 54.22 | 3.09 | 2.31 | 4.46 | 496.3 |

FIGURE 22B

| | | | | | | | |
|---|---|---|---|---|---|---|---|
| 101410_at | 33 | 77.22 | 17.11 | 236.17 | 12.53 | 3.06 | 2.21 | 4.84 | 158.95 |
| 102362_i_at | 34 | 590.2 | 219.11 | 1763.85 | 203.43 | 2.99 | 1.77 | 7.76 | 1173.65 |
| 102955_at | 35 | 126.89 | 27.41 | 378.95 | 95.38 | 2.99 | 1.62 | 5.21 | 252.05 |
| 96657_at | 36 | 202.33 | 31.51 | 593.78 | 96.07 | 2.93 | 2 | 4.28 | 391.45 |
| 92232_at | 37 | 318.7 | 94.52 | 932.68 | 64.57 | 2.93 | 1.93 | 5.75 | 613.99 |
| 99457_at | 38 | 70.6 | 9.12 | 200.86 | 50.21 | 2.85 | 1.63 | 4.33 | 130.26 |
| 103665_at | 39 | 137.79 | 18.28 | 391.39 | 104.78 | 2.84 | 1.55 | 4.42 | 253.6 |
| 104149_at | 40 | 593.93 | 166.71 | 1682.3 | 182.25 | 2.83 | 1.84 | 5.36 | 1088.37 |
| 92730_at | 41 | 221.49 | 83.2 | 627.03 | 101.25 | 2.83 | 1.59 | 7.57 | 405.54 |
| 93346_at | 42 | 149.96 | 31.14 | 421.18 | 85.61 | 2.81 | 1.7 | 4.66 | 271.23 |
| 95439_at | 43 | 88.13 | 19 | 245.95 | 59.22 | 2.79 | 1.56 | 4.83 | 157.82 |
| 102049_at | 44 | 94.74 | 20.76 | 262.21 | 46.03 | 2.77 | 1.75 | 4.61 | 167.47 |
| 97909_at | 45 | 249.59 | 47.89 | 689.01 | 94.06 | 2.76 | 1.9 | 4.23 | 439.41 |
| 97546_at | 46 | 133.71 | 39.2 | 365.48 | 46.12 | 2.73 | 1.73 | 5.4 | 231.77 |
| 98829_at | 47 | 470.98 | 294.77 | 1272.68 | 140.61 | 2.7 | 1.29 | 100000000 | 801.7 |
| 160834_at | 48 | 141.39 | 33.56 | 380.2 | 57.73 | 2.69 | 1.74 | 4.61 | 238.81 |
| 99076_at | 49 | 76.48 | 15.08 | 204.33 | 17.28 | 2.67 | 1.94 | 4.03 | 127.85 |
| 102791_at | 50 | 103.99 | 28.25 | 276.51 | 56.18 | 2.66 | 1.54 | 5.11 | 172.52 |
| 99548_at | 51 | 304.99 | 77.26 | 808.21 | 116.83 | 2.65 | 1.7 | 4.71 | 503.23 |
| 160273_at | 52 | 666.44 | 103.7 | 1761.34 | 209.34 | 2.64 | 1.93 | 3.73 | 1094.9 |
| 101487_f_at | 53 | 394.46 | 67.78 | 1039.29 | 199.81 | 2.63 | 1.68 | 4.05 | 644.83 |
| 104712_at | 54 | 163.95 | 30.93 | 426.88 | 44.04 | 2.6 | 1.87 | 3.89 | 262.93 |
| 98469_at | 55 | 68.51 | 16.59 | 178.35 | 23.69 | 2.6 | 1.71 | 4.47 | 109.84 |
| 93058_at | 56 | 79.66 | 9.53 | 206.19 | 32.24 | 2.59 | 1.83 | 3.55 | 126.53 |
| 95348_at | 57 | 113.11 | 26.29 | 291.76 | 31.62 | 2.58 | 1.76 | 4.28 | 178.65 |
| 98627_at | 58 | 75.74 | 13.15 | 192.98 | 18.48 | 2.55 | 1.68 | 3.67 | 117.24 |
| 103905_at | 59 | 85.15 | 18.59 | 216.11 | 31.03 | 2.54 | 1.69 | 4.14 | 130.96 |
| 96704_at | 60 | 1004.68 | 292.32 | 2541.06 | 64.9 | 2.53 | 1.71 | 4.86 | 1536.38 |
| 96841_at | 61 | 148.26 | 37.17 | 373.77 | 37.64 | 2.52 | 1.7 | 4.37 | 225.51 |
| 93528_s_at | 62 | 325.47 | 42.91 | 814.6 | 94.75 | 2.5 | 1.87 | 3.38 | 489.14 |
| 103995_at | 63 | 99.71 | 18.04 | 245.79 | 64.04 | 2.47 | 1.34 | 4.07 | 146.08 |
| 93619_at | 64 | 211.26 | 36.62 | 518.24 | 59.87 | 2.45 | 1.77 | 3.57 | 306.98 |
| 99603_g_at | 65 | 189.95 | 54.67 | 464.45 | 56.46 | 2.45 | 1.56 | 4.74 | 274.5 |

FIGURE 22C

| | | | | | | | |
|---|---|---|---|---|---|---|---|
| 97241_at | 66 | 76.34 | 20.54 | 185.14 | 28.15 | 2.43 | 1.52 | 4.51 | 108.8 |
| 93975_at | 67 | 318.9 | 42.47 | 771.29 | 153.37 | 2.42 | 1.56 | 3.52 | 452.39 |
| 92830_s_at | 68 | 951.79 | 313.65 | 2304.83 | 151.2 | 2.41 | 1.54 | 5.31 | 1353.04 |
| 160359_at | 69 | 125.24 | 14.57 | 301.36 | 29.27 | 2.41 | 1.88 | 3.12 | 176.12 |
| 93250_r_at | 70 | 315.77 | 42.86 | 755.99 | 65.92 | 2.39 | 1.86 | 3.18 | 440.23 |
| 101561_at | 71 | 1691.83 | 299.29 | 3988.08 | 129.84 | 2.36 | 1.81 | 3.34 | 2296.25 |
| 160463_at | 72 | 240.25 | 84.32 | 557.92 | 63.82 | 2.32 | 1.4 | 5.56 | 317.68 |
| 94881_at | 73 | 246.87 | 52.18 | 570.73 | 72.1 | 2.31 | 1.58 | 3.68 | 323.86 |
| 162234_f_at | 74 | 104.55 | 14.78 | 240.86 | 33.15 | 2.3 | 1.66 | 3.22 | 136.31 |
| 92777_at | 75 | 354.22 | 125.82 | 815.02 | 57.76 | 2.3 | 1.43 | 5.56 | 460.8 |
| 97413_at | 76 | 186.46 | 42.02 | 426.43 | 57.65 | 2.29 | 1.53 | 3.78 | 239.97 |
| 93290_at | 77 | 220.69 | 54.35 | 506.12 | 81.35 | 2.29 | 1.45 | 4.04 | 285.43 |
| 93193_at | 78 | 106.8 | 15.31 | 243.51 | 20.34 | 2.28 | 1.76 | 3.07 | 136.71 |
| 160369_at | 79 | 171.88 | 14.05 | 391.54 | 74.72 | 2.28 | 1.53 | 3.11 | 219.66 |
| 102788_s_at | 80 | 202.74 | 39.62 | 459.62 | 105.41 | 2.27 | 1.31 | 3.74 | 256.88 |
| 98862_f_at | 81 | 707.54 | 191.58 | 1602.3 | 269.42 | 2.26 | 1.39 | 4.26 | 894.76 |
| 161666_f_at | 82 | 159.92 | 55.82 | 361.44 | 63.64 | 2.26 | 1.28 | 5.47 | 201.53 |
| 100612_at | 83 | 109.28 | 13.06 | 244.41 | 39.49 | 2.24 | 1.57 | 3.09 | 135.13 |
| 100144_at | 84 | 766.09 | 156.62 | 1706.03 | 266.57 | 2.23 | 1.47 | 3.55 | 939.93 |
| 101065_at | 85 | 328.05 | 58.88 | 730.71 | 145.44 | 2.23 | 1.39 | 3.49 | 402.66 |
| 101876_s_at | 86 | 155.5 | 38.86 | 346.44 | 59.57 | 2.23 | 1.38 | 3.98 | 190.94 |
| 92202_g_at | 87 | 330.57 | 53.31 | 733.66 | 40.66 | 2.22 | 1.72 | 3.05 | 403.09 |
| 102371_at | 88 | 1213.29 | 329.9 | 2695.65 | 108.01 | 2.22 | 1.52 | 4.03 | 1482.37 |
| 103846_at | 89 | 1321.78 | 263.93 | 2925.01 | 471.95 | 2.21 | 1.46 | 3.51 | 1603.23 |
| 94375_at | 90 | 146.6 | 20.7 | 321.94 | 52.11 | 2.2 | 1.51 | 3.13 | 175.34 |
| 101995_at | 91 | 98.55 | 18.7 | 215.04 | 21.12 | 2.18 | 1.58 | 3.26 | 116.49 |
| 100156_at | 92 | 99.29 | 9.58 | 216.55 | 45.69 | 2.18 | 1.39 | 3.08 | 117.26 |
| 94452_g_at | 93 | 120.03 | 28.17 | 261.62 | 55.25 | 2.17 | 1.28 | 3.85 | 141.58 |
| 94805_f_at | 94 | 694.87 | 148.44 | 1505.05 | 159.22 | 2.17 | 1.51 | 3.43 | 810.19 |
| 94011_at | 95 | 512.81 | 134.05 | 1106.93 | 232.4 | 2.16 | 1.24 | 4.05 | 594.13 |
| 102381_at | 96 | 135.96 | 23.62 | 291.09 | 59.57 | 2.14 | 1.33 | 3.34 | 155.12 |
| 160617_at | 97 | 202.28 | 37.36 | 430.01 | 58.22 | 2.13 | 1.47 | 3.21 | 227.74 |
| 94246_at | 98 | 466.99 | 78.37 | 985.61 | 170.81 | 2.11 | 1.4 | 3.17 | 510.61 |

FIGURE 22D

| | | | | | | | |
|---|---|---|---|---|---|---|---|
| 101658_f_at | 99 | 285.59 | 88.76 | 603.43 | 91.07 | 2.11 | 1.28 | 4.44 | 317.83 |
| 160651_at | 100 | 451.96 | 149.58 | 951.74 | 153.08 | 2.11 | 1.23 | 4.75 | 499.70 |
| 99835_at | 101 | 126.74 | 16.43 | 265.21 | 28.87 | 2.09 | 1.59 | 2.8 | 138.46 |
| 94384_at | 102 | 744.33 | 121.74 | 1547.75 | 85.27 | 2.08 | 1.61 | 2.88 | 803.42 |
| 99602_at | 103 | 331.17 | 83.9 | 684.41 | 59.53 | 2.07 | 1.41 | 3.59 | 353.24 |
| 93970_at | 104 | 107.79 | 18.66 | 223.33 | 41.74 | 2.07 | 1.33 | 3.18 | 115.53 |
| 94325_at | 105 | 345.93 | 53.16 | 716.7 | 145.74 | 2.07 | 1.3 | 3.12 | 370.77 |
| 102161_f_at | 106 | 714.47 | 196.16 | 1476.07 | 225.27 | 2.07 | 1.29 | 3.9 | 761.6 |
| 99378_f_at | 107 | 649.9 | 166.98 | 1346.61 | 258.64 | 2.07 | 1.23 | 3.81 | 696.72 |
| 100633_at | 108 | 203.48 | 33.65 | 416.96 | 46.25 | 2.05 | 1.5 | 2.93 | 213.48 |
| 92205_at | 109 | 187.34 | 23.61 | 383.05 | 29.19 | 2.04 | 1.62 | 2.65 | 195.7 |
| 98507_at | 110 | 210.52 | 28.44 | 427.41 | 62.39 | 2.03 | 1.45 | 2.82 | 216.88 |
| 94967_at | 111 | 105.62 | 17.9 | 214.5 | 28.22 | 2.03 | 1.44 | 2.97 | 108.88 |
| 160237_at | 112 | 135.67 | 34.39 | 275.02 | 38.2 | 2.03 | 1.31 | 3.6 | 139.35 |
| 98446_s_at | 113 | 141.88 | 41.45 | 287.07 | 41.58 | 2.02 | 1.25 | 4.01 | 145.19 |
| 96926_at | 114 | 144.45 | 27.93 | 290.46 | 15.29 | 2.01 | 1.5 | 2.97 | 146.01 |
| 92845_at | 115 | 170.95 | 17.73 | 342.33 | 49.39 | 2 | 1.47 | 2.66 | 171.38 |
| 100581_at | 116 | 705.51 | 57.45 | 1408.65 | 224.5 | 2 | 1.44 | 2.63 | 703.14 |
| 104480_at | 117 | 184.72 | 13.66 | 369.2 | 61.29 | 2 | 1.43 | 2.63 | 184.47 |
| 96634_at | 118 | 103.53 | 13.51 | 205.16 | 16.27 | 1.98 | 1.56 | 2.6 | 101.63 |
| 94276_at | 119 | 197.58 | 26.99 | 391.41 | 48.86 | 1.98 | 1.46 | 2.71 | 193.84 |
| 95731_at | 120 | 220.03 | 43.23 | 436.14 | 48.05 | 1.98 | 1.4 | 3.02 | 216.12 |
| 98946_at | 121 | 162.82 | 41.36 | 321.71 | 43.79 | 1.98 | 1.28 | 3.51 | 158.89 |
| 92855_at | 122 | 584.64 | 123.66 | 1154.24 | 120.73 | 1.97 | 1.38 | 3.11 | 569.6 |
| 98545_at | 123 | 237.76 | 53.22 | 464.91 | 55.5 | 1.96 | 1.33 | 3.19 | 227.15 |
| 92625_at | 124 | 397.13 | 83.29 | 780.25 | 118.82 | 1.96 | 1.3 | 3.16 | 303.12 |
| 100618_f_at | 125 | 737.43 | 221.94 | 1443.15 | 153.88 | 1.96 | 1.25 | 3.93 | 705.72 |
| 97826_at | 126 | 831.97 | 82.48 | 1620.67 | 288.56 | 1.95 | 1.34 | 2.67 | 788.7 |
| 96592_at | 127 | 190.99 | 39.76 | 373.19 | 46.44 | 1.95 | 1.34 | 3.08 | 182.19 |
| 95446_at | 128 | 345.12 | 51.28 | 672.7 | 111.59 | 1.95 | 1.33 | 2.82 | 327.59 |
| 93728_at | 129 | 165.51 | 34.39 | 321.77 | 28.72 | 1.94 | 1.39 | 3.01 | 156.26 |
| 103035_at | 130 | 212.61 | 41.86 | 413.17 | 40.37 | 1.94 | 1.39 | 2.95 | 200.56 |
| 102821_s_at | 131 | 332.53 | 54.89 | 646.41 | 115.67 | 1.94 | 1.28 | 2.92 | 313.89 |

FIGURE 22E

| | | | | | | | |
|---|---|---|---|---|---|---|---|
| 94485_at | 132 | 174.54 | 18.63 | 337.38 | 17.63 | 1.93 | 1.61 | 2.38 | 162.84 |
| 96041_at | 133 | 581.54 | 85.07 | 1124.91 | 148.43 | 1.93 | 1.4 | 2.71 | 543.37 |
| 94526_at | 134 | 119.03 | 10.37 | 229.15 | 35.02 | 1.93 | 1.4 | 2.53 | 110.12 |
| 102121_f_at | 135 | 203.34 | 36.01 | 393.38 | 52.67 | 1.93 | 1.35 | 2.87 | 190.03 |
| 101502_at | 136 | 227.82 | 30.05 | 439.1 | 70.68 | 1.93 | 1.34 | 2.71 | 211.29 |
| 160253_at | 137 | 559.17 | 112.52 | 1080.53 | 208.1 | 1.93 | 1.2 | 3.14 | 521.36 |
| 93833_s_at | 138 | 118.76 | 25.65 | 228.26 | 30.94 | 1.92 | 1.29 | 3.11 | 109.51 |
| 97890_at | 139 | 886.59 | 114.32 | 1689.19 | 208.5 | 1.91 | 1.42 | 2.57 | 802.6 |
| 92578_at | 140 | 167.52 | 26.78 | 319.95 | 49.6 | 1.91 | 1.31 | 2.79 | 152.43 |
| 96357_at | 141 | 208.53 | 27.17 | 398.66 | 67.01 | 1.91 | 1.31 | 2.69 | 190.13 |
| 95514_at | 142 | 164.5 | 28.56 | 311.09 | 31.76 | 1.89 | 1.38 | 2.73 | 146.59 |
| 93738_at | 143 | 135.63 | 16.76 | 256.05 | 38.57 | 1.89 | 1.35 | 2.59 | 120.42 |
| 92848_at | 144 | 329.18 | 59.95 | 621.01 | 79.59 | 1.89 | 1.32 | 2.82 | 291.83 |
| 97819_at | 145 | 417.76 | 74.71 | 789.92 | 105.09 | 1.89 | 1.32 | 2.82 | 372.16 |
| 103736_at | 146 | 124.32 | 15.56 | 234.82 | 40.52 | 1.89 | 1.29 | 2.65 | 110.49 |
| 103015_at | 147 | 302.46 | 28.21 | 568.15 | 94.81 | 1.88 | 1.32 | 2.52 | 265.69 |
| 101954_at | 148 | 499.7 | 65.21 | 941.2 | 170.98 | 1.88 | 1.26 | 2.69 | 441.5 |
| 97914_at | 149 | 239.83 | 28.01 | 448.44 | 80.3 | 1.87 | 1.27 | 2.62 | 208.61 |
| 103990_at | 150 | 1427.05 | 431.41 | 2668.76 | 224.52 | 1.87 | 1.21 | 3.76 | 1241.72 |
| 94448_at | 151 | 235 | 27.61 | 436.14 | 53.8 | 1.86 | 1.39 | 2.46 | 201.14 |
| 101589_at | 152 | 314.4 | 38.1 | 582.39 | 71.53 | 1.85 | 1.39 | 2.47 | 267.99 |
| 93844_at | 153 | 321.51 | 64.32 | 596.1 | 69.34 | 1.85 | 1.3 | 2.86 | 274.59 |
| 94837_at | 154 | 388.4 | 69.03 | 718.72 | 96.69 | 1.85 | 1.29 | 2.75 | 330.32 |
| 160415_at | 155 | 424.11 | 58.34 | 778.3 | 86.16 | 1.84 | 1.38 | 2.49 | 354.18 |
| 93581_at | 156 | 203.54 | 51.74 | 373.94 | 25.84 | 1.84 | 1.27 | 3.19 | 170.4 |
| 96866_at | 157 | 176.53 | 22.06 | 323.63 | 37.09 | 1.83 | 1.39 | 2.44 | 147.1 |
| 97456_at | 158 | 213.02 | 29.46 | 390.07 | 48.64 | 1.83 | 1.35 | 2.52 | 177.05 |
| 95518_at | 159 | 339.31 | 32.71 | 620.19 | 93.36 | 1.83 | 1.33 | 2.42 | 280.88 |
| 99109_at | 160 | 1264.78 | 364.09 | 2315.1 | 123.26 | 1.83 | 1.23 | 3.49 | 1050.32 |
| 92861_l_at | 161 | 752.97 | 134.96 | 1369.66 | 155.42 | 1.82 | 1.31 | 2.68 | 616.69 |
| 98608_at | 162 | 220.94 | 24.33 | 399.97 | 47.71 | 1.81 | 1.38 | 2.37 | 179.03 |
| 93119_at | 163 | 411.82 | 64.25 | 746.17 | 89.81 | 1.81 | 1.32 | 2.56 | 334.36 |
| 104155_f_at | 164 | 1737.95 | 437.64 | 3138.54 | 128.49 | 1.81 | 1.27 | 3.09 | 1400.59 |

FIGURE 22F

| Probe | # | | | | | | |
|---|---|---|---|---|---|---|---|
| 160321_at | 165 | 218.41 | 25.78 | 395.96 | 64.49 | 1.81 | 1.27 | 2.5 | 177.55 |
| 100617_at | 166 | 1161.14 | 143.75 | 2096.53 | 335.8 | 1.81 | 1.26 | 2.5 | 935.39 |
| 103980_at | 167 | 140.65 | 23.54 | 253.19 | 23.59 | 1.8 | 1.34 | 2.56 | 112.54 |
| 94789_r_at | 168 | 601.41 | 109.67 | 1080.26 | 78.55 | 1.8 | 1.34 | 2.61 | 478.85 |
| 99643_f_at | 169 | 319 | 24.89 | 569.9 | 65.84 | 1.79 | 1.4 | 2.23 | 250.9 |
| 99133_at | 170 | 590.99 | 89.73 | 1055.14 | 72.4 | 1.79 | 1.39 | 2.42 | 464.15 |
| 93309_at | 171 | 233.93 | 36.64 | 418.52 | 42.99 | 1.79 | 1.33 | 2.5 | 184.59 |
| 92523_at | 172 | 250.73 | 25.34 | 449.69 | 71.54 | 1.79 | 1.28 | 2.41 | 198.96 |
| 100332_s_at | 173 | 208.03 | 48.17 | 371.64 | 18.02 | 1.79 | 1.28 | 2.9 | 163.61 |
| 160832_at | 174 | 308.34 | 41.38 | 551.8 | 80.83 | 1.79 | 1.27 | 2.49 | 243.46 |
| 103715_at | 175 | 173.45 | 25.07 | 308.76 | 42.06 | 1.78 | 1.28 | 2.49 | 135.31 |
| 93865_s_at | 176 | 169.23 | 21.49 | 299.7 | 39.44 | 1.77 | 1.3 | 2.4 | 130.47 |
| 100557_g_at | 177 | 383.54 | 88.02 | 679.22 | 63.17 | 1.77 | 1.23 | 2.9 | 295.69 |
| 93753_at | 178 | 360.92 | 31.33 | 633.75 | 85.9 | 1.76 | 1.32 | 2.26 | 272.82 |
| 92562_at | 179 | 207.67 | 23.98 | 366.25 | 58.35 | 1.76 | 1.24 | 2.41 | 158.58 |
| 92829_at | 180 | 489.72 | 42 | 854.63 | 124.19 | 1.75 | 1.29 | 2.27 | 364.91 |
| 104410_at | 181 | 246.52 | 31.44 | 430.65 | 61.19 | 1.75 | 1.26 | 2.39 | 184.13 |
| 99106_at | 182 | 144.13 | 12.82 | 252.81 | 42.37 | 1.75 | 1.24 | 2.35 | 108.68 |
| 98059_s_at | 183 | 1207.59 | 325.93 | 2116.17 | 106.63 | 1.75 | 1.2 | 3.16 | 908.58 |
| 160383_at | 184 | 362.28 | 56 | 631.49 | 47.87 | 1.74 | 1.34 | 2.39 | 269.21 |
| 92986_g_at | 185 | 166.57 | 14.19 | 290.15 | 37.21 | 1.74 | 1.33 | 2.22 | 123.57 |
| 93104_at | 186 | 542.76 | 93.36 | 945.49 | 92.87 | 1.74 | 1.28 | 2.5 | 402.74 |
| 95697_at | 187 | 635.08 | 135.07 | 1103.54 | 97.58 | 1.74 | 1.24 | 2.72 | 468.47 |
| 96258_at | 188 | 211.85 | 36.09 | 365.74 | 32.96 | 1.73 | 1.28 | 2.46 | 153.89 |
| 94806_at | 189 | 218.46 | 32.82 | 378.12 | 46.11 | 1.73 | 1.26 | 2.42 | 159.66 |
| 96899_at | 190 | 178.06 | 30.62 | 308.09 | 36.14 | 1.73 | 1.24 | 2.52 | 130.03 |
| 97751_f_at | 191 | 658.6 | 107.19 | 1141.8 | 151.91 | 1.73 | 1.23 | 2.5 | 403.2 |
| 93277_at | 192 | 505.99 | 44.71 | 874.53 | 145.9 | 1.73 | 1.22 | 2.31 | 368.54 |
| 101214_f_at | 193 | 685.55 | 109.92 | 1182.57 | 109.46 | 1.72 | 1.29 | 2.41 | 497.02 |
| 100595_at | 194 | 237.36 | 25.26 | 407.84 | 55.12 | 1.72 | 1.28 | 2.27 | 170.47 |
| 98472_at | 195 | 651.55 | 118.79 | 1119.49 | 134.47 | 1.72 | 1.22 | 2.56 | 467.94 |
| 101989_at | 196 | 570.91 | 114.95 | 974.97 | 77.6 | 1.71 | 1.24 | 2.6 | 404.06 |
| 93029_at | 197 | 187.78 | 36.47 | 321.07 | 37.75 | 1.71 | 1.2 | 2.61 | 133.29 |

FIGURE 22G

| | | | | | | | |
|---|---|---|---|---|---|---|---|
| 96353_at | 198 | 171.48 | 29.57 | 291.99 | 26.09 | 1.7 | 1.27 | 2.44 | 120.52 |
| 99642_i_at | 199 | 290.17 | 36.11 | 492.69 | 65.91 | 1.7 | 1.25 | 2.3 | 202.52 |
| 98505_i_at | 200 | 276.98 | 10.47 | 471.34 | 79.76 | 1.7 | 1.22 | 2.19 | 194.37 |
| 93818_g_at | 201 | 365.43 | 53.8 | 615.41 | 50.44 | 1.68 | 1.3 | 2.28 | 249.98 |
| 94489_at | 202 | 678.41 | 80.48 | 1140.47 | 120.27 | 1.68 | 1.3 | 2.2 | 462.07 |
| 98447_at | 203 | 474.58 | 68.17 | 797.13 | 65.87 | 1.68 | 1.3 | 2.26 | 322.55 |
| 101906_at | 204 | 195.27 | 13.72 | 328.07 | 43.2 | 1.68 | 1.29 | 2.12 | 132.79 |
| 100599_at | 205 | 590.8 | 50.09 | 988.25 | 112.1 | 1.67 | 1.31 | 2.1 | 397.45 |
| 94062_at | 206 | 293.1 | 32.58 | 485.75 | 61.45 | 1.66 | 1.24 | 2.19 | 192.66 |
| 97386_at | 207 | 281.32 | 33.9 | 464.62 | 46.81 | 1.65 | 1.28 | 2.16 | 183.3 |
| 100578_at | 208 | 359.42 | 48.01 | 592.91 | 61.72 | 1.65 | 1.25 | 2.21 | 233.49 |
| 98438_f_at | 209 | 1400 | 229.84 | 2305.65 | 172.46 | 1.65 | 1.25 | 2.3 | 905.65 |
| 103612_at | 210 | 586.37 | 64.7 | 961.03 | 78.44 | 1.64 | 1.31 | 2.08 | 374.66 |
| 160246_at | 211 | 218.98 | 23.47 | 358.79 | 45.78 | 1.64 | 1.23 | 2.15 | 139.81 |
| 92958_at | 212 | 197.31 | 18.13 | 321.1 | 12.53 | 1.63 | 1.39 | 1.94 | 123.79 |
| 93023_f_at | 213 | 1289.41 | 185.86 | 2104.73 | 90.02 | 1.63 | 1.3 | 2.15 | 815.32 |
| 160568_at | 214 | 312.65 | 31.22 | 508.7 | 70.08 | 1.63 | 1.21 | 2.14 | 196.06 |
| 92816_r_at | 215 | 461.32 | 64.04 | 752.55 | 93.39 | 1.63 | 1.2 | 2.24 | 291.23 |
| 98937_at | 216 | 195.45 | 27 | 317.11 | 20.14 | 1.62 | 1.28 | 2.14 | 121.67 |
| 160451_at | 217 | 210.95 | 25.47 | 341.15 | 38.6 | 1.62 | 1.23 | 2.14 | 130.2 |
| 93714_f_at | 218 | 1503.18 | 228.1 | 2418.85 | 193.58 | 1.61 | 1.24 | 2.2 | 915.67 |
| 160090_f_at | 219 | 680.13 | 60.49 | 1097.27 | 134.99 | 1.61 | 1.24 | 2.06 | 417.13 |
| 96755_at | 220 | 262.5 | 36.34 | 420.8 | 38.88 | 1.6 | 1.23 | 2.15 | 158.3 |
| 93354_at | 221 | 674.48 | 86.44 | 1059.32 | 74.23 | 1.57 | 1.25 | 2.04 | 384.83 |
| 93071_at | 222 | 434.6 | 69 | 682.99 | 36.08 | 1.57 | 1.22 | 2.15 | 248.4 |
| 93164_at | 223 | 431.59 | 34.88 | 673.83 | 41.04 | 1.56 | 1.33 | 1.85 | 242.23 |
| 100128_at | 224 | 247.99 | 29.26 | 385.76 | 26.99 | 1.56 | 1.25 | 1.98 | 137.77 |
| 93057_at | 225 | 612.72 | 56.09 | 945.97 | 107.03 | 1.54 | 1.2 | 1.96 | 333.24 |
| 103416_at | 226 | 297.37 | 17.14 | 454.06 | 55.15 | 1.53 | 1.2 | 1.88 | 156.69 |
| 95069_at | 227 | 204.72 | 17.73 | 310.68 | 31.68 | 1.52 | 1.21 | 1.89 | 105.96 |
| 93274_at | 228 | 455.45 | 34.85 | 607.58 | 68.3 | 1.51 | 1.22 | 1.85 | 232.13 |
| 101112_g_at | 229 | 316.94 | 39.38 | 479.63 | 30.55 | 1.51 | 1.22 | 1.94 | 162.69 |
| 96416_f_at | 230 | 1047.69 | 154.71 | 1580.26 | 36.04 | 1.51 | 1.21 | 2 | 532.57 |

FIGURE 22H

| | | | | | | | |
|---|---|---|---|---|---|---|---|
| 96115_at | 231 | 802.18 | 67.27 | 1307.78 | 60.20 | 1.48 | 1.28 | 1.73 | 425.6 |
| 162358_l_at | 232 | 260.46 | 28.47 | 382.39 | 11.42 | 1.47 | 1.23 | 1.8 | 121.92 |

FIGURE 22I

| SEQ ID No | A1- High | A2- ctrl | A3- ctrl | A4- ctrl | High-dep A1 | High_dep A2 | High-dep A4 |
|---|---|---|---|---|---|---|---|
| 1 | -5.63 | -17.67 | -5.17 | 6.77 | 83.12 | 169.99 | 100.58 |
| 2 | -2.54 | -14.06 | 0.94 | 10.82 | 87.42 | 54.4 | 195.99 |
| 3 | 23.31 | 8.36 | 7.01 | 53.96 | 38.68 | 208.2 | 417.26 |
| 4 | 19.77 | 2.26 | 24.49 | 58.97 | 205.62 | 127.45 | 188.14 |
| 5 | 139.28 | 52.41 | 114.17 | 154.8 | 635.15 | 417.84 | 1060.26 |
| 6 | 39.56 | 63.62 | 152.7 | 275.17 | 1060.5 | 629.24 | 658.28 |
| 7 | 110.88 | 59.72 | 89.21 | 214.03 | 728.78 | 468.04 | 764.58 |
| 8 | 32.41 | 21.49 | 24.37 | 54.71 | 255 | 107.37 | 188.45 |
| 9 | 331.43 | -167.33 | 163.29 | 469.3 | 481.09 | 1002.95 | 1554.39 |
| 10 | 116.76 | 108.93 | 156.49 | 342 | 1063.9 | 692.84 | 928.59 |
| 11 | 283.17 | 121.9 | 170.16 | 205.78 | 1011.81 | 567.07 | 1110.23 |
| 12 | 74.97 | 22.58 | 143.49 | 331.85 | 942.05 | 448.77 | 522.72 |
| 13 | 42.96 | 17.71 | 59.52 | 96.43 | 288.14 | 207.8 | 245.94 |
| 14 | 444.42 | 87.63 | 119.71 | 180.16 | 943.76 | 445.53 | 1329.18 |
| 15 | 78.04 | 27.45 | 130.69 | 228.96 | 704.54 | 350.25 | 453.08 |
| 16 | 221.31 | 82.68 | 273.71 | 375.27 | 720.98 | 786.45 | 1419.72 |
| 17 | 68.92 | 41.02 | 121.74 | 188.95 | 730.1 | 262.37 | 269.51 |
| 18 | 129.38 | 43.78 | 378.11 | 479.44 | 1325.48 | 831.71 | 919.9 |
| 19 | 418.78 | 404.48 | 559.46 | 1077.69 | 2507.7 | 1533.6 | 3167.77 |
| 20 | 256.89 | 60.48 | 111.55 | 157.48 | 478.62 | 401.72 | 765.65 |
| 21 | 442.7 | 254.33 | 526.58 | 1016.59 | 2409.26 | 1449.07 | 2138.65 |
| 22 | 114.71 | 44.84 | 149.01 | 227.39 | 581.81 | 403.71 | 454.3 |
| 23 | 140.81 | 93.38 | 119.51 | 155.72 | 371.38 | 380.48 | 623.48 |
| 24 | 720.51 | 156.21 | 941.53 | 1000.88 | 2478.16 | 2355.04 | 2547.28 |
| 25 | 192.27 | 92.36 | 240.88 | 605.76 | 1169.42 | 577.85 | 1099.93 |
| 26 | 580.94 | 313.16 | 283.46 | 347.07 | 1341.64 | 851.31 | 1604.33 |
| 27 | 84.02 | 29.36 | 36.55 | 53.49 | 134.3 | 91.56 | 282.49 |
| 28 | 143.01 | 123.84 | 298.75 | 373.89 | 1005.66 | 557.55 | 761.95 |
| 29 | 320.38 | 113.16 | 481.11 | 1025.22 | 1437.46 | 1952.41 | 1354.26 |
| 30 | 296.03 | 137.39 | 718.51 | 695.82 | 2067.63 | 1311.65 | 1152.53 |
| 31 | 214.27 | 126.52 | 314.52 | 408.07 | 1145.61 | 689.57 | 663.78 |
| 32 | 206.21 | 153.91 | 280.51 | 297.21 | 837.74 | 708.2 | 660.62 |
| 33 | 81.04 | 51.06 | 75.14 | 98.1 | 233.5 | 241.15 | 234.39 |
| 34 | 395.98 | 128.67 | 700.46 | 1145.39 | 1809.54 | 2080.32 | 1412.16 |
| 35 | 65.85 | 99.89 | 157.89 | 185.62 | 569.39 | 266.39 | 301.91 |
| 36 | 263.18 | 139.8 | 182.15 | 218.92 | 598.64 | 431.27 | 753.7 |
| 37 | 177.42 | 150.27 | 399.45 | 540.28 | 983.19 | 832.33 | 997.4 |
| 38 | 74.75 | 74.97 | 48.84 | 82.72 | 182.41 | 128.43 | 293.82 |
| 39 | 150.84 | 95.39 | 167.23 | 138.08 | 392.12 | 214.37 | 570.07 |
| 40 | 540.31 | 300.82 | 465.12 | 1073.48 | 1938.91 | 1348.09 | 1771.78 |
| 41 | 132.57 | 108.3 | 176.91 | 468.34 | 826.57 | 495.76 | 559.84 |
| 42 | 202.76 | 65.77 | 160.86 | 161.92 | 501.64 | 253.72 | 509.75 |
| 43 | 70.85 | 48.97 | 117.21 | 117.12 | 212.32 | 168.69 | 357.86 |
| 44 | 59.89 | 73.74 | 89.86 | 151.61 | 354.26 | 227.02 | 207.74 |
| 45 | 262.7 | 140.08 | 223.83 | 362.92 | 768 | 506.51 | 792.68 |
| 46 | 203.13 | 24.19 | 141.14 | 188.52 | 396.35 | 278.68 | 423.13 |
| 47 | 1249.11 | -163.61 | 288.35 | 509.86 | 1213.24 | 1064.64 | 1540.1 |
| 48 | 112.44 | 70.65 | 156.69 | 225.29 | 470.4 | 278.49 | 398.79 |
| 49 | 78.27 | 43.65 | 67.66 | 114.57 | 215.12 | 174.03 | 225.14 |

FIGURE 22J

| | | | | | | | |
|---|---|---|---|---|---|---|---|
| 50 | 132.5 | 26.28 | 122.03 | 135.16 | 277.18 | 181.31 | 371.58 |
| 51 | 262.43 | 112.26 | 371.84 | 470.08 | 711.07 | 681.81 | 1033.8 |
| 52 | 538.76 | 461.17 | 769.77 | 889.81 | 1975.05 | 1352.89 | 1950.32 |
| 53 | 438.88 | 225 | 382.84 | 525.6 | 835.86 | 857.62 | 1428.27 |
| 54 | 141.38 | 90.71 | 202.04 | 223.68 | 495.75 | 346.79 | 438.26 |
| 55 | 74.78 | 50.42 | 52.47 | 86.4 | 192.43 | 139.97 | 206.83 |
| 56 | 79.05 | 66.18 | 67.55 | 103.4 | 264.65 | 154.74 | 201.21 |
| 57 | 80.07 | 90.7 | 102.4 | 176.88 | 281.97 | 349.67 | 243.8 |
| 58 | 68.4 | 106.51 | 76.83 | 59.14 | 167.01 | 225.34 | 186.51 |
| 59 | 83.86 | 39.01 | 93.03 | 123.08 | 222.12 | 150.9 | 284.71 |
| 60 | 1296.17 | 167.7 | 1103.2 | 1462.67 | 2516.18 | 2486.75 | 2606.4 |
| 61 | 149.99 | 61.1 | 151.09 | 218.82 | 346.11 | 438.58 | 339.9 |
| 62 | 215.58 | 309.49 | 355.1 | 416.34 | 941.89 | 641.57 | 865.1 |
| 63 | 137.69 | 69.83 | 69.95 | 117.25 | 233.19 | 145.75 | 360.25 |
| 64 | 176.23 | 129.22 | 287.4 | 244.63 | 611.3 | 538.23 | 410.26 |
| 65 | 135.04 | 70.48 | 243.79 | 312.9 | 563.01 | 370.79 | 457.06 |
| 66 | 65.19 | 25.39 | 94.18 | 120.53 | 218.57 | 131.58 | 207.17 |
| 67 | 356.76 | 227.22 | 367.73 | 327.65 | 715.66 | 626.94 | 1034.2 |
| 68 | 643.68 | 299.61 | 1106.73 | 1751.38 | 2436.92 | 2465.26 | 2012.95 |
| 69 | 119.23 | 94.41 | 135.34 | 146.07 | 349.59 | 254.82 | 301.39 |
| 70 | 360.47 | 304.94 | 200.13 | 397.18 | 812.63 | 626.76 | 826.71 |
| 71 | 1701.31 | 921.16 | 1800.76 | 2328.77 | 4084.28 | 3803.84 | 4121.35 |
| 72 | 101 | 107.87 | 287.29 | 454.65 | 684.09 | 490.91 | 508.17 |
| 73 | 346.1 | 105.04 | 284.96 | 271.03 | 707.56 | 464.44 | 544.27 |
| 74 | 85.55 | 89.81 | 95.56 | 146.28 | 262.05 | 181.42 | 283.51 |
| 75 | 182.89 | 96.32 | 560.09 | 578.66 | 860.12 | 883.46 | 701.98 |
| 76 | 115.65 | 123.07 | 243.02 | 261.83 | 523.34 | 333.37 | 432.41 |
| 77 | 198.8 | 93.34 | 229.65 | 356.53 | 561.03 | 352.4 | 609.09 |
| 78 | 93.9 | 77.52 | 124.29 | 133.58 | 283.15 | 228.24 | 224.33 |
| 79 | 149.09 | 174.43 | 183.43 | 179 | 525.24 | 268.7 | 384.89 |
| 80 | 163.12 | 123.1 | 266.84 | 253.62 | 470.88 | 274.31 | 633.27 |
| 81 | 511.47 | 273.07 | 950.77 | 1091.08 | 1547.45 | 1179.77 | 2083.79 |
| 82 | 131.81 | 52.72 | 137.49 | 317.72 | 382.99 | 247.01 | 456.6 |
| 83 | 119.97 | 78 | 102.46 | 124.31 | 250.65 | 174.67 | 308.27 |
| 84 | 946.19 | 351.71 | 705.88 | 1059.06 | 1534.13 | 1361.23 | 2222.82 |
| 85 | 298.4 | 248.35 | 262.8 | 500.23 | 730.02 | 490.82 | 977.92 |
| 86 | 126.17 | 60.47 | 225.06 | 210.49 | 298.85 | 278.49 | 462.49 |
| 87 | 204.53 | 399.01 | 430.57 | 291 | 748.26 | 669.68 | 788.41 |
| 88 | 897.74 | 464 | 1566.84 | 1813.81 | 2787.91 | 2754.92 | 2592.71 |
| 89 | 1876.3 | 682.31 | 1158.85 | 1527.08 | 3819.6 | 2224.18 | 2746.01 |
| 90 | 109.7 | 130.79 | 142.04 | 203.42 | 416.8 | 240.51 | 313.38 |
| 91 | 70.83 | 65.03 | 116.01 | 137.3 | 243.19 | 178.45 | 227.11 |
| 92 | 104.22 | 80.52 | 100.91 | 111.37 | 166.84 | 178.35 | 305.19 |
| 93 | 160.76 | 41.21 | 121.95 | 155.07 | 261.42 | 168.61 | 355.69 |
| 94 | 1002.21 | 376.59 | 623.8 | 798.55 | 1496.07 | 1240.29 | 1771.65 |
| 95 | 565.29 | 155.67 | 524.23 | 804.82 | 1036.06 | 747.88 | 1536.56 |
| 96 | 83.36 | 127.14 | 137.58 | 196.8 | 262.3 | 209.25 | 402.22 |
| 97 | 170.87 | 118.9 | 283.84 | 230 | 370.12 | 379.44 | 542.27 |
| 98 | 510.11 | 255.73 | 467.06 | 628.25 | 1295.4 | 706.07 | 958.06 |
| 99 | 460.1 | 53.41 | 304.69 | 327.47 | 443.97 | 628.87 | 737.78 |

FIGURE 22K

| | | | | | | | |
|---|---|---|---|---|---|---|---|
| 100 | 863.6 | 207.42 | 306.15 | 435.08 | 951.34 | 699.25 | 1208.97 |
| 101 | 115.92 | 128.12 | 128.12 | 137.12 | 321.41 | 245.54 | 230.42 |
| 102 | 609.66 | 500.34 | 785.38 | 1034.85 | 1585.94 | 1451 | 1624.77 |
| 103 | 264.25 | 164.9 | 333.89 | 561.29 | 779.16 | 607.88 | 894.78 |
| 104 | 123.78 | 64.68 | 93.68 | 149.27 | 251.83 | 142.53 | 276.23 |
| 105 | 448.92 | 217.48 | 316.74 | 404.21 | 792.91 | 438.86 | 920.02 |
| 106 | 872.5 | 136.08 | 872.47 | 976.55 | 1308.91 | 1211.31 | 1907.24 |
| 107 | 782.84 | 160.15 | 782.21 | 875.83 | 1103.1 | 1100.16 | 1844.59 |
| 108 | 183.5 | 120.8 | 230.11 | 274.68 | 502.11 | 346.62 | 406.3 |
| 109 | 145.22 | 154.75 | 215.32 | 223.86 | 402.89 | 331.79 | 416.36 |
| 110 | 242.68 | 131.21 | 227.3 | 239.68 | 545.7 | 407.72 | 334.91 |
| 111 | 152.64 | 73.67 | 94.27 | 97.84 | 216.43 | 168.83 | 260.02 |
| 112 | 137.9 | 40.27 | 191.51 | 171.56 | 349.06 | 223.32 | 253.36 |
| 113 | 231.99 | 37.75 | 125.33 | 172.57 | 318.72 | 207 | 336.68 |
| 114 | 129.7 | 79.03 | 166.88 | 193.5 | 277.7 | 286.34 | 305.25 |
| 115 | 151.91 | 143.6 | 165.79 | 218.92 | 406.78 | 248.28 | 374.11 |
| 116 | 688 | 569.04 | 732.38 | 823.69 | 1470.55 | 998.09 | 1757.45 |
| 117 | 177.77 | 181.58 | 163.05 | 216.72 | 349.95 | 275.4 | 480.9 |
| 118 | 67.73 | 111.6 | 121.41 | 116 | 229.84 | 178.33 | 208.33 |
| 119 | 186.4 | 143.44 | 190.67 | 266.45 | 474.18 | 308.84 | 393.31 |
| 120 | 213.57 | 102.11 | 277.63 | 286.81 | 395.79 | 387.24 | 528.05 |
| 121 | 153.49 | 76.2 | 145.61 | 274.72 | 403.36 | 255.75 | 309.24 |
| 122 | 511.99 | 296.95 | 641.95 | 887.33 | 1370.99 | 960.71 | 1133.77 |
| 123 | 255.48 | 96.57 | 246.27 | 353.38 | 455.98 | 378.23 | 562.17 |
| 124 | 519.52 | 161.83 | 403.43 | 502.64 | 902.52 | 546.05 | 893.71 |
| 125 | 1059.81 | 121.89 | 723.62 | 1035.98 | 1346.89 | 1263.28 | 1730.1 |
| 126 | 794.58 | 646.29 | 894.06 | 979.75 | 1585.26 | 1153.91 | 2124.6 |
| 127 | 182.15 | 100.35 | 187.18 | 293.39 | 300.2 | 373.46 | 449.27 |
| 128 | 310.84 | 246.38 | 333.32 | 488.12 | 876.51 | 493.78 | 651.77 |
| 129 | 152.43 | 89.76 | 166.79 | 251.84 | 357.65 | 267 | 340.43 |
| 130 | 207.57 | 100.38 | 282.81 | 259.08 | 458.54 | 335.38 | 446.38 |
| 131 | 455.54 | 202.21 | 301.47 | 370.84 | 756.41 | 417.26 | 766.51 |
| 132 | 145.05 | 144.44 | 187.68 | 216.41 | 338.95 | 310.57 | 362.17 |
| 133 | 554.11 | 402.15 | 567.63 | 809.76 | 1292.17 | 844.8 | 1249.13 |
| 134 | 130.24 | 103.48 | 113.49 | 126.1 | 297.16 | 184.92 | 204.95 |
| 135 | 186.7 | 119.75 | 269.61 | 216.49 | 446.72 | 288.14 | 445.05 |
| 136 | 189.47 | 168.95 | 262.02 | 293.93 | 548.58 | 309.28 | 462.05 |
| 137 | 638.29 | 239.8 | 626.95 | 717.65 | 999.55 | 774.33 | 1465.56 |
| 138 | 124.73 | 52.62 | 119.62 | 177.26 | 234.37 | 175.19 | 275.85 |
| 139 | 829.09 | 706.34 | 788.34 | 1218.18 | 1732 | 1318.01 | 2016.68 |
| 140 | 196.56 | 96.26 | 168.71 | 211.3 | 409.32 | 239.57 | 313.52 |
| 141 | 194.4 | 142.96 | 233.73 | 282.23 | 436.12 | 272.78 | 488.44 |
| 142 | 144.74 | 96.33 | 183.54 | 226.73 | 338.13 | 260.1 | 343.18 |
| 143 | 132.94 | 103.91 | 170.64 | 131.81 | 328.78 | 200.99 | 237.08 |
| 144 | 385.59 | 190.9 | 277.34 | 461.73 | 691.3 | 468.98 | 705.79 |
| 145 | 479.58 | 201.87 | 479.88 | 510.07 | 855.6 | 589.24 | 927.23 |
| 146 | 82.02 | 125.19 | 133.96 | 158.08 | 293.82 | 157.63 | 253.33 |
| 147 | 242.78 | 269.89 | 348.64 | 344.92 | 707.32 | 393.24 | 610.03 |
| 148 | 565.1 | 394.93 | 387.65 | 642.06 | 948.42 | 655.01 | 1228.65 |
| 149 | 275.94 | 169.57 | 227.25 | 286.38 | 493.91 | 297.39 | 557.13 |

FIGURE 22L

| | | | | | | | |
|---|---|---|---|---|---|---|---|
| 150 | 781.55 | 580.02 | 2127.05 | 2208.06 | 3043.92 | 2702.29 | 2282.46 |
| 151 | 261.4 | 158.9 | 250.2 | 264.02 | 505.64 | 334.83 | 472.08 |
| 152 | 372.91 | 232.5 | 286.71 | 377.42 | 687.16 | 450.09 | 612.82 |
| 153 | 410.42 | 131.97 | 369.05 | 367.78 | 720.73 | 484.99 | 582.85 |
| 154 | 461.07 | 191.03 | 424.7 | 468.61 | 797.92 | 532.2 | 829.45 |
| 155 | 546.5 | 268.31 | 446.34 | 433.67 | 794.32 | 630 | 915.07 |
| 156 | 282.84 | 57.22 | 211.57 | 257.88 | 396.65 | 328.24 | 398.79 |
| 157 | 201.46 | 120.48 | 177.34 | 191.62 | 357.2 | 254.61 | 361.88 |
| 158 | 232.31 | 128.28 | 247.88 | 241.71 | 440.6 | 294.47 | 435.39 |
| 159 | 334.05 | 275.32 | 324.52 | 425.52 | 772.85 | 454.43 | 637.76 |
| 160 | 1051.89 | 397.67 | 1479.38 | 2126.13 | 2268.38 | 2529.2 | 2169.17 |
| 161 | 798.21 | 399.8 | 899.89 | 912.54 | 1287.69 | 1165.36 | 1655.86 |
| 162 | 244.32 | 157.06 | 225.73 | 253.07 | 427.09 | 313.85 | 463.56 |
| 163 | 438.76 | 226.89 | 457.14 | 513.87 | 898.95 | 594.47 | 745.37 |
| 164 | 1352.95 | 718.09 | 2236.02 | 2654.99 | 3278.78 | 3093.26 | 3118.24 |
| 165 | 214.2 | 173.96 | 194.94 | 287.47 | 464.04 | 272.6 | 455.63 |
| 166 | 1255.18 | 786.4 | 1150.85 | 1467.91 | 2159.71 | 1497.04 | 2635.45 |
| 167 | 126.6 | 89.26 | 180.85 | 154.61 | 268.42 | 225.32 | 276.81 |
| 168 | 771.24 | 305.25 | 587.97 | 728 | 1144.4 | 942.94 | 1161.59 |
| 169 | 253.57 | 319.12 | 316.73 | 380.47 | 669.63 | 447.63 | 593.13 |
| 170 | 590.2 | 359.6 | 608.4 | 795.03 | 1151.48 | 940.65 | 1093.9 |
| 171 | 240.81 | 133.89 | 251.93 | 307.57 | 489.86 | 345.71 | 424.47 |
| 172 | 261.55 | 218.92 | 220.14 | 275.29 | 400.11 | 375.64 | 584.55 |
| 173 | 293.62 | 82.87 | 186.43 | 269.33 | 379.84 | 345.41 | 394.6 |
| 174 | 317.27 | 208 | 305.44 | 404.98 | 669.86 | 404.54 | 588.74 |
| 175 | 210.83 | 108.43 | 178.61 | 189.73 | 297.39 | 249.07 | 382.93 |
| 176 | 148.52 | 120.38 | 201.64 | 203.61 | 293.01 | 238.39 | 369.71 |
| 177 | 389.88 | 142.96 | 438.38 | 558.24 | 611.53 | 633.48 | 795.43 |
| 178 | 351.77 | 286.84 | 364.72 | 436.79 | 792.97 | 498.19 | 611.18 |
| 179 | 189.25 | 165.89 | 196.05 | 273.16 | 411.47 | 252.37 | 435.01 |
| 180 | 549.81 | 444.28 | 396.42 | 562.95 | 980.17 | 611.93 | 973.6 |
| 181 | 256.18 | 158.27 | 285.46 | 278.17 | 552.75 | 388.78 | 362.56 |
| 182 | 158.87 | 122.18 | 130.52 | 158.92 | 323.99 | 182.08 | 258.41 |
| 183 | 1266.87 | 291.34 | 1465.85 | 1809.88 | 1981.71 | 2056.61 | 2286.62 |
| 184 | 441.84 | 217.7 | 330.57 | 455.9 | 703.49 | 549.05 | 646.54 |
| 185 | 189.38 | 134.13 | 158.87 | 184.24 | 293.44 | 226.46 | 351.53 |
| 186 | 662.11 | 281.63 | 567.42 | 645.45 | 1043.8 | 769.32 | 1024.99 |
| 187 | 863.99 | 258.52 | 643.98 | 775.24 | 1117.04 | 935.31 | 1259.67 |
| 188 | 250.42 | 107.62 | 249.84 | 237.46 | 404.92 | 391.03 | 300.92 |
| 189 | 268.86 | 131.02 | 211.1 | 263.99 | 412.1 | 289.7 | 433.76 |
| 190 | 202.48 | 88.45 | 208.4 | 211.97 | 366.42 | 245.83 | 315.38 |
| 191 | 763.84 | 372.77 | 638.07 | 854.79 | 1250.89 | 844.06 | 1330.22 |
| 192 | 579.01 | 403.81 | 461.65 | 580.39 | 930.22 | 604.38 | 1090.47 |
| 193 | 759.99 | 385.43 | 693.85 | 904.07 | 1217.27 | 982.86 | 1345.6 |
| 194 | 218.54 | 189.34 | 293.62 | 244.62 | 464.88 | 302.69 | 459.29 |
| 195 | 548.82 | 366.81 | 834.12 | 848.12 | 1219.9 | 862.27 | 1278.38 |
| 196 | 680.15 | 231.09 | 644.14 | 722.42 | 1096.65 | 839.03 | 998.58 |
| 197 | 200.26 | 89.81 | 194.73 | 265.83 | 363.25 | 250.69 | 353.76 |
| 198 | 195.2 | 85.23 | 185.31 | 214.94 | 331.76 | 248.9 | 298.72 |
| 199 | 212 | 250.08 | 339.99 | 361.59 | 598.36 | 376.5 | 508.79 |

FIGURE 22M

| | | | | | | | |
|---|---|---|---|---|---|---|---|
| 200 | 267.45 | 277.85 | 265.49 | 300.01 | 535.99 | 315.33 | 563.39 |
| 201 | 414.1 | 209.26 | 389.63 | 447.03 | 704.17 | 533.38 | 606.64 |
| 202 | 702.54 | 622.66 | 506.76 | 887.7 | 1280.35 | 902.88 | 1236.37 |
| 203 | 562.75 | 314.93 | 512.53 | 482.74 | 699.39 | 791.42 | 899.59 |
| 204 | 176.32 | 180.1 | 192.77 | 232.45 | 379.17 | 247.14 | 362.22 |
| 205 | 629.29 | 458.8 | 613.35 | 651.07 | 1183.61 | 987.06 | 799.55 |
| 206 | 342.38 | 206.66 | 284.15 | 335.68 | 601.51 | 395.73 | 459.67 |
| 207 | 271.67 | 202.61 | 343.8 | 307.21 | 558.1 | 415.73 | 421.02 |
| 208 | 430 | 247.26 | 315.46 | 443.18 | 688.4 | 481.82 | 615.21 |
| 209 | 1559.47 | 729.14 | 1615.57 | 1698.99 | 2185.57 | 2100.15 | 2626.25 |
| 210 | 682.81 | 397.68 | 634.11 | 643.3 | 1107.61 | 940.38 | 839.18 |
| 211 | 222.23 | 162.57 | 220.06 | 269.77 | 416.59 | 274.84 | 388.42 |
| 212 | 198.65 | 151.97 | 226.1 | 213.29 | 320.21 | 308.37 | 336.35 |
| 213 | 1380.47 | 792.07 | 1290.47 | 1682.72 | 2232.77 | 1953.77 | 2138.47 |
| 214 | 372.07 | 247.11 | 335.34 | 290.23 | 459.08 | 423.98 | 642.32 |
| 215 | 566.12 | 321.59 | 390.04 | 561 | 789.62 | 590.84 | 888.3 |
| 216 | 200.62 | 121.34 | 232.22 | 226.78 | 326.33 | 286.45 | 343.48 |
| 217 | 246.19 | 144.99 | 211.15 | 234.88 | 314.82 | 301.03 | 411.93 |
| 218 | 1721.33 | 840.27 | 1669.65 | 1755.13 | 2306.27 | 2166.06 | 2773.47 |
| 219 | 704.75 | 519.05 | 747.7 | 748.74 | 1333.75 | 871.82 | 1091.69 |
| 220 | 259 | 166.63 | 282.19 | 337.55 | 408.79 | 375.26 | 479.62 |
| 221 | 762.24 | 437.4 | 762.93 | 712.17 | 1160.49 | 930.78 | 1073.37 |
| 222 | 421.07 | 252.08 | 477.89 | 578.49 | 728.91 | 622.27 | 701.27 |
| 223 | 436.26 | 347.21 | 430.15 | 467.11 | 692.96 | 626.57 | 710.07 |
| 224 | 255.08 | 191.63 | 252.08 | 299.78 | 352.3 | 389.18 | 420.82 |
| 225 | 643.97 | 457.99 | 643.94 | 704.09 | 1101.19 | 747.64 | 992.5 |
| 226 | 274.58 | 299.77 | 293.16 | 323.11 | 563.29 | 405.68 | 409.07 |
| 227 | 186.13 | 172.79 | 219.76 | 232.07 | 339.35 | 262.31 | 339.85 |
| 228 | 457.34 | 362.32 | 508.79 | 494.57 | 785.83 | 563.9 | 719.97 |
| 229 | 297.86 | 227.4 | 320.96 | 414 | 512.8 | 427.09 | 503.93 |
| 230 | 1134.57 | 717.69 | 898.31 | 1436.2 | 1584.96 | 1523.99 | 1635.62 |
| 231 | 853.21 | 716.93 | 927.26 | 1001.4 | 1324.43 | 1206.98 | 1396.24 |
| 232 | 298.82 | 166.1 | 268.38 | 265.88 | 378.11 | 395.22 | 375.85 |

FIGURE 22N

| SEQ ID | common name | description |
|---|---|---|
| 1 | Sphingosine Kinase 2 | UI-M-BH1-amu-a-08-0-UI.s1 NIH_BMAP_M_S2 Mus musculus cDNA clone UI-M-BH1-ams-a-08-0-UI.s1 3', mRNA sequence. |
| 2 | Krt1-18 | Intermediate filament protein |
| 3 | 1300007C21Rik | truncated; Mouse endogenous retrovirus truncated gag protein, complete cds, clone del env-1 3.1. |
| 4 | RIKEN cDNA 1110038L14 | vr15o06.s1 Knowles Solter mouse 2 cell Mus musculus cDNA clone IMAGE:1123570 5' similar to gb:X54942 CDK |
| 5 | Sprr1a | MSPRR1A; similar to mSPRR1A encoded by GenBank Accession Number M19868; Mus musculus SPRR1A (Sprr1a) gene |
| 6 | RIKEN cDNA 1300019K03 | UI-M-AQ1-adx-c-06-0-UI.s1 NIH_BMAP_MH3_N Mus musculus cDNA clone UI-M-AQ1-adx-c-06-0-UI.s1 3', mRNA sequence. |
| 7 | MaB-pending | vo32e09.r1 Barstead mouse irradiated colon MPLRB7 Mus musculus cDNA clone IMAGE:1061624 5', mRNA sequence. |
| 8 | MAtL | AV374591 RIKEN full-length enriched, adult male cecum Mus musculus cDNA clone 9130013H11 3', mRNA sequence. |
| 9 | Myh | Mus musculus non-muscle myosin light chain 3 (MLC3nm) mRNA, partial cds. |
| 10 | Stimulated by retinoic acid 14 | M.musculus mRNA for basic-helix-loop-helix protein. |
| 11 | ab, SCD, Scd-1 | stearoyl-CoA desaturase; Mouse stearoyl-CoA desaturase gene, exon 6. |
| 12 | Interferon-related regulator 1 | reading frame interferon beta-2; Messenger RNA fragment for mouse interferon beta (type 2) coding for the C-terminal part. |
| 13 |  | Mus musculus mRNA for BTEB-1 transcription factor. |
| 14 | Ser (or cys) proteinase inhib | Mouse RNA for plasminogen activator inhibitor 2. |
| 15 | Expressed sequence AW558171 | UI-M-BH2.3-aoa-g-07-0-UI.s1 NIH_BMAP_M_S3.3 Mus musculus cDNA clone UI-M-BH2.3-aoa-g-07-0-UI 3', mRNA seq |
| 16 |  | C78659 Mouse 3.5-dpc blastocyst cDNA Mus musculus cDNA clone J0056C12 3' similar to mouse previral retroviral insertion |
| 17 | ADAMTS-1 | putative; Mouse mRNA for secretory protein containing thrombospondin motifs, complete cds. |
| 18 | C/EBP, beta | Mouse alpha-1-acid glycoprotein (AGP1EXP1) mRNA, complete cds. |
| 19 |  | C85523 Mouse fertilized one-cell embryo cDNA Mus musculus cDNA clone J0209F01 3', mRNA sequence. |
| 20 |  | UI-M-BH2.2-aoa-b-05-0-UI.s1 NIH_BMAP_M_S3.2 Mus musculus cDNA clone UI-M-BH2.2-aoa-b-05-0-UI 2', mRNA seq |
| 21 | Nfkbi | Mus musculus I kappa B alpha gene, exons 2-6, partial cds. |
| 22 | Transketolase | Mus musculus LAF1 (transketolase) mRNA, complete cds. |
| 23 | RIKEN cDNA 1300002F13 gene | uu0bo05.x1 NCI_CGAP_Mam9 Mus musculus cDNA clone IMAGE:2649704 3', mRNA sequence. |
| 24 | MT-I, Mt-1 | Mouse gene for Metallothionein-I (three exons). |
| 25 | Cytokine ind SH2-cont protein 3 | AV374668 RIKEN full-length enriched, adult male serum Mus musculus cDNA clone 9130017A09 3' similar to U88326 |
| 26 | ab, SCD, Scd-1 | stearoyl-CoA desaturase; Mouse stearoyl-CoA desaturase gene, exon 8. |
| 27 | Ctss | Cathepsin C |
| 28 | C/EBP, delta | M.musculus mRNA for C/EBP delta. |
| 29 | Jun-B oncogene | Mus musculus transcription factor (junB) gene, 5' region and complete cds. |
| 30 | Atf3 | leucine zipper protein; Mus musculus transcription factor LRG-21 mRNA, complete cds. |
| 31 | Immediate early response, erythropoietin 1 | UI-M-BH1-amp-g-06-0-UI.s1 NIH_BMAP_M_S2 Mus musculus cDNA clone UI-M-BH1-amp-g-06-0-UI 3', mRNA sequence. |
| 32 | ADFP | Mouse adipose differentiation related protein (ADFP) mRNA, complete cds. |
| 33 | mCPE-R | Mus musculus mCPE-R mRNA for CPE-receptor, complete cds. |
| 34 | Jun-B oncogene | Mus musculus transcription factor (junB) gene, 5' region and complete cds. |
| 35 | Nr3 | Mus musculus NRL3/E4BP4 transcription factor mRNA, complete cds. |
| 36 | Sat | putative; Mouse spermidine/spermine N1-acetyltransferase (SSAT) mRNA, complete cds. |
| 37 | Cish3 | Mus musculus suppressor of cytokine signaling-3 (SOCS-3) mRNA, complete cds. |
| 38 | Antigen identified by mAb KI 67 | M.musculus mRNA for Ki-67. |
| 39 | Expressed sequence C77826 | UI-M-BH2.3-aox-b-05-0-UI.s1 NIH_BMAP_M_S3.2 Mus musculus cDNA clone UI-M-BH2.2-aox-b-05-0-UI 3', mRNA seq |
| 40 | Nuclear factor of kappa light chain gene enhancer in B-cells inhibitor, alpha | ub75c05.x1 Soares_mammary_gland_NMLMG Mus musculus cDNA clone IMAGE:1383637 3' similar to gb:M69043. |

FIGURE 22O

| # | Gene | Description |
|---|---|---|
| 41 | HB-EGF | Mus musculus (clone lambda mouse 1) heparin-binding EGF-like growth factor precursor mRNA, complete cds. |
| 42 | pgk1 | Mus musculus X chromosome-linked phosphoglycerate kinase (pgk-1) mRNA, complete cds. |
| 43 | RIKEN cDNA 5033417E09 gene | ud81111.x1 Sugano mouse liver mRNA Mus musculus cDNA clone IMAGE:1450413 3' similar to gb:L32179 |
| 44 | Pyruvate dehydrogenase kinase 4 | Mus musculus mRNA for pyruvate dehydrogenase kinase-like protein. |
| 45 | Leukemia-associated gene | UI-M-AL0-abv-e-12-0-UI.s1 NIH_BMAP_AL0 Mus musculus cDNA clone UI-M-AL0-abv-e-12-0-UI 3', mRNA sequence. |
| 46 | Claudin 1 | Integral membrane protein localizing at tight junctions; Mus musculus claudin-1 mRNA, complete cds. |
| 47 | Potassium inwardly-rectifying channel, subfamily J, member 12 | M.musculus MB-IRK2 mRNA. |
| 48 | RIKEN cDNA 1110032C13 gene | UI-M-AP1-agn-a-04-0-UI.s1 NIH_BMAP_MST_N Mus musculus cDNA clone UI-M-AP1-agn-a-04-0-UI 3', mRNA sequence. |
| 49 | Thyroid hormone receptor alpha | Mus musculus orphan nuclear receptor Rev-Erb-beta mRNA, partial cds. |
| 50 | Proteasome (prosome, macropain) subunit, beta type 8 (large multifunctional protease 7) | Lmp7k, s, l allele; Mus musculus 20S proteasome subunit Lmp7 (Lmp7k, s, l allele) mRNA, complete cds. |
| 51 | aldh3 | Mus musculus aldehyde dehydrogenase 3 (aldh3) gene, partial cds. |
| 52 | Butyrate response factor 2 | vm6456.s1 Soares_mammary_gland_NMLMG Mus musculus cDNA clone IMAGE:1246555 3', mRNA sequence. |
| 53 | TSA-1 | Mus musculus thymic shared antigen-1 (TSA-1) gene, complete cds. |
| 54 | c-myc | Mouse c-myc gene exon 1. |
| 55 | MMSTK1 | putative serine/threonine kinase; Mouse mRNA for STK-1 (serine/threonine kinase), complete cds. |
| 56 | EIF 1A | translation initiation factor; Mus musculus eIF-1A (eIF-1A) mRNA, complete cds. |
| 57 | GRO1 oncogene | secretory protein KC precursor; Mouse platelet-derived growth factor-inducible KC protein mRNA, complete cds. |
| 58 | IGF binding protein 2 | M.musculus mRNA for insulin-like growth factor binding protein-2. |
| 59 | Expressed sequence AI314858 | uj3107.x1 Sugano mouse kidney mRNA Mus musculus cDNA clone IMAGE:1921861 3', mRNA sequence. |
| 60 | Mcm3 | Mus musculus 14-3-3 protein sigma mRNA, complete cds. |
| 61 |  | UI-M-BH1-ald-c-09-0-UI.s1 NIH_BMAP_M_S2 Mus musculus cDNA clone UI-M-BH1-ald-c-09-0-UI 3', mRNA sequence. |
| 62 | Kruppel-like factor 9 | UI-M-AH1-agp-g-10-0-UI.s1 NIH_BMAP_MCE_N Mus musculus cDNA clone UI-M-AH1-agp-g-10-0-UI 3', mRNA sequence. |
| 63 | FGF binding protein 1 | heparin and fibroblast growth factor binding; similar to Homo sapiens HBp17 protein encoded by seq in AN M60047; FGFBP-1 |
| 64 | Period homolog (Drosophila) | circadian pacemaker protein; Mus musculus Rigui mRNA, complete cds. |
| 65 | TGFB induc. early growth resp. | zinc finger protein; Mus musculus transcription factor GIF mRNA, complete cds. |
| 66 | RIKEN cDNA 4930465J02 gene | u21104.y1 Sugano mouse embryo mRNA Mus musculus cDNA clone IMAGE:2086223 5' sim to SW:Y733K_HUMAN Q04323 |
| 67 | RIKEN cDNA 1300002F13 gene | UI-M-BH0-ajd-f-01-0-UI.s1 NIH_BMAP_M_61 Mus musculus cDNA clone UI-M-BH0-ajd-f-01-0-UI 3', mRNA sequence. |
| 68 | Zinc finger protein 36 | TIS11 (AA 1 - 183); Mouse TPA-induced TIS11 mRNA. |
| 69 | RIKEN cDNA 1190002H23 gene | UI-M-BG1-ac-e-02-0-UI.s1 NIH_BMAP_MSC_N Mus musculus cDNA clone UI-M-BG1-ac-e-02-0-UI 3', mRNA sequence. |
| 70 | High mobility group box 2 | M.musculus mRNA for high mobility group 2 protein. |
| 71 | Metallothionein 2 | metallothionein II; Mouse metallothionein II (MT-II) gene. |
| 72 | Myd118 | Myd118 protein (AA 1-857); Mouse myeloid differentiation primary response mRNA encoding Myd118 protein. |
| 73 | CDK inhibitor 1A (P21) | UI-M-BH1-amc-d-08-0-UI.s1 NIH_BMAP_M_62 Mus musculus C57BL/6J Mus musculus cDNA clone UI-M-BH1-amc-d-08-0-UI 3', mRNA sequence. |
| 74 | Stromal cell derived factor 1 | AV196913 Mus musculus C57BL/6J 10-11 day embryo Mus musculus cDNA clone 2610055D15, mRNA sequence. |
| 75 | Cyr61 | Cyr61 product; Mouse Cyr61 mRNA, complete cds. |
| 76 | RIKEN cDNA 1600029D21 gene | uc30b06.r1 Soares_mammary_gland_NMMG Mus musculus cDNA clone IMAGE:1389479 5', mRNA sequence. |
| 77 | Purine-nucleoside phosphorylase | Mus musculus purine nucleoside phosphorylase (Np-b) mRNA, complete cds. |
| 78 | BAR, B2AR, ADRBR, ADRB2R | Mouse gene for beta-2-adrenergic receptor. |
| 79 | RIKEN cDNA 2310076D10 gene | UI-M-AH1-agw-h-03-0-UI.s1 NIH_BMAP_MCE_N Mus musculus cDNA clone UI-M-AH1-agw-h-03-0-UI 3', mRNA sequence. |
| 80 | Paired-like homeodomain TF 2 | bicoid-related homeodomain protein; murine homolog of Rieger syndrome; mouse bicoid-rel homeodomain pret eukaryotic (Rigs) |
| 81 | Keratin complex 1, acidic, gene 17 | epidermal keratin type I; Mouse type I epidermal keratin mRNA, clone pkSCC-50, 3' end. |

FIGURE 22P

| | | |
|---|---|---|
| 82 | Growth arrest and DNA-damage-inducible 45 beta | AV136793 Mus musculus C57BL/6J 10-11 day embryo Mus musculus cDNA clone 2810046L02, mRNA sequence. |
| 83 | Rrm1 | ribonucleotide reductase subunit M1; Mouse ribonucleotide reductase subunit M1 mRNA, complete cds. |
| 84 | Ncl | Mouse nucleolin gene. |
| 85 | PCNA | Murine PCNA gene for proliferating cell nuclear antigen (DNA polymerase delta auxiliary protein). |
| 86 | H-2T17 | MHC H2-TL-T17-c; Mouse MHC class I H2-TL-T17-c mRNA (d haplotype), complete cds. |
| 87 | Expressed sequence AI467657 | vl37g06.y1 Soares mouse NbMH Mus musculus cDNA clone IMAGE:846010 5' similar to SW:PLZF_HUMAN Q05516 |
| 88 | Nr4a1 | Mouse N10 gene for a nuclear hormonal binding receptor. |
| 89 | Lectin, galactose binding, sol 7 | Mus musculus galectin-7 mRNA, complete cds. |
| 90 | HK1 | Mus musculus gene for hexokinase I, exon 1 (and joined CDS). |
| 91 | Sequestosome 1 | similar to D. melanogaster Rall(2)Pp protein; Mus musculus oxidative stress-induced protein mRNA, complete cds. |
| 92 | Mcm5, Cdc46, mCDC46 | pu1, mouse homolog of yeast CDC46; Mouse mRNA for mCDC46 protein, complete cds. |
| 93 | DNA segment, Chr 12, WSU 123, eu20l08.y1 Sugano mouse embryo mewa Mus musculus cDNA clone IMAGE:2088191 5' similar to SW:YBC4_YEAST P38205 |
| 94 | | Mouse Histone H2A1 gene, complete cds. |
| 95 | RIKEN cDNA 3110004P22 gene | UI-M-BG0-ahi-e-11-0-UI.s1 NIH_BMAP_NSC Mus musculus cDNA clone UI-M-BG0-ahi-e-11-0-UI 3', mRNA sequence. |
| 96 | Expressed sequences AU018108 | vo73e09.r1 Barstead mouse myotubes MPLRB6 Mus musculus cDNA clone IMAGE:1094776 5', mRNA sequence. |
| 97 | Kruppel-like factor 13 | UI-M-BH2.2-agf-f-06-0-UI.s1 NIH_BMAP_M_S3.2 Mus musculus cDNA clone UI-M-BH2.2-agf-f-08-0-UI 3', mRNA sequence. |
| 98 | E26 avian leuk oncogen 2, 3' dom | ets2 protein; Mouse erythroblastosis virus oncogene homolog 2 (ets-2) mRNA, complete cds. |
| 99 | H2-Q6 | Mouse Q6/9d gene. |
| 100 | TACSTD 2 | vz06f08.x1 Soares_mammary_gland_NbMMG Mus musculus cDNA clone IMAGE:13148971 3' similar to gb:J04152_rn1 |
| 101 | Fra1 | Fra-1; B-Zip transcription factor; subunit of AP-1 member of the Fos family; Mus musculus fos-related antigen 1 (fra-1) gene |
| 102 | Immediate early response 3 | M.musculus pyg5 mRNA. |
| 103 | TGFB inducible early growth resp | zinc finger protein; Mus musculus transcription factor GIF mRNA, complete cds. |
| 104 | RIKEN cDNA 5730403B10 gene | UI-M-AK1-aes-b-10-0-UI.s1 NIH_BMAP_MHY_N Mus musculus cDNA clone UI-M-AK1-aes-b-10-0-UI 3', mRNA sequence. |
| 105 | Pre B-cell leukemia TF 1 | UI-M-BH2.1-apu-g-09-0-UI.s1 NIH_BMAP_M_S9.1 Mus musculus cDNA clone UI-M-BH2.1-apu-g-09-0-UI 3', mRNA seq |
| 106 | MHC Q2-k | Mouse MHC (Ca) Q2-k gene for class I antigen, exons 1-3. |
| 107 | | MHC beta-2-microglobulin; Mouse MHC class I Q4 beta-2-microglobulin (Qb-1) gene, complete cds. |
| 108 | RIKEN cDNA 2810484M10 gene | UI-M-BH2.1-aph-h-08-0-UI.s1 NIH_BMAP_M_S3.1 Mus musculus cDNA clone UI-M-BH2.1-aph-h-08-0-UI 3', mRNA seq |
| 109 | Irs-2 | Mus musculus insulin receptor substrate-2 (Irs2) gene, partial cds. |
| 110 | Thra | UI-M-AM1-afv-b-06-0-UI.s1 NIH_BMAP_MAM_N Mus musculus cDNA clone UI-M-AM1-afv-b-06-0-UI 3', mRNA sequence. |
| 111 | DNA segment, Chr 19, ERATO Doi 412, expressed | UI-M-BH0-alxh-e-08-0-UI.s1 NIH_BMAP_BH0 Mus musculus cDNA clone UI-M-BH0-akh-e-08-0-UI 3', mRNA sequence. |
| 112 | RIKEN cDNA 2700038D15 gene | UI-M-BH1-ame-a-04-0-UI.s1 NIH_BMAP_M_S2 Mus musculus cDNA clone UI-M-BH1-ame-a-04-0-UI 3', mRNA sequence. |
| 113 | Eph receptor B4 | Mus musculus Bsrk/c eph-related receptor protein tyrosine kinase mRNA, complete cds. |
| 114 | Secreted modular calcium-binding p us21a05.r1 Soares_mammary_gland_NbMMG Mus musculus cDNA clone IMAGE:1348304 5', mRNA sequence. |
| 115 | RIKEN cDNA 2610008O03 gene | UI-M-AK1-aet-h-03-0-UI.s1 NIH_BMAP_MHY_N Mus musculus cDNA clone UI-M-AK1-aet-h-03-0-UI 3', mRNA sequence. |
| 116 | Crystalin B | also known as alstatin B; Mus musculus crystalin B (Stlb) gene, complete cds. |
| 117 | Expressed sequence AA081138 | ud90d03.r1 Soares_NMPu Mus musculus cDNA clone IMAGE:1478405 5', mRNA sequence. |
| 118 | RIKEN cDNA 5730469M10 gene | UI-M-BG0-aie-g-01-0-UI.s1 NIH_BMAP_MSC Mus musculus cDNA clone UI-M-BG0-aie-g-01-0-UI 3', mRNA sequence. |
| 119 | Hydroxysteroid (17-beta) dehyd 12 | Mus musculus putative steroid dehydrogenase (KIK-I) mRNA, complete cds. |
| 120 | Expressed sequence AU044290 | UI-M-AK1-aes-e-01-0-UI.s1 NIH_BMAP_MHY_N Mus musculus cDNA clone UI-M-AK1-aes-e-01-0-UI 3', mRNA sequence. |
| 121 | WSB-1 | Mus musculus WSB-1 mRNA, complete cds. |

FIGURE 22Q

| # | Gene | Description |
|---|---|---|
| 122 | Supp of initiator codon mutations, related sequence 1 (S. cerevisiae) | homolog of human sui1like1, yeast sui1 and rice gos2; M.musculus mRNA for Sui1. |
| 123 | B-cell receptor-associated prot 37 | M.musculus mRNA for B-cell receptor associated protein (BAP) 37. |
| 124 | NM 2 protein (NM238) (nucleoside diphosphate kinase) | M.musculus mRNA for nucleoside diphosphate kinase B. |
| 125 | Solute carrier family 25 (mitochondrial carrier; ANT), member 5 | mj83h01.r1 Soares mouse p3NMF19.5 Mus musculus cDNA clone IMAGE:492737 5' similar to gb:J02683 ADP,ATP CARRIER PROTEIN, FIBROBLAST ISOFORM (HUMAN); gb:X70847 M.musculus mRNA for adenine nucleotide translocase vv19g10.y1 Soares_mammary_gland_NbMMG Mus musculus cDNA clone IMAGE:1244322 5' sim to SW:ZAN_PIG C28993 |
| 126 | PI3Kr1 | PI3K regulatory subunit; Mus musculus phosphoinositide 3-kinase regulatory subunit, p85alpha mRNA, complete cds. |
| 127 | RIKEN cDNA 5330577E15 gene | UI-M-BH1-aml-l-05-0-UI.s2 NIH_BMAP_M_S2 Mus musculus cDNA clone UI-M-BH1-aml-l-05-0-UI 3', mRNA sequence. |
| 128 | TGF-beta 1 induced transcript 4 | M.musculus TSC-22 mRNA. |
| 129 | ABS, subfamily B (MDR/TAP), member 2 | Mus musculus antigen processing-associated transporter TAP1-g7 mRNA, complete cds. |
| 130 | Ran | Mouse (clone M2) GTPase (Ran) mRNA, complete cds. |
| 131 | Peroxisomal delta3, delta2-ECI | UI-M-AH0-acu-e-04-0-UI.s1 NIH_BMAP_MCE Mmr musculus cDNA clone UI-M-AH0-acu-e-04-0-UI 3', mRNA sequence. |
| 132 | tbm3 | Mus musculus (bm3 mRNA, complete cds. |
| 133 | DNA segment, Chr 10, ERATO Doi 214, expressed | UI-M-AH1-ags-l-11-0-UI.s1 NIH_BMAP_MCE_N Mus musculus cDNA clone UI-M-AH1-ags-l-11-0-UI 3', mRNA sequence. |
| 134 | Keratin complex 1, acidic, gen 19 | AU040593 Mouse four-cell-embryo cDNA Mus musculus cDNA clone J0812H07 3', mRNA sequence. |
| 135 | TG interacting factor | M.musculus mRNA for mTGIF protein. |
| 136 | RIKEN cDNA 1110004C05 gene | UI-M-BH2.3-aqh-o-06-0-UI.s1 NIH_BMAP_M_S3.3 Mus musculus cDNA clone UI-M-BH2.3-aqh-o-06-0-UI 3', mRNA seq. |
| 137 | | histone H2B-291A (AA 1 - 125); histone H2A-291.A (AA 1 - 136); Mouse H2B and H2A histone genes (291A). |
| 138 | SGK | UI-M-BH1-akw-d-06-0-UI.s1 NIH_BMAP_M_S2 Mus musculus cDNA clone UI-M-BH1-akw-d-06-0-UI 3', mRNA sequence. |
| 139 | BMAP 2 | Mus musculus endothelial-monocyte activating polypeptide II mRNA, complete cds. |
| 140 | Actin related protein 2/3 complex, subunit 1B (41 kDa) | uc69e09.x1 NCI_CGAP_Mam1 Mus musculus cDNA clone IMAGE:2847528 3', mRNA sequence. |
| 141 | Expressed sequence AA536946 | UI-M-AK1-aaz-g-04-0-UI.s1 NIH_BMAP_MHY_N Mus musculus cDNA clone UI-M-AK1-aaz-g-04-0-UI 3', mRNA sequence. |
| 142 | Solute carrier family 2 (GLUT), mem | facilitated glucose transporter; Mouse facilitated glucose transport protein mRNA, complete cds. |
| 143 | Ornithine aminotransferase | M.musculus Oat mRNA for ornithine aminotransferase. |
| 144 | GST omega 1 | UI-M-AK1-aas-l-05-0-UI.s1 NIH_BMAP_MHY_N Mus musculus cDNA clone UI-M-AK1-aas-l-05-0-UI 3', mRNA sequence. |
| 145 | | UI-M-AK0-acb-e-02-0-UI.s1 NIH_BMAP_MHY Mus musculus cDNA clone UI-M-AK0-acb-e-02-0-UI 3', mRNA sequence. |
| 146 | B-cell leukemia/lymphoma 8 | homolog of human oncogene, BCL-8; Mus musculus BCL-8 mRNA, complete cds. |
| 147 | H2A Histone family, member Z | histone H2A.Z; Mus musculus histone H2A.Z (H2A.Z) mRNA, complete cds. |
| 148 | mrc2, Hsc74, Hsp74, Hsp74, mortalin | Mouse gene for mitochondrial stress-70 protein (PBP74/GSA), exon 14,15,16 and 17. |
| 149 | Fosb | fosB protein (AA 1-338); Mouse fosB mRNA. |
| 150 | B-cell leukemia/lymphoma 10 | Mus musculus mRNA for bcl-10 protein. |
| 151 | HMG nucleosomal binding dom 2 | HMG-17 protein (AA 1 - 89); Mouse mRNA for HMG-17 chromosomal protein. |
| 152 | EIF 3, subunit 8 (110 kDa) | UI-M-BH1-arw-c-09-0-UI.s1 NIH_BMAP_M_S2 Mus musculus cDNA clone UI-M-BH1-arw-c-09-0-UI 3', mRNA sequence. |
| 153 | | similar to yeast NIP1 nuclear import protein; transmembrane protein; contains several potential phosphorylation sites for PKC and casein kinase II; Mus musculus NIP-like protein (NIP(L)(A3)) mRNA, complete cds. |
| 154 | Claudin 1 | vc68a08.x1 Stratagene mouse skin (#937313) Mus musculus cDNA clone IMAGE:1227536 3', mRNA sequence. |
| 155 | RIKEN cDNA 2900010105 gene | UI-M-BG0-aha-b-12-0-UI.s1 NIH_BMAP_MSC Mus musculus cDNA clone UI-M-BG0-aha-b-12-0-UI 3', mRNA sequence. |

FIGURE 22R

| # | Name | Description |
|---|---|---|
| 157 | RIKEN cDNA 2310008N12 gene | UI-M-BH1-alk-c-06-0-UI.s1 NIH_BMAP_M_S2 Mus musculus cDNA clone UI-M-BH1-alk-c-06-0-UI 3', mRNA sequence. |
| 158 | Fatty acid Coenzyme A ligase, long chain 5 | UI-M-APO-abj-g-11-0-UI.s1 NIH_BMAP_MST Mus musculus cDNA clone UI-M-APO-abj-g-11-0-UI 3', mRNA sequence. |
| 159 | RIKEN cDNA 1810015C04 gene | UI-M-BH2.1-apa-d-07-0-UI.s1 NIH_BMAP_M_S3.1 Mus musculus cDNA clone UI-M-BH2.1-apa-d-07-0-UI 3', mRNA seq |
| 160 | Ier2 | Mouse growth factor-inducible protein (pip92) mRNA, complete cds. |
| 161 | Keratin complex 1, acidic, gene 17 | epidermal keratin type I; Mouse type I epidermal keratin mRNA, clone pKSCC-50, 3' end. |
| 162 | DNA segment, Chr 6, ERATO Doi 108, expressed | UI-M-AO1-aag-h-09-0-UI.s1 NIH_BMAP_MPG_N Mus musculus cDNA clone UI-M-AO1-aag-h-09-0-UI 3', mRNA sequence. |
| 163 | Cytochr c oxidase, subunit Vb | cytochrome c oxidase subunit Vb precursor; Mouse mRNA for mitochondrial cytochrome c oxidase subunit Vb. |
| 164 | Atf3 | leucine zipper protein; Mus musculus transcription factor LRG-21 mRNA, complete cds. |
| 165 | Zinc finger protein 216 | Mus musculus zinc finger protein ZNF216 mRNA, complete cds. |
| 166 | Solute carrier family 25 (mitochondrial carrier; ANT), member 5 | Mus musculus adenine nucleotide translocase mRNA, complete cds. |
| 167 | Epha2 | similar to human eck gene product; Swiss-Prot Accession Number P29317; Mus musculus receptor-protein tyrosine kinase (eck) |
| 168 | Tubb5 | beta-tubulin (AA 1-444) (79 is 1st base in codon); Mouse mRNA for beta-tubulin (isotype Mbeta 5). |
| 169 | Carboxypeptidase E | Mouse mRNA for carboxypeptidase H. |
| 170 | Solute carrier family 3 (activators of dibasic and neutral AA transport), member 2 | 4F2 heavy chain (AA 1-526); Murine mRNA for 4F2 antigen heavy chain. |
| 171 | FGF inducible 14 | Mus musculus fibroblast growth factor inducible gene 14 (FIN14) mRNA, complete cds. |
| 172 | Kcn6 | Mus musculus G-protein coupled inwardly rectifying K+ channel (GirK2D) mRNA (b haplotype), complete cds. |
| 173 | Peroxiredoxin 5, related seq 3 | CP-2; Mus musculus 1-Cys peroxiredoxin protein 2 gene, complete cds. |
| 174 | Ldr | Low density lipoprotein receptor |
| 175 | Scin | gelsolin-like protein; Mus musculus ADSEVERIN mRNA, complete cds. |
| 176 | H-2T10 | MHC H2-TL.T10-129; Mouse MHC class I H2-TL.T10-129 mRNA (b haplotype), complete cds. |
| 177 | Expressed sequence C85189 | UI-M-BH2.3-aqj-d-12-0-UI.s1 NIH_BMAP_M_S3.3 Mus musculus cDNA clone UI-M-BH2.3-aqj-d-12-0-UI 2', mRNA sequence. |
| 178 | LPS-induced TNF-alpha factor | UI-M-BH0-atb-l-10-0-UI.s1 NIH_BMAP_M_S3.1 Mus musculus cDNA clone UI-M-BH0-atb-l-10-0-UI 3', mRNA sequence. |
| 179 | NRF2 | CNC basic leucine zipper DNA binding protein; Mus musculus p45 NF-E2 related factor 2 (NRF2) gene |
| 180 | HS 10 kDa protein 1 (chaperonin 10) | heat shock protein 10, HSP10; Mus musculus chaperonin 10 mRNA, complete cds. |
| 181 | Midnolin | UI-M-BH2.1-aga-h-06-0-UI.s1 NIH_BMAP_M_S3.1 Mus musculus cDNA clone UI-M-BH2.1-aga-h-06-0-UI 3', mRNA sequence. |
| 182 | Cops6 | similar to human Vpr interacting protein (hVIP) ; 34 kDa human MOV34 isologue; subunit 6 is a 36 kDa component of the COP9 complex which contains a total of 8 distinct subunits, similar to the JAB1-containing signalsome; mouse COPS6 mRNA |
| 183 | | partial homology to cytochrome C oxidase subunit VII; M.musculus mRNA for cytochrome C oxidase subunit VII homologue. |
| 184 | Slits-induced gene 81 | Mus musculus mRNA, one isoform of PTP-RL9. |
| 185 | PTP, receptor type, J | M.musculus big1 mRNA. |
| 186 | Big1 | |
| 187 | EIF factor 5a | UI-M-AH0-acw-e-01-0-UI.s1 NIH_BMAP_MCE Mus musculus cDNA clone UI-M-AH0-acw-e-01-0-UI 3', mRNA sequence. |
| 188 | RIKEN cDNA 2010320B17 gene | UI-M-BH2.1-apy-g-01-0-UI.s1 NIH_BMAP_M_S3.1 Mus musculus cDNA clone UI-M-BH2.1-apy-g-01-0-UI 3', mRNA sequence. |
| 189 | RIKEN cDNA 2810103L08 gene | UI-M-BH2.1-apm-e-09-0-UI.s1 NIH_BMAP_M_S3.1 Mus musculus cDNA clone UI-M-BH2.1-apm-e-09-0-UI 3', mRNA sequence. |
| 190 | RIKEN cDNA 0810010M09 gene | UI-M-AI0-asq-s-05-0-UI.s1 NIH_BMAP_MBS Mus musculus cDNA clone UI-M-AI0-asq-s-05-0-UI 3', mRNA sequence. |
| 191 | Heat shock protein, 60 kDa | HSP60 protein (555 AA); Mouse mRNA for HSP60 protein (clone 3T3-7, -9, and -M1). |
| 192 | Gapd | glyceraldehyde-3-phosphate dehydrogenase; Mouse glyceraldehyde-3-phosphate dehydrogenase mRNA, complete cds. |
| 193 | Protein tyrosine phosphatase 4a2 | potentially prenylated protein tyrosine phosphatase; Mus musculus potentially prenylated protein tyrosine phosphatase mPRL-2 |

FIGURE 22S

| | | |
|---|---|---|
| 195 | gene 37 | Murine gene 37 for pot. membrane bound protein. |
| 196 | RIKEN cDNA 1110032G10 gene | UI-M-BH2.2-aqh-b-08-0-UI.s1 NIH_BMAP_M_S3.3 Mus musculus cDNA clone UI-M-BH2.3-aqh-b-05-0-UI 3', mRNA sequence. |
| 197 | Isocitrate dehydrogenase 3 (NAD+), gamma | Mus musculus NAD(H)-specific isocitrate dehydrogenase gamma subunit precursor, mRNA, complete cds. |
| 198 | RIKEN cDNA 1110021D01 gene | UI-M-BH2.1-apy-h-02-0-UI.s1 NIH_BMAP_M_S3.1 Mus musculus cDNA clone UI-M-BH2.1-apy-h-02-0-UI 3', mRNA sequence. |
| 199 | Carboxypeptidase E | Mouse mRNA for carboxypeptidase H. |
| 200 | Cpe | |
| 201 | Slc39A4 | Mouse mRNA for Sid39Ap, complete cds. |
| 202 | Protein tyrosine phosphatase 4a1 | Mus musculus mRNA for coproporphyrinogen oxidase, complete cds. |
| 203 | mcEPB | Mus musculus protein tyrosine phosphatase (PRL-1) mRNA, complete cds. |
| 204 | Zinc finger protein 38 | Mouse CC/AAT/enhancer binding protein gene, complete cds. |
| 205 | mATF4 | MTA.G11.085.A MTA adult mouse thymus library Mus musculus cDNA clone MTA.G11.085 5' end similar to xenopus XCAP-C murine homolog of TAX1EB67/ATF4; M.musculus mATF4 (mTR67) mRNA, complete cds. |
| 206 | NADH dehydrogenase (ubiquinone) flavoprotein 2 | UI-M-AP1-agg-c-11-0-UI.s1 NIH_BMAP_MST_N Mus musculus cDNA clone UI-M-AP1-agg-c-11-0-UI 3', mRNA sequence. |
| 207 | Expressed sequence AA430822 | UI-M-BH3-ajl-f-03-0-UI.s1 NIH_BMAP_M_S1 Mus musculus cDNA clone UI-M-BH3-ajl-f-03-0-UI 3', mRNA sequence. |
| 208 | Inosine 5'-phosphate dehydrog 2 | IMP dehydrogenase (EC 1.2.1.14); Mouse IMP dehydrogenase mRNA, complete cds. |
| 209 | | MHC Q4 class I antigen (31 AA) (119 is 2nd base in codon); Protein sequence is in conflict with the conceptual translation; Mouse Q4 class I MHC gene (exon 6). |
| 210 | Aquaporin 2 | vz26d10.r1 GueyWoodford Balbc mouse kidney day 7 Mus musculus cDNA clone IMAGE:732498 3', mRNA sequence. |
| 211 | Expressed sequence AA987150 | UI-M-AC0-acs-e-08-0-UI.s1 NIH_BMAP_MPO Mus musculus cDNA clone UI-M-AC0-acb-a-08-0-UI 3', mRNA sequence. |
| 212 | Expressed sequence C76356 | UI-M-A31-agv-b-09-0-UI.s1 NIH_BMAP_MOB_N Mus musculus cDNA clone UI-M-AJ1-agv-b-09-0-UI 3', mRNA sequence. |
| 213 | Histh | Mouse Histone H3 (H3.2-221) gene, complete cds. |
| 214 | Enolase 1, alpha non-neuron | UI-M-AM0-adv-h-04-0-UI.s1 NIH_BMAP_MAM Mus musculus cDNA clone UI-M-AM0-adv-h-04-0-UI 3', mRNA sequence. |
| 215 | EIf4 | unidentified reading frame, put. eIF-4A (aa 1-380); put. altern. eIF-4A (aa 1-370); Mouse mRNA for initiation factor eIF-4AI. |
| 216 | TGF beta regulated gene 1 | UI-M-BH1-enm-f-07-0-UI.s1 NIH_BMAP_M_S2 Mus musculus cDNA clone UI-M-BH1-enm-f-07-0-UI 3', mRNA sequence. |
| 217 | D6Eid109e | Mus musculus mRNA for eRF1, partial cds. |
| 218 | Histocompatibility 2, L region | ub6g12.r1 Soares_thymus_2NbMT Mus musculus cDNA clone IMAGE:1396142 5' similar to gb:X01752_mat |
| 219 | Aldolase 1, A isoform | aldolase A; Mouse mRNA for aldolase A. |
| 220 | | vr20d10.r1 Barstead mouse myotubes MPLRB5 Mus musculus cDNA clone MPLRB5 Mus musculus cDNA clone 3' similar to A. |
| 221 | Apoe1 | Source: M.musculus Apoe1 gene, exons 1 to 3 and complete CDS. |
| 222 | Tripartite motif protein 28 | M.musculus mRNA for TIF1 beta protein. |
| 223 | Ethanol induced 6 | UI-M-AK1-aeu-f-09-0-UI.s1 NIH_BMAP_MHY_N Mus musculus cDNA clone UI-M-AK1-aeu-f-09-0-UI 3', mRNA sequence. |
| 224 | CDC 2 homolog A (S. pombe) | Mouse cell cycle protein (p34 CDC2) mRNA, complete cds. |
| 225 | Basic transcription factor 3 | UI-M-BH2.1-apb-b-08-0-UI.s1 NIH_BMAP_M_S3.1 Mus musculus cDNA clone UI-M-BH2.1-apb-b-08-0-UI 3', mRNA sequence. |
| 226 | MAP kinase 6 | UI-M-AH1-aqx-b-09-0-UI.s1 NIH_BMAP_MCE_N Mus musculus cDNA clone UI-M-AH1-aqx-b-09-0-UI 3', mRNA sequence. |
| 227 | Expressed sequence C81323 | vz4fh05.r1 Soares_thymus_2NbMT Mus musculus cDNA clone IMAGE:1229753 5' similar to SW:SSRP_MOUSE CD6943 |
| 228 | Ck | Mouse serine threonine tyrosine kinase (STY) mRNA, complete cds. |
| 229 | RHOA | RHOA; Mus musculus Rho family GTPase (ArhA) mRNA, complete cds. |
| 230 | Aha2 | M.domesticus (CD-1) mRNA for histone H3 (partial). |
| 231 | Histone gene complex 1 | Mus musculus GP108 mRNA, complete cds. |
| 232 | RIKEN cDNA 1300019P08 gene | AV215217 RIKEN full-length enriched, adult male hippocampus Mus musculus cDNA clone 2900087J21 3' similar to L12018 |

US 8,252,749 B2

METHODS, KITS, AND COMPOSITIONS FOR GENERATING NEW HAIR FOLLICLES AND GROWING HAIR

CROSS-REFERENCE TO RELATED APPLICATIONS

This application is the U.S. National Stage of International Application No. PCT/US2007/020842, filed Sep. 27, 2007, which in turn, claims the benefit of U.S. Provisional Application No. 60/847,854, filed Sep. 28, 2006, each of which is incorporated by reference.

STATEMENT UNDER 35 U.S.C. §103(c)(2)(C)

The claimed invention was made as a result of activities undertaken within the scope of a joint research agreement between the Trustees of the University of Pennsylvania and Follica, Inc.

BACKGROUND OF THE INVENTION

The invention relates to methods, kits, and compositions for generating new hair follicles and growing hair on a subject.

Follicular neogenesis is defined as the generation of new hair follicles (HF) after birth. Humans are born with a full complement of HF, which can change in size and growth characteristics as in early baldness or can ultimately degenerate and disappear as in the late stages of baldness or in permanent scarring (cicatricial) alopecias. Therefore, the generation of new HF is desirable in the treatment of common baldness as well as less common hair loss conditions, such as discoid lupus erythematosus, congenital hypotrichosis, lichen planopilaris, and other scarring alopecias.

SUMMARY OF THE INVENTION

The invention features methods, kits, and compositions for generating new hair follicles and growing hair on a subject.

In one aspect, the invention features a composition including from 0.001% to 0.1% (w/v) of a small molecule EGFR inhibitor formulated for topical administration, wherein the EGFR inhibitor is a non-naturally occurring nitrogen-including heterocycle of less than about 2,000 daltons, or a metabolite thereof.

In another aspect, the invention features a kit including (i) a composition including from 0.000001% to 10% (w/v) of a small molecule EGFR inhibitor formulated for topical administration, wherein the EGFR inhibitor is a non-naturally occurring nitrogen-including heterocycle of less than about 2,000 daltons, or a metabolite thereof, and (ii) instructions for applying this composition to the skin of a subject in need of generating a hair follicle or stimulating a hair growth.

The invention further features a kit including (i) a composition of the invention and (ii) instructions for applying the composition to the skin of a subject.

The invention also features a kit including (i) a composition of the invention; and (ii) instructions for applying the composition to the skin of a subject in need of generating a hair follicle or stimulating a hair growth.

The invention features a kit including (i) a composition of the invention; and (ii) instructions for administration of the composition to the skin of a subject, wherein the skin has undergone reepithelialization less than two weeks prior to the first administration of the composition.

The invention features a kit including (i) a composition comprising an EGFR antibody; and (ii) instructions for administering the antibody to a subject in need of generating a hair follicle or stimulating a hair growth. In one embodiment, the antibody is selected from zalutumumab, cetuximab, IMC 11F8, matuzumab, SC 100, ALT 110, PX 1032, BMS599626, MDX 214, and PX 1041.

The invention further features a kit including a composition formulated for topical administration including (i) a small molecule EGFR inhibitor selected from leflunomide, gefitinib, erlotinib, lapatinib, canertinib, vandetanib, CL-387785, PKI166, pelitinib, HKI-272, and HKI-357; and (ii) an additional biologically active agent selected from an antihistamine, an anti-inflammatory, a retinoid, an anti-androgen, an immunosuppressant, a channel opener, an antibiotic, and an antimicrobial. In one embodiment, the small molecule EGFR inhibitor is gefitinib or erlotinib and the additional biologically active agent is a channel opener selected from minoxidil, diazoxide, and phenyloin.

Any of the above kits can optionally include instructions for applying the composition to the head of a subject (e.g., to the scalp, cheek, chin, lower face, or eyebrow), for applying the composition to the skin of a subject once or twice daily, for applying the composition to the skin of a subject for at least 2, 3, 4, 5, 6, 7, 8, 9, or even 10 consecutive days, for administering the composition during the night, or administering the composition during the day.

The invention features a method for generating a hair follicle or stimulating a hair growth on the skin of a subject by (i) disrupting the skin of the subject (for example, resulting in the induction of reepithelialization of the skin of the subject) and (ii) contacting the cells of the skin with a small molecule EGFR inhibitor, or a metabolite thereof, in an amount sufficient to generate hair follicles or stimulate hair growth on the skin. In certain embodiments, step (a) is performed less than two weeks, 10 days, 8 days, 5 days, or even 3 days prior to step (b). In other embodiments, step (a) is performed simultaneous with, or more than one day, two days, 3 days or one week after step (b).

The invention further features a method for generating a hair follicle or stimulating a hair growth on the skin of the head of a subject by (i) contacting the cells of the skin with a small molecule EGFR inhibitor, or a metabolite thereof, in an amount sufficient to generate hair follicles or stimulate hair growth on the skin, wherein the EGFR inhibitor is a non-naturally occurring nitrogen-including heterocycle of less than about 2,000 daltons or a metabolite thereof and with the proviso that the skin is not an eyelid.

The invention also features a method for generating a hair follicle or stimulating a hair growth on the skin of a subject by (i) inducing reepithelialization of the skin of the subject; and (ii) contacting the cells of the skin with an EGFR antibody in an amount sufficient to generate hair follicles or stimulate hair growth on the skin.

The invention features a method for generating a hair follicle or stimulating a hair growth on the skin of a subject by (i) inducing reepithelialization of the skin of the subject; and (ii) administering to the subject an EGFR inhibitor selected from a small molecule EGFR inhibitor, or a metabolite thereof, and an EGFR antibody, wherein the EGFR inhibitor is formulated for sustained release and administered in an amount sufficient to generate hair follicles or stimulate hair growth on the skin. In one embodiment, steps (i) and (ii) are performed concurrently.

The invention further features a method for producing pigmented hair on a subject by (i) generating a hair follicle on the subject according to the method of the invention; and (ii)

suppressing an expression of a Wnt protein in the hair follicle. In certain embodiments the step of suppressing an expression of a Wnt protein includes inducing an expression of a Dkk1 protein.

Any of the above methods optionally include the step of contacting the skin of the subject with a composition of the invention.

In one particular embodiment, the methods of the invention include performing the contacting step during the day or performing the contacting step during the night.

In any of the forgoing methods the EGFR inhibitor can be administered systemically or topically.

In any of the forgoing methods the reepithelialized skin lacks a stratum corneum, includes newly formed keratinocytes, or includes embryonic hair follicles exhibiting one or more characteristic markers selected from BerEP4, cytokeratin 15, cytokeratin 17, β-catenin, sonic hedgehog, and alkaline phosphatase.

In an embodiment of the above methods, the method includes generating a hair follicle or stimulating a hair growth on the head, scalp, cheek, chin, or eyebrow of a subject.

For any of the above methods, the subjects can from balding of the scalp, face, or eyebrow. The subject may suffer from a disease associated with balding, such as androgenetic alopecia, discoid lupus erythematosis, congenital hypotrichosis, lichen planopilaris, or scarring alopecia. The methods of the invention can also produce faster hair growth and thicker hair (in comparison to a subject not undergoing treatment). In another aspect, the composition of any of the forgoing methods of the invention can be administered to the subject once or twice daily (e.g., for at least 2, 3, 4, 5, 6, 7, 8, 9, 10, 11, 12, or more consecutive days).

In a particular embodiment of the methods, kits, and compositions of the invention, the small molecule EGFR inhibitor formulated for topical administration includes 0.000001% to 10%, 0.00001% to 10%, 0.00001% to 1%, 0.0001% to 1%, 0.0001% to 0.5%, 0.001% to 0.5%, 0.01% to 0.5%, 0.1% to 0.5%, or even 0.001% to 0.1% (w/v) of a small molecule EGFR inhibitor.

In another particular embodiment of the methods, kits, and compositions of the invention, the topical-formulations include a pharmaceutically acceptable excipient selected from an antioxidant (e.g., thiols, sulphoximines, metal chelators, fatty acids, vitamins (including vitamin E), phenols, stilbenes, uric acid, mannose, selenium, and propyl gallate), an emulsifying excipient (e.g., polyethoxylated fatty acids, PEG-fatty acid diesters, PEG-fatty acid mono-ester and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, ionic surfactants, tocopherol esters, and sterol esters), a gelling agent, a hydrocolloid, a cross-linking agent, and a plasticizer. In one embodiment, the topical formulation can include from 0.5 to 50%, 0.5 to 25%, 0.5 to 15%, 0.5 to 10%, 0.5 to 5%, or 0.5 to 3% (w/w) one or more emulsifying excipients, from 0.5 to 50%, 0.5 to 25%, 0.5 to 15%, 0.5 to 10%, 0.5 to 5%, or 0.5 to 3% (w/w) one or more gelling agents, from 0.001% to 3%, 0.01% to 1%, 0.05% to 0.5% (w/w) one or more antioxidants, from 0.001% to 3%, 0.01% to 1%, 0.05% to 0.5% (w/w) one or more cross-linking agents, from 0.001% to 3%, 0.01% to 1%, 0.05% to 0.5% (w/w) one or more plasticizers, and from 0.5 to 50%, 0.5 to 25%, 0.5 to 15%, 0.5 to 10%, 0.5 to 5%, or 0.5 to 3% (w/w) one or more hydrocolloids.

In yet another particular embodiment of the methods, kits, and compositions of the invention, the EGFR inhibitor (e.g., a small molecule EGFR inhibitor or EGFR antibody) is combined (e.g., administered, formulated, or contained in a kit) with an additional biologically active agent selected from an antihistamine (e.g., mepyramine, diphenhydramine, and antazoline), an anti-inflammatory (e.g., corticosteroids, NTHEs, and COX-2 inhibitors), a retinoid (e.g., 13-cis-retinoic acid, adapalene, all-trans-retinoic acid, and etretinate), an anti-androgen (e.g., finasteride, flutamide, diazoxide, 11alpha-hydroxyprogesterone, ketoconazole, RU58841, dutasteride, fluridil, and QLT-7704), an immunosuppressant (e.g., cyclosporine, tacrolimus, rapamycin, everolimus, and pimecrolimus), a channel opener (e.g., minoxidil, diazoxide, and phenyloin), an antibiotic, and an antimicrobial (e.g., benzyl benzoate, benzalkonium chloride, benzoic acid, benzyl alcohol, butylparaben, ethylparaben, methylparaben, propylparaben, camphorated metacresol, camphorated phenol, hexylresorcinol, methylbenzethonium chloride, cetrimide, chlorhexidine, chlorobutanol, chlorocresol, cresol, glycerin, imidurea, phenol, phenoxyethanol, phenylethylalcohol, phenylmercuric acetate, phenylmercuric borate, phenylmercuric nitrate, potassium sorbate, sodium benzoate, sodium proprionate, sorbic acid, and thiomersal).

In a particular embodiment of the methods, kits, and compositions of the invention, the EGFR inhibitor is administered, formulated, or is part of a kit with an anti-androgen (e.g., finasteride) and a channel opener (e.g., minoxidil).

In still another embodiment of the methods, kits, and compositions of the invention, the topical formulation is a cream, lotion, stick, ointment, gel, spray, foam, patch, aerosol, wound dressing, or drop.

In an embodiment of any of the forgoing methods, kits, and compositions, the small molecule EGFR inhibitor is selected from leflunomide, the leflunomide metabolite A771726, gefitinib, erlotinib, lapatinib, canertinib, vandetanib, CL-387785, PKI166, pelitinib, HKI-272, and HKI-357.

In another embodiment of any of the forgoing methods, kits, and compositions, the EGFR antibody is selected from zalutumumab, cetuximab, IMC 11F8, matuzumab, SC 100, ALT 110, PX 1032, BMS599626, MDX 214, and PX 1041.

The terms "administration" and "administering" refer to a method of giving a dosage of a pharmaceutical composition to a patient, where the method is, e.g., topical, oral, intravenous, transdermal, subcutaneous, intraperitoneal, or intramuscular. The preferred method of administration can vary depending on various factors, e.g., the components of the pharmaceutical composition, site at which hair growth and hair follicle generation is desired. In the methods, kits, and compositions of the invention, the administration is, desirably, topical.

By "an amount sufficient" is meant the amount of an EGFR inhibitor (e.g., a small molecule EGFR inhibitor or an EGFR antibody) required to increase the rate of new hair follicle generation and/or new hair growth on the scalp or eyebrow of a subject in comparison to the rate of new hair follicle generation or hair growth observed in the absence of treatment. The effective amount of EGFR inhibitor used to practice the present invention varies depending upon the inhibitor being used, the manner of administration, the age, body weight, and general health of the subject. Ultimately, the attending physician, will decide the appropriate amount and dosage regimen. Such amount is referred to as "an amount sufficient."

As used herein, "reepithelization" refers to the process that occurs during formation of a new epidermis. Tissue undergoing this process can be characterized by the lack of hair follicle morphogenesis, cells in an embryonic-like state, or by lack of a stratum corneum.

By "disruption" is meant a sufficient amount of disturbance to existing hair follicles and the surrounding epidermis and/or dermis to induce an "embryonic-like" state. This embryonic-like state includes the activation, migration, and differentiation of epithelial stem cells from the bulge region of the hair follicle or the interfollicular epidermis. The depth of skin disruption can include in increasing amounts: partial removal of the stratum corneum, complete removal of the stratum corneum, partial removal of the epidermis, complete removal of the epidermis, partial disruption of the dermis and complete removal of the dermis. Skin disruption can also include disruption of the mid to lower epidermis and/or dermis without any disturbance to the stratum-corneum and/or outer epidermis. Different levels of skin disruption can be accomplished by chemical, energetic, mechanical, sound, ultrasound, and/or electromagnetic based methods.

By "controlled release" is meant the regulated spatial and temporal release of a therapeutic compound from a formulation. The term "controlled release" is meant to include delayed release, sustained release, and release from the formulation in pulses or sinusoidal patterns. In controlled release formulations the $t_{max}$ may or may not change. The controlled release of the compound may be activated by an exogenous or endogenous stimulus.

By "delayed release" is meant that the therapeutically active component is not immediately released from the formulation (e.g., a carrier particle).

By "sustained release" is meant a form of controlled release whereby the therapeutically active compound is released over an extended period of time.

As used herein, "formulated for topical administration" refers to a composition of the invention containing a therapeutic compound and formulated with a pharmaceutically acceptable excipient to form a dispersible composition. Compositions formulated for topical administration (e.g., as a cream, gel, lotion, ointment, microdermabrasion particle, and any other topical formulation described herein) are those manufactured or sold in accordance with governmental regulations regarding a therapeutic regimen that includes instructions for the topical administration of the composition.

By "small molecule EGFR inhibitor" is meant a molecule that inhibits the function of one or more EGFR family tyrosine kinases. Tyrosine kinases of the EGFR family include EGFR, HER-2, and HER-4 (see Raymond et al., *Drugs* 60(Suppl. 1):15 (2000); and Harari et al., *Oncogene* 19:6102 (2000)). Small molecule EGFR inhibitors include, for example, gefitinib (Baselga et al., *Drugs* 60(Suppl. 1):33 (2000)), erlotinib (Pollack et al., *J. Pharm. Exp. Ther.* 291:739 (1999)), lapatinib (Lackey et al., 92nd AACR Meeting, New Orleans, abstract 4582 (2001)), canertinib (Bridges et al., *Curr. Med. Chem.* 6:825 (1999)), vandetanib (Wedge et al., *Cancer Res.* 62:4645 (2002)), CL-387785 (Discafani et al., *Biochem. Pharmacol.* 57:917 (1999)), PKI166 (Takada et al., *Drug Metab. Dispos.* 32:1272 (2004)), pelitinib (Torrance et al., *Nature Medicine* 6:1024 (2000)), HKI-272, HKI-357 (for HKI-272 and HKI-357 see, for example, Greenberger et al., 11th NCI-EORTC-AACR Symposium on New Drugs in Cancer Therapy, Amsterdam, abstract 388 (2000); Rabindran et al., *Cancer Res.* 64:3958 (2004); Holbro et al., *Ann. Rev. Pharm. Tox.* 44:195 (2004); Tsou et al., *J. Med. Chem.* 48:1107 (2005); and Tejpar et al., *J. Clin. Oncol.* ASCO Annual Meeting Proc. 22:3579 (2004)), and leflunomide (Kochhar et al., *FEBS Lett.* 334:161 (1993)). The structures for each of these compounds is provided below in Table 1.

TABLE 1

| EGFR Inhibitors | |
| --- | --- |
| Drug | Structure |
| leflunomide | 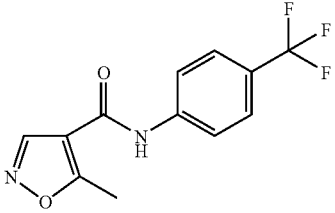 |
| gefitinib | 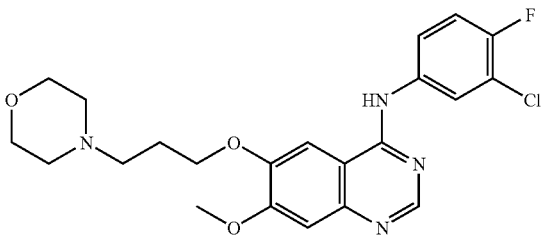 |

TABLE 1-continued
EGFR Inhibitors
| Drug | Structure |
|---|---|
| erlotinib | 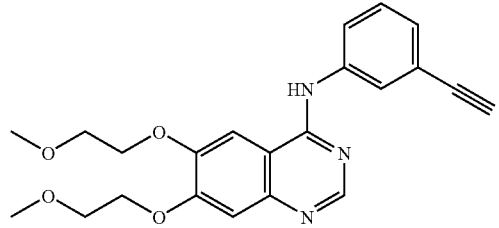 |
| lapatinib | 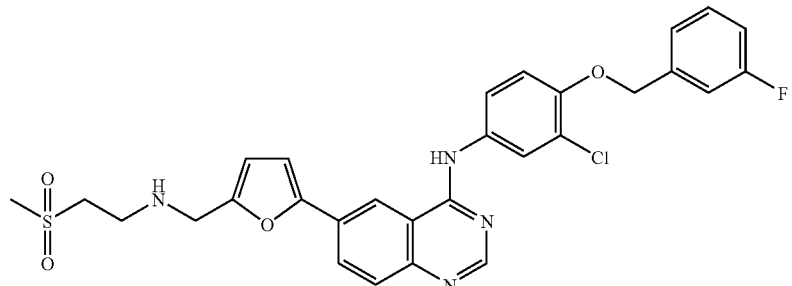 |
| canertinib | 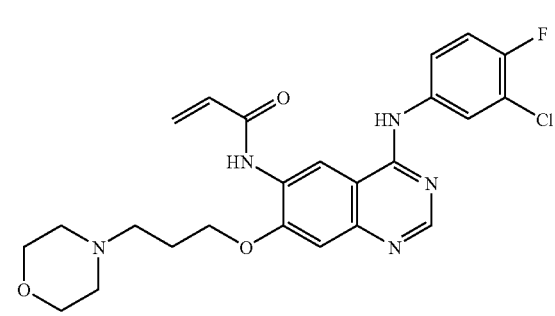 |
| vandetanib | 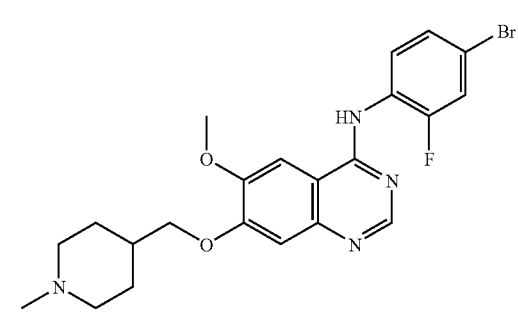 |
| CL-387785 | 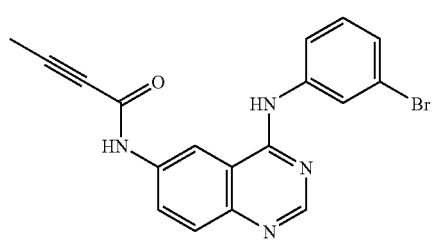 |

TABLE 1-continued

EGFR Inhibitors

| Drug | Structure |
| --- | --- |
| PKI166 | *(structure)* |
| pelitinib | *(structure)* |
| HKI-272 | *(structure)* |
| HKI-357 | *(structure)* |

Small molecule EGFR inhibitors which can be used in the methods and compositions of the invention include anilinoquinazolines, such as gefitinib, erlotinib, lapatinib, canertinib, vandetanib, and CL-387785 and the other anilinoquinazolines disclosed in PCT Publication No. WO/2005/018677 and U.S. Pat. Nos. 5,747,498 and 5,457,105; quinoline-3-carbonitriles, such as pelitinib, HKI-272, and HKI-357, and the quinoline-3-carbonitriles disclosed in U.S. Pat. Nos. 6,288,082 and 6,002,008; pyrrolopyrimidines, such as PKI166, and the pyrrolopyrimidines disclosed in U.S. Pat. No. 6,713,474 and U.S. Patent Publication Nos. 20060211678, 20060035912, 20050239806, 20050187389, 20050165029, 20050153989, 20050037999, 20030187001, and 20010027197; pyridopyrimidines, such as those disclosed in U.S. Pat. Nos. 5,654,307 and 6,713,484; pyrazolopyrimidines, such as those disclosed in U.S. Pat. Nos. 6,921,763 and 6,660,744 and U.S. Patent Publication Nos. 20060167020, 20060094706, 20050267133, 20050119282, 20040006083, and 20020156081; isoxazoles, such as leflunomide; imidazoloquinazolines, pyrroloquinazolines, and pyrazoloquinazolines. Preferably, the small molecule EGFR inhibitor contains a heterobicyclic or heterotricyclic ring system. Each of the patent publications listed above is incorporated herein by reference.

By "A77 7628" is meant the active metabolite of leflunomide having the structure below.

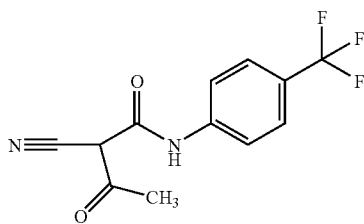

As used herein, to "promote differentiation" refers to the act of increasing the percentage of cells that will differentiate as indicated or to increase the number of cells per unit area of skin that will differentiate.

By "uncommitted epidermal cell" is meant an epidermal stem cell, a bulge cell, a bulge-derived cell, or any other type of cell known in the art that can be induced to differentiate into an HF cell.

By "HF cell" is meant an HF stem cell, a dermal papilla cell, a bulb cell, a matrix cell, a hair shaft cell, an inner root sheath cell, an outer root sheath cell, a melanocyte stem cell, or a melanocyte.

By "EDIHN" is meant HF neogenesis induced by disruption of the epithelial layer, such as by abrasion or wounding, among others. Using the methods of the invention, during the reepithelialization which follows the disruption of the epithelial layer, the skin is contact with a small molecule EGFR inhibitor to promote a differentiation of an uncommitted epidermal cell into a HF cell.

By "corticosteroid" is meant any naturally occurring or synthetic compound characterized by a hydrogenated cyclopentanoperhydrophenanthrene ring system and having immunosuppressive and/or antiinflammatory activity. Naturally occurring corticosteroids are generally produced by the adrenal cortex. Synthetic corticosteriods may be halogenated. Examples corticosteroids are provided herein.

Other features and advantages of the invention will be apparent from the following Detailed Description, the drawings, and the claims.

BRIEF DESCRIPTION OF THE DRAWINGS

FIG. 20A. Top panel: lower left panel AP staining of the dermis; lower right panel: K17 staining of the epidermis. FIG. 20B. Graphical representation of enhancement of EDIHN by depilation.

FIG. 22. Transcripts up-regulated at least 2-fold in activated HF cells, as assessed by dChip analysis. FIGS. 22A-22H. Mean values and standard errors of the up-regulated transcripts in non-activated ("bs-line") and activated ("expt") samples and fold-changes and differences between non-activated and activated values are depicted. FIG. 22I-22M. Raw data for up-regulated transcripts in non-activated and activated cells. "Ctrl" denotes non-activated and "High-dep" denotes activated cells. FIG. 22N-22S. Additional information about up-regulated transcripts.

FIG. 23. Pigmented hair follicle neogenesis observed in the skin of Dkk1-expressing mice following EDIHN.

FIG. 25. EGF inhibits HF formation by EDIHN.

FIG. 26. Administration of an EGF receptor inhibitor (AG1478) leads to generation of more and larger HF compared with controls.

DETAILED DESCRIPTION

Figure 1:
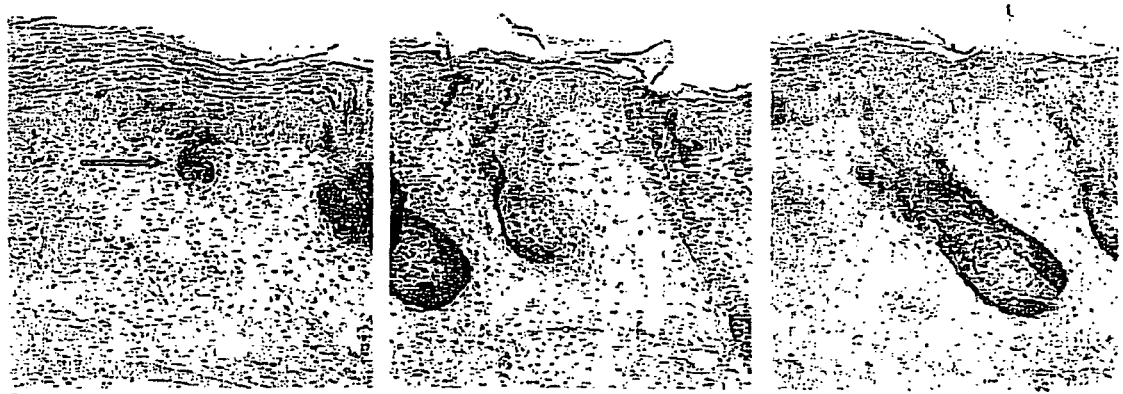
FIG. 1. Epidermal abrasion results in de novo hair follicle (HF) formation. HF at progressive stages of development are depicted in the left, center, and right panels. The arrow in the left panel indicates a hair germ. The dark stained cells are progeny of HF stem cells in the bulge.

The invention features methods, kits, and compositions for generating new hair follicles and growing hair on a subject. The methods of the invention can include reepithelialization of the skin tissue prior to administration of a small molecule EGFR inhibitor. Further details of the methods, kits, and compositions of the invention are provided below.

Topical Formulations

In the methods of the invention, the small molecule EGFR inhibitor can be delivered to the skin in a topical formulation. Topical formulations include, without limitation, creams, lotions, gels, sticks, ointments, sprays, foams, patches, aerosols, wound dressings, and drops. The formulations can be administered, for example, using a metered dose spray applicator, a micro-needle, iontophoresis, ultrasound penetration enhancement, electroporation, nano/micro-injection, sponge, or by applying and spreading the formulation by hand.

Any conventional pharmacologically and cosmetically acceptable vehicles may be used. For example, the small molecule EGFR inhibitors may be administered in liposomal formulations that allow the biologically active compounds to enter the skin. Such liposomal formulations are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; and PCT Publication No. WO 96/40061. Examples of other appropriate vehicles are described in U.S. Pat. No. 4,877,805 and EP Publication No. 0586106A1. Suitable vehicles of the invention may also include mineral oil, petrolatum, polydecene, stearic acid, isopropyl myristate, polyoxyl 40 stearate, stearyl alcohol, or vegetable oil.

The formulations can include various conventional colorants, fragrances, thickeners (e.g., xanthan gum), preservatives, humectants, emollients (e.g., hydrocarbon oils, waxes, or silicones), demulcents, emulsifying excipients, dispersants, penetration enhancers, plasticizing agents, preservatives, stabilizers, demulsifiers, wetting agents, emulsifiers, moisturizers, astringents, deodorants, and the like can be added to provide additional benefits and improve the feel and/or appearance of the topical preparation.

The topical formulations of the invention will typically have a pH of between 5.5 and 8.5 and include from about 0.000001% to 10% (w/v), desirably 0.001% to 0.1% (w/v), small molecule EGFR inhibitor.

Antioxidants

The small molecule EGFR inhibitor formulations of the invention can contain one or more antioxidants. Useful antioxidants include, without limitation, thiols (e.g., aurothioglucose, dihydrolipoic acid, propylthiouracil, thioredoxin, glutathione, cysteine, cystine, cystamine, thiodipropionic acid), sulphoximines (e.g., buthionine-sulphoximines, homo-cysteine-sulphoximine, buthionine-sulphones, and penta-, hexa- and heptathionine-sulphoximine), metal chelators (e.g., α-hydroxy-fatty acids, palmitic acid, phytic acid, lactoferrin, citric acid, lactic acid, and malic acid, humic acid, bile acid, bile extracts, bilirubin, biliverdin, EDTA, EGTA, and DTPA), vitamins (e.g., vitamin E, vitamin C, ascorbyl palmitate, Mg ascorbyl phosphate, and ascorbyl acetate), phenols (e.g., butylhydroxytoluene, butylhydroxyanisole, ubiquinol, nordihydroguaiaretic acid, trihydroxybutyrophenone), benzoates (e.g., coniferyl benzoate), uric acid, mannose, propyl gallate, selenium (e.g., selenium-methionine), stilbenes (e.g., stilbene oxide and trans-stilbene oxide), and combinations thereof.

Antioxidants that may be incorporated into the formulations of the invention include natural antioxidants prepared from plant extracts, such as extracts from aloe vera; avocado; chamomile; echinacea; ginko biloba; ginseng; green tea; heather; jojoba; lavender; lemon grass; licorice; mallow; oats; peppermint; St. John's wort; willow; wintergreen; wheat wild yam extract; marine extracts; and mixtures thereof.

The total amount of antioxidant included in the formulations can be from 0.001% to 3% by weight, preferably 0.01% to 1% by weight, in particular 0.05% to 0.5% by weight, based on the total weight of the formulation.

Emulsifying Excipients

Small molecule EGFR inhibitor formulations of the invention can include one or more emulsifying excipients. Emulsifying excipients that may be used in the formulations of the invention include, without limitation, compounds belonging to the following classes: polyethoxylated fatty acids, PEG-fatty acid diesters, PEG-fatty acid mono-ester and di-ester mixtures, polyethylene glycol glycerol fatty acid esters, alcohol-oil transesterification products, polyglycerized fatty acids, propylene glycol fatty acid esters, mixtures of propylene glycol esters and glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, ionic surfactants, tocopherol esters, and sterol esters. Commercially available examples for each class of excipient are provided below.

Polyethoxylated fatty acids may be used as excipients for the formulation of small molecule EGFR inhibitors. Examples of commercially available polyethoxylated fatty acid monoester surfactants include: PEG 4-100 monolaurate (Crodet L series, Croda), PEG 4-100 monooleate (Crodet O series, Croda), PEG 4-100 monostearate (Crodet S series, Croda, and Myrj Series, Atlas/ICI), PEG 400 distearate (Cithrol 4DS series, Croda), PEG 100, 200, or 300 monolaurate (Cithrol ML series, Croda), PEG 100, 200, or 300 monooleate (Cithrol MO series, Croda), PEG 400 dioleate (Cithrol 4DO series, Croda), PEG 400-1000 monostearate (Cithrol MS series, Croda), PEG-1 stearate (Nikkol MYS-1EX, Nikko, and Coster K1, Condea), PEG-2 stearate (Nikkol MYS-2, Nikko), PEG-2 oleate (Nikkol MYO-2, Nikko), PEG-4 laurate (Mapeg® 200 mL, PPG), PEG-4 oleate (Mapeg® 200 MO, PPG), PEG-4 stearate (Kessco® PEG 200 MS, Stepan), PEG-5 stearate (Nikkol TMGS-5, Nikko), PEG-5 oleate (Nikkol TMGO-5, Nikko), PEG-6 oleate (Algon OL 60, Auschem SpA), PEG-7 oleate (Algon OL 70, Auschem SpA), PEG-6 laurate (Kessco® PEG300 ML, Stepan), PEG-7 laurate (Lauridac 7, Condea), PEG-6 stearate (Kessco® PEG300 MS, Stepan), PEG-8 laurate (Mapeg® 400 ML, PPG), PEG-8 oleate (Mapeg® 400 MO, PPG), PEG-8 stearate (Mapeg® 400 MS, PPG), PEG-9 oleate (Emulgante A9, Condea), PEG-9 stearate (Cremophor S9, BASF), PEG-10 laurate (Nikkol MYL-10, Nikko), PEG-10 oleate (Nikkol MYO-10, Nikko), PEG-12 stearate (Nikkol MYS-10, Nikko), PEG-12 laurate (Kessco® PEG 600 ML, Stepan), PEG-12 oleate (Kessco® PEG 600 MO, Stepan), PEG-12 ricinoleate (CAS #9004-97-1), PEG-12 stearate (Mapeg® 600 MS, PPG), PEG-15 stearate (Nikkol TMGS-15, Nikko), PEG-15 oleate (Nikkol TMGO-15, Nikko), PEG-20 laurate (Kessco® PEG 1000 ML, Stepan), PEG-20 oleate (Kessco® PEG 1000 MO, Stepan), PEG-20 stearate (Mapeg® 1000 MS, PPG), PEG-25 stearate (Nikkol MYS-25, Nikko), PEG-32 laurate (Kessco® PEG 1540 ML, Stepan), PEG-32 oleate (Kessco® PEG 1540 MO, Stepan), PEG-32 stearate (Kessco® PEG 1540 MS, Stepan), PEG-30 stearate (Myrj 51), PEG-40 laurate (Crodet L40, Croda), PEG-40 oleate (Crodet O40, Croda), PEG-40 stearate (Emerest® 2715, Henkel), PEG-45 stearate (Nikkol MYS-45, Nikko), PEG-50 stearate (Myrj 53), PEG-55 stearate (Nikkol MYS-55, Nikko), PEG-100 oleate (Crodet O-100, Croda), PEG-100 stearate (Ariacel 165, ICI), PEG-200 oleate (Albunol 200 MO, Taiwan Surf.), PEG-400 oleate (LACTOMUL, Henkel), and PEG-600 oleate (Albunol 600 MO, Taiwan Surf.). Formulations of the invention may include one or more of the polyethoxylated fatty acids above.

Polyethylene glycol fatty acid diesters may be used as excipients for the formulation of small molecule EGFR inhibitors. Examples of commercially available polyethylene glycol fatty acid diesters include: PEG-4 dilaurate (Mapeg® 200 DL, PPG), PEG-4 dioleate (Mapeg® 200 DO, PPG), PEG-4 distearate (Kessco® 200 DS, Stepan), PEG-6 dilaurate (Kessco® PEG 300 DL, Stepan), PEG-6 dioleate (Kessco® PEG 300 DO, Stepan), PEG-6 distearate (Kessco® PEG 300 DS, Stepan), PEG-8 dilaurate (Mapeg® 400 DL, PPG), PEG-8 dioleate (Mapeg® 400 DO, PPG), PEG-8 distearate (Mapeg® 400 DS, PPG), PEG-10 dipalmitate (Polyaldo 2PKFG), PEG-12 dilaurate (Kessco® PEG 600 DL, Stepan), PEG-12 distearate (Kessco® PEG 600 DS, Stepan), PEG-12 dioleate (Mapeg® 600 DO, PPG), PEG-20 dilaurate (Kessco® PEG 1000 DL, Stepan), PEG-20 dioleate (Kessco® PEG 1000 DO, Stepan), PEG-20 distearate (Kessco® PEG 1000 DS, Stepan), PEG-32 dilaurate (Kessco® PEG 1540 DL, Stepan), PEG-32 dioleate (Kessco® PEG 1540 DO, Stepan), PEG-32 distearate (Kessco® PEG 1540 DS, Stepan), PEG-400 dioleate (Cithrol 4DO series, Croda), and PEG-400 distearate Cithrol 4DS series, Croda). Formulations of the invention may include one or more of the polyethylene glycol fatty acid diesters above.

PEG-fatty acid mono- and di-ester mixtures may be used as excipients for the formulation of small molecule EGFR inhibitors. Examples of commercially available PEG-fatty acid mono- and di-ester mixtures include: PEG 4-150 mono, dilaurate (Kessco® PEG 200-6000 mono, Dilaurate, Stepan), PEG 4-150 mono, dioleate (Kessco® PEG 200-6000 mono, Dioleate, Stepan), and PEG 4-150 mono, distearate (Kessco® 200-6000 mono, Distearate, Stepan). Formulations of the invention may include one or more of the PEG-fatty acid mono- and di-ester mixtures above.

Polyethylene glycol glycerol fatty acid esters may be used as excipients for the formulation of small molecule EGFR inhibitors. Examples of commercially available polyethylene glycol glycerol fatty acid esters include: PEG-20 glyceryl laurate (Tagat® L, Goldschmidt), PEG-30 glyceryl laurate (Tagat® L2, Goldschmidt), PEG-15 glyceryl laurate (Glycerox L series, Croda), PEG-40 glyceryl laurate (Glycerox L series, Croda), PEG-20 glyceryl stearate (Capmul® EMG, ABITEC), and Aldo® MS-20 KFG, Lonza), PEG-20 glyceryl oleate (Tagat® 0, Goldschmidt), and PEG-30 glyceryl oleate (Tagat® O2, Goldschmidt). Formulations of the invention may include one or more of the polyethylene glycol glycerol-fatty acid esters above.

Alcohol-oil transesterification products may be used as excipients for the formulation of small molecule EGFR inhibitors. Examples of commercially available alcohol-oil transesterification products include: PEG-3 castor oil (Nikkol CO-3, Nikko), PEG-5, 9, and 16 castor oil (ACCONON CA series, ABITEC), PEG-20 castor oil, (Emalex C-20, Nihon Emulsion), PEG-23 castor oil (Emulgante EL23), PEG-30 castor oil (Incrocas 30, Croda), PEG-35 castor oil (Incrocas-35, Croda), PEG-38 castor oil (Emulgante EL 65, Condea), PEG-40 castor oil (Emalex C-40, Nihon Emulsion), PEG-50 castor oil (Emalex C-50, Nihon Emulsion), PEG-56 castor oil (Eumulgin® PRT 56, Pulcra SA), PEG-60 castor oil (Nikkol CO-60TX, Nikko), PEG-100 castor oil, PEG-200 castor oil (Eumulgin® PRT 200, Pulcra SA), PEG-5 hydrogenated castor oil (Nikkol HCO-5, Nikko), PEG-7 hydrogenated castor oil (Cremophor WO7, BASF), PEG-10 hydrogenated castor oil (Nikkol HCO-10, Nikko), PEG-20 hydrogenated castor oil (Nikkol HCO-20, Nikko), PEG-25 hydrogenated castor oil (Simulsol® 1292, Seppic), PEG-30 hydrogenated castor oil (Nikkol HCO-30, Nikko), PEG-40 hydrogenated castor oil (Cremophor RH 40, BASF), PEG-45 hydrogenated castor oil (Cerex ELS 450, Auschem Spa), PEG-50 hydrogenated castor oil (Emalex HC-50, Nihon Emulsion), PEG-60 hydrogenated castor oil (Nikkol HCO-60, Nikko), PEG-80 hydrogenated castor oil (Nikkol HCO-80, Nikko), PEG-100 hydrogenated castor oil (Nikkol HCO-100, Nikko), PEG-6 corn oil (Labrafil® M 2125 CS, Gattefosse), PEG-6 almond oil (Labrafil® M 1966 CS, Gattefosse), PEG-6 apricot kernel oil (Labrafil® M 1944 CS, Gattefosse), PEG-6 olive oil (Labrafil® M 1980 CS, Gattefosse), PEG-6 peanut oil (Labrafil® M 1969 CS, Gattefosse), PEG-6 hydrogenated palm kernel oil (Labrafil® M 2130 BS, Gattefosse), PEG-6 palm kernel oil (Labrafil® M 2130 CS, Gattefosse), PEG-6 triolein (Labrafil® M 2735 CS, Gattefosse), PEG-8 corn oil (Labrafil® WL 2609 BS, Gattefosse), PEG-20 corn glycerides (Crovol M40, Croda), PEG-20 almond glycerides (Crovol A40, Croda), PEG-25 trioleate (TAGAT® TO, Goldschmidt), PEG-40 palm kernel oil (Crovol PK-70), PEG-60 corn glycerides (Crovol M70, Croda), PEG-60 almond glycerides (Crovol A70, Croda), PEG-4 caprylic/capric triglyceride (Labrafac® Hydro, Gattefosse), PEG-8 caprylic/capric glycerides (Labrasol, Gattefosse), PEG-6 caprylic/capric glycerides (SOFTIGEN®767, Huls), lauroyl macrogol-32 glyceride (GELUCIRE 44/14, Gattefosse), stearoyl macrogol glyceride (GELUCIRE 50/13, Gattefosse), mono, di, tri, tetra esters of vegetable oils and sorbitol (SorbitoGlyceride, Gattefosse), pentaerythrityl tetraisostearate (Crodamol PTIS, Croda), pentaerythrityl distearate (Albunol DS, Taiwan Surf.), pentaerythrityl tetraoleate (Liponate PO-4, Lipo Chem.), pentaerythrityl tetrastearate (Liponate PS-4, Lipo Chem.), pentaerythrityl tetracaprylate tetracaprate (Liponate PE-810, Lipo Chem.), and pentaerythrityl tetraoctanoate (Nikkol Pentarate 408, Nikko). Also included as oils in this category of surfactants are oil-soluble vitamins, such as vitamins A, D, E, K, etc. Thus, derivatives of these vitamins, such as tocopheryl PEG-1000 succinate (TPGS, available from Eastman), are also suitable surfactants. Formulations of the invention may include one or more of the alcohol-oil transesterification products above.

Polyglycerized fatty acids may be used as excipients for the formulation of small molecule EGFR inhibitors. Examples of commercially available polyglycerized fatty acids include: polyglyceryl-2 stearate (Nikkol DGMS, Nikko), polyglyceryl-2 oleate (Nikkol DGMO, Nikko), polyglyceryl-2 isostearate (Nikkol DGMIS, Nikko), polyglyceryl-3 oleate (Capron® 3GO, ABITEC), polyglyceryl-4 oleate (Nikkol Tetraglyn 1-O, Nikko), polyglyceryl-4 stearate (Nikkol Tetraglyn 1-S, Nikko), polyglyceryl-6 oleate (Drewpol 6-1-O, Stepan), polyglyceryl-10 laurate (Nikkol Decaglyn 1-L, Nikko), polyglyceryl-10 oleate (Nikkol Decaglyn 1-O, Nikko), polyglyceryl-10 stearate (Nikkol Decaglyn 1-S, Nikko), polyglyceryl-6 ricinoleate (Nikkol Hexaglyn PR-15, Nikko), polyglyceryl-10 linoleate (Nikkol Decaglyn 1-LN, Nikko), polyglyceryl-6 pentaoleate (Nikkol Hexaglyn 5-O, Nikko), polyglyceryl-3 dioleate (Cremophor GO32, BASF), polyglyceryl-3 distearate (Cremophor GS32, BASF), polyglyceryl-4 pentaoleate (Nikkol Tetraglyn 5-O, Nikko), polyglyceryl-6 dioleate (Caprol® 6G20, ABITEC), polyglyceryl-2 dioleate (Nikko), DGDO, Nikko), polyglyceryl-10 trioleate (Nikkol Decaglyn 3-O, Nikko), polyglyceryl-10 pentaoleate (Nikkol Decaglyn 5-O, Nikko), polyglyceryl-10 septaoleate (Nikkol Decaglyn 7-O, Nikko), polyglyceryl-10 tetraoleate (Caprol® 10G4O, ABITEC), polyglyceryl-10 decaisostearate (Nikkol Decaglyn 10-IS, Nikko), polyglyceryl-101 decaoleate (Drewpol 10-10-O, Stepan), polyglyceryl-10 mono, dioleate (Capronl® PGE 860, ABITEC), and polyglyceryl polyricinoleate (Polymuls, Henkel). Formulations of the invention may include one or more of the polyglycerized fatty acids above.

Propylene glycol fatty acid esters may be used as excipients for the formulation of small molecule EGFR inhibitors. Examples of commercially available propylene glycol fatty acid esters include: propylene glycol monocaprylate (Capryol 90, Gattefosse), propylene glycol monolaurate (Lauroglycol 90, Gattefosse), propylene glycol oleate (Lutrol OP2000, BASF), propylene glycol myristate (Mirpyl), propylene glycol monostearate (LIPO PGMS, Lipo Chem.), propylene glycol hydroxystearate, propylene glycol ricinoleate (PROPYMULS, Henkel), propylene glycol isostearate, propylene glycol monooleate (Myverol P-O6, Eastman), propylene glycol dicaprylate dicaprate (Captex® 200, ABITEC), propylene glycol dioctanoate (Captex® 800, ABITEC), propylene glycol caprylate caprate (LABRAFAC PG, Gattefosse), propylene glycol dilaurate, propylene glycol distearate (Kessco® PGDS, Stepan), propylene glycol dicaprylate (Nikkol Sefsol 228, Nikko), and propylene glycol dicaprate (Nikkol PDD, Nikko). Formulations the invention may include one or more of the propylene glycol fatty acid esters above.

Mixtures of propylene glycol esters and glycerol esters may be used as excipients for the formulation of small molecule EGFR inhibitors. One preferred mixture is composed of the oleic acid esters of propylene glycol and glycerol (Arlacel 186). Examples of these surfactants include: oleic (ATMOS 300, ARLACEL 186, ICI), stearic (ATMOS 150). Formulations of the invention may include one or more of the mixtures of propylene glycol esters and glycerol esters above.

Mono- and diglycerides may be used as excipients for the formulation of small molecule EGFR inhibitors. Examples of commercially available mono- and diglycerides include: monopalmitolein (C16:1) (Larodan), monoelaidin (C18:1) (Larodan), monocaproin (C6) (Larodan), monocaprylin (Larodan), monocaprin (Larodan), monolaurin (Larodan), glyceryl monomyristate (C14) (Nikkol MGM, Nikko), glyceryl monooleate (C18:1) (PECEOL, Gattefosse), glyceryl monooleate (Myverol, Eastman), glycerol monooleate/linoleate (OLICINE, Gattefosse), glycerol monolinoleate (Maisine, Gattefosse), glyceryl ricinoleate (Softigen® 701, Huls), glyceryl monolaurate (ALDO® MLD, Lonza), glycerol monopalmitate (Emalex GMS-P, Nihon), glycerol monostearate (Capmul® GMS, ABITEC), glyceryl mono- and dioleate (Capmul® GMO-K, ABITEC), glyceryl palmitic/stearic (CUTINA MD-A, ESTAGEL-G 18), glyceryl acetate (Lamegin® EE, Grunau GmbH), glyceryl laurate (Imwitor® 312, Huls), glyceryl citrate/lactate/oleate/linoleate (Imwitor® 375, Huls), glyceryl caprylate (Imwitor® 308, Huls), glyceryl caprylate/caprate (Capmul® MCM, ABITEC), caprylic acid mono- and diglycerides (Imwitor® 988, Huls), caprylic/capric glycerides (Imwitor® 742, Huls), Mono- and diacetylated monoglycerides (Myvacet® 9-45, Eastman), glyceryl monostearate (Aldo® MS, Arlacel 129, ICI), lactic acid esters of mono and diglycerides (LAMEGIN GLP, Henkel), dicaproin (C6) (Larodan), dicaprin (C10) (Larodan), dioctanoin (C8) (Larodan), dimyristin (C14) (Larodan), dipalmitin (C16) (Larodan), distearin (Larodan), glyceryl dilaurate (C12) (Capmul® GDL, ABITEC), glyceryl dioleate (Capmul® GDO, ABITEC), glycerol esters of fatty acids (GELUCIRE 39/01, Gattefosse), dipalmitolein (C16:1) (Larodan), 1,2 and 1,3-diolein (C18:1) (Larodan), dielaidin (C18:1) (Larodan), and dilinolein (C18:2) (Larodan). Formulations of the invention may include one or more of the mono- and diglycerides above.

Sterol and sterol derivatives may be used as excipients for the formulation of small molecule EGFR inhibitors. Examples of commercially available sterol and sterol derivatives include: cholesterol, sitosterol, lanosterol, PEG-24 cholesterol ether (Solulan C-24, Amerchol), PEG-30 cholestanol (Phytosterol GENEROL series, Henkel), PEG-25 phytosterol (Nikkol BPSH-25, Nikko), PEG-5 soyasterol (Nikkol BPS-5, Nikko), PEG-10 soyasterol (Nikkol BPS-10, Nikko), PEG-20 soyasterol (Nikkol BPS-20, Nikko), and PEG-30 soyasterol (Nikkol BPS-30, Nikko). Formulations of the invention may include one or more of the sterol and sterol derivatives above.

Polyethylene glycol sorbitan fatty acid esters may be used as excipients for the formulation of small molecule EGFR inhibitors. Examples of commercially available polyethylene glycol sorbitan fatty acid esters include: PEG-10 sorbitan laurate (Liposorb L-10, Lipo Chem.), PEG-20 sorbitan monolaurate (Tween® 20, Atlas/ICI), PEG-4 sorbitan monolaurate (Tween® 21, Atlas/ICI), PEG-80 sorbitan monolaurate (Hodag PSML-80, Calgene), PEG-6 sorbitan monolaurate (Nikkol GL-1, Nikko), PEG-20 sorbitan monopalmitate (Tween® 40, Atlas/ICI), PEG-20 sorbitan monostearate (Tween® 60, Atlas/ICI), PEG-4 sorbitan monostearate (Tween® 61, Atlas/ICI), PEG-8 sorbitan monostearate (DACOL MSS, Condea), PEG-6 sorbitan monostearate (Nikkol TS106, Nikko), PEG-20 sorbitan tristearate (Tween® 65, Atlas/ICI), PEG-6 sorbitan tetrastearate (Nikkol GS-6, Nikko), PEG-60 sorbitan tetrastearate (Nikkol GS-460, Nikko), PEG-5 sorbitan monooleate (Tween® 81, Atlas/ICI), PEG-6 sorbitan monooleate (Nikkol TO-106, Nikko), PEG-20 sorbitan monooleate (Tween® 80, Atlas/ICI), PEG-40 sorbitan oleate (Emalex ET 8040, Nihon Emulsion), PEG-20 sorbitan trioleate (Tween® 85, Atlas/ICI), PEG-6 sorbitan tetraoleate (Nikkol GO-4, Nikko), PEG-30 sorbitan tetraoleate (Nikkol GO-430, Nikko), —PEG-40 sorbitan tetraoleate (Nikkol GO-440, Nikko), PEG-20 sorbitan monoisostearate (Tween® 120, Atlas/ICI), PEG sorbitol hexaoleate (Atlas G-1086, ICI), polysorbate 80 (Tween® 80, Pharma), polysorbate 85 (Tween® 85, Pharma), polysorbate 20 (Tween® 20, Pharma), polysorbate 40 (Tween® 40, Pharma), polysorbate 60 (Tween® 60, Pharma), and PEG-6 sorbitol hexastearate (Nikkol GS-6, Nikko). Formulations of the invention may include one or more of the polyethylene glycol sorbitan fatty acid esters above.

Polyethylene glycol alkyl ethers may be used as excipients for the formulation of small molecule EGFR inhibitors. Examples of commercially available polyethylene glycol alkyl ethers include: PEG-2 oleyl ether, oleth-2 (Brij 92/93, Atlas/ICI), PEG-3 oleyl ether, oleth-3 (Volpo 3, Croda), PEG-5 oleyl ether, oleth-5 (Volpo 5, Croda), PEG-10 oleyl ether, oleth-10 (Volpo 10, Croda), PEG-20 oleyl ether, oleth-20 (Volpo 20, Croda), PEG-4 lauryl ether, laureth-4 (Brij 30, Atlas/ICI), PEG-9 lauryl ether, PEG-23 lauryl ether, laureth-23 (Brij 35, Atlas/ICI), PEG-2 cetyl ether (Brij 52, ICI), PEG-10 cetyl ether (Brij 56, ICI), PEG-20 cetyl ether (BriJ 58, ICI), PEG-2 stearyl ether (Brij 72, ICI), PEG-10 stearyl ether (Brij 76, ICI), PEG-20 stearyl ether (Brij 78, ICI), and PEG-100 stearyl ether (Brij 700, ICI). Formulations of the invention may include one or more of the polyethylene glycol alkyl ethers above.

Sugar esters may be used as excipients for the formulation of small molecule EGFR inhibitors. Examples of commercially available sugar esters include: sucrose distearate (SUCRO ESTER 7, Gattefosse), sucrose distearate/monostearate (SUCRO ESTER 11, Gattefosse), sucrose dipalmitate, sucrose monostearate (Crodesta F-160, Croda), sucrose monopalmitate (SUCRO ESTER 15, Gattefosse), and sucrose monolaurate (Saccharose monolaurate 1695, Mitsubisbi-Kasei). Formulations of the invention may include one or more of the sugar esters above.

Polyethylene glycol alkyl phenols may be used as excipients for the formulation of small molecule EGFR inhibitors. Examples of commercially available polyethylene glycol alkyl phenols include: PEG-10-100 nonylphenol series (Triton X series, Rohm & Haas) and PEG-15-100 octylphenol ether series (Triton N-series, Rohm & Haas). Formulations of the invention may include one or more of the polyethylene glycol alkyl phenols above.

Polyoxyethylene-polyoxypropylene block copolymers may be used as excipients for the formulation of small molecule EGFR inhibitors. These surfactants are available under various trade names, including one or more of Synperonic PE series (ICI), Pluronic® series (BASF), Lutrol (BASF), Supronic, Monolan, Pluracare, and Plurodac. The generic term for these polymers is "poloxamer" (CAS 9003-11-6). These polymers have the formula I:

$$HO(C_2H_4O)_a(C_3H_6O)_b(C_2H_4O)_aH \qquad (I)$$

where "a" and "b" denote the number of polyoxyethylene and polyoxypropylene units, respectively. Formulations of the invention may include one or more of the polyoxyethylene-polyoxypropylene block copolymers above.

Polyoxyethylenes, such as PEG 300, PEG 400, and PEG 600, may be used as excipients for the formulation of small molecule EGFR inhibitors.

Sorbitan fatty acid esters may be used as excipients for the formulation of small molecule EGFR inhibitors. Examples of commercially sorbitan fatty acid esters include: sorbitan monolaurate (Span-20, Atlas/ICI), sorbitan monopalmitate (Span-40, Atlas/ICI), sorbitan monooleate (Span-80, Atlas/ICI), sorbitan monostearate (Span-60, Atlas/ICI), sorbitan trioleate (Span-85, Atlas/ICI), sorbitan sesquioleate (Arlacel-C, ICI), sorbitan tristearate (Span-65, Atlas/ICI), sorbitan monoisostearate (Crill 6, Croda), and sorbitan sesquistearate (Nikkol SS-15, Nikko). Formulations of the invention may include one or more of the sorbitan fatty acid esters above.

Esters of lower alcohols (C2 to C4) and fatty acids (C8 to C18) are suitable surfactants for use in the invention. Examples of these surfactants include: ethyl oleate (Crodamol EO, Croda), isopropyl myristate (Crodamol IPM, Croda), isopropyl palmitate (Crodamol IPP, Croda), ethyl linoleate (Nikkol VF-E, Nikko), and isopropyl linoleate (Nikkol VF-IP, Nikko). Formulations of the invention may include one or more of the lower alcohol fatty acid esters above.

Ionic surfactants may be used as excipients for the formulation of small molecule EGFR inhibitors. Examples of useful ionic surfactants include: sodium caproate, sodium caprylate, sodium caprate, sodium laurate, sodium myristate, sodium myristolate, sodium palmitate, sodium palmitoleate, sodium oleate, sodium ricinoleate, sodium linoleate, sodium linolenate, sodium stearate, sodium lauryl sulfate (dodecyl), sodium tetradecyl sulfate, sodium lauryl sarcosinate, sodium dioctyl sulfosuccinate, sodium cholate, sodium taurocholate, sodium glycocholate, sodium deoxycholate, sodium taurodeoxycholate, sodium glycodeoxycholate, sodium ursodeoxycholate, sodium chenodeoxycholate, sodium taurochenodeoxycholate, sodium glyco cheno deoxycholate, sodium cholylsarcosinate, sodium N-methyl taurocholate, egg yolk phosphatides, hydrogenated soy lecithin, dimyristoyl lecithin, lecithin, hydroxylated lecithin, lysophosphatidylcholine, cardiolipin, sphingomyelin, phosphatidylcholine, phosphatidyl ethanolamine, phosphatidic acid, phosphatidyl glycerol, phosphatidyl serine, diethanolamine, phospholipids, polyoxyethylene-10 oleyl ether phosphate, esterification products of fatty alcohols or fatty alcohol ethoxylates, with phosphoric acid or anhydride, ether carboxylates (by oxidation of terminal OH group of, fatty alcohol ethoxylates), succinylated monoglycerides, sodium stearyl fumarate, stearoyl propylene glycol hydrogen succinate, mono/diacetylated tartaric acid esters of mono- and diglycerides, citric acid esters of mono-, diglycerides, glyceryl-lacto esters of fatty acids, acyl lactylates, lactylic esters of fatty acids, sodium stearoyl-2-lactylate, sodium stearoyl lactylate, alginate salts, propylene glycol alginate; ethoxylated alkyl sulfates, alkyl benzene sulfones, α-olefin sulfonates, acyl isethionates, acyl taurates, alkyl glyceryl ether sulfonates, sodium octyl sulfosuccinate, sodium undecylenamideo-MEA-sulfosuccinate, hexadecyl triammonium bromide, decyl trimethyl ammonium bromide, cetyl trimethyl ammonium bromide, dodecyl ammonium chloride, alkyl benzyldimethylammonium salts, diisobutyl phenoxyethoxydimethyl benzylammonium salts, alkylpyridinium salts, betaines (trialkylglycine), lauryl betaine (N-lauryl,N,N-dimethylglycine), and ethoxylated amines (polyoxyethylene-15 coconut amine). For simplicity, typical counterions are provided above. It will be appreciated by one skilled in the art, however, that any bioacceptable counterion may be used. For example, although the fatty acids are shown as sodium salts, other cation counterions can also be used, such as, for example, alkali metal cations or ammonium. Formulations of the invention may include one or more of the ionic surfactants above.

Tocopherol esters and sterol esters, as described in U.S. Pat. Nos. 6,632,443 and 6,191,172, each of which is incorporated herein by reference, may be used as excipients for the formulation of small molecule EGFR inhibitors. These tocopherol and sterol esters are described by formula II:

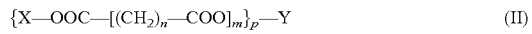
$$\{X-OOC-[(CH_2)_n-COO]_m\}_p-Y \qquad (II)$$

wherein X is selected from α-tocopherol, β-tocopherol, γ-tocopherol, δ-tocopherol, cholesterol, 7-dehydrocholesterol, campesterol, sitosterol, ergosterol, and stigmasterol; p is 1 or 2; m is 0 or 1; n is an integer from 0 to 18; and Y is a hydrophilic moiety selected from polyalcohols, polyethers, and derivatives thereof.

The emulsifying excipients present in the formulations of the invention are present in amounts such that the carrier forms uniform dispersion of small molecule EGFR inhibitor. The relative amounts of surfactants required are readily determined by observing the properties of the resultant small molecule EGFR inhibitor dispersion, as determined using standard techniques for measuring solubilities. The optical clarity of the aqueous dispersion can be measured using standard quantitative techniques for turbidity assessment. For example, a formulation of the invention can include from 0.001% to 10% by weight, preferably 0.01% to 5% by weight, emulsifying excipient.

Gelling Agents

The small molecule EGFR inhibitor formulations of the invention can contain one or more gelling agents. Useful gelling agents include, without limitation, hydroxyethylcellulose (commercially available as NATROSOL® hydroxyethylcellulose produced by Aqualon), hydroxypropylcellulose (commercially available as KLUCEL® hydroxypropylcellulose produced by Aqualon), cross-linked acrylic acid polymers (such as the commercially available product CARBOPOL® cross linked acrylic acid polymer, produced by Goodrich), MVE/MA decadiene crosspolymer (such as the commercially available product STABILEZE® MVE/MA decadiene crosspolymer, produced by ISP), PVM/MA copolymer (such as the commercially available product GANTREZ® PVM/MA copolymer, produced by ISP), ammonium acrylates/acrylonitrogens (commercially available as HYPAN® ammonium acrylates/acrylonitrogens), carboxymethylcellulose, polyvinylpyrrolidone, carbomer (carboxypolymethylene, CAS 541823-57-9; of which different grades with various molecular weights are commercially available), cetostearyl alcohol, colloidal silicon dioxide, gelatin, guar gum, sodium or calcium carboxymethyl cellulose, hydroxyethyl or hydroxypropyl cellulose, hydroxypropylmethylcellulose, methyl or ethyl cellulose, maltodextrin, polyvinyl alcohol, propylene carbonate, povidone, propylene glycol alginate, alginic acid-sodium alginate, sodium starch glycolate, starch, and sucrose. Typically, the gelling agent, when used, is present in an amount between about 0.5% to about 10% by weight of the composition. More particularly, for CARBOPOL® cross linked acrylic acid polymer the preferred compositional weight percent range is between about 2% to about 6%, while for NATROSOL® hydroxyethylcellulose or KLUCEL® hydroxypropylcellulose the preferred range is between about 0.5% to about 4%. Desirably, the compositional weight percent range for STABILEZE® PVM/MA decadiene crosspolymer and HYPAN® ammonium acrylates/acrylonitrogens is between about 1% to about 4%. The preferred compositional weight percent range for polyvinylpyrrolidone is between about 0.5% and about 10%.

Hydrocolloids

The small molecule EGFR inhibitor formulations of the invention can contain one or more hydrocolloids. Useful hydrocolloids include, without limitation, Carbopol, including Carbopol 940, carrageenan, agar, xanthan gum, locust bean gum polyglucomannan, and gelatin.

Cross-Linking Agents

The small molecule EGFR inhibitor formulations of the invention can contain one or more cross-linking agents to form a chemical bond between the molecules of the polymer to gel the dispersion, forming a solid body. Examples of cross-linking agents for locust bean gum, guar or chemically modified guar are galactose, organic titanate or boric acid. When the hydrocolloid is a polyglucomannan (e.g., Konjak®), borax can be used as a cross-linking agent. When xanthan gum is used, a suitable cross-linker for xanthan gum is mannose. If locust bean gum is used as the principle hydrocolloid, lactose or other suitable oligosaccharide can be used.

Plasticizers

The small molecule EGFR inhibitor formulations of the invention can contain one or more plasticizers. Useful plasticizers include, without limitation, alkyl glycols, polyalkylene glycols (e.g., polyethylene glycol and/or polypropylene glycol), benzyl benzoate, chlorobutanol, mineral oil, (CTFA mixture of mineral oils, e.g., Amerchol L-101, Protalan M-16, Protalan M-26), petrolatum (CTFA, mixture of petrolatum, e.g., Amerchol CAB, Forlan 200), lanolin alcohols, sorbitol, triacetin, dibutyl sebacate, diethyl phthalate, glycerine, petrolactam and triethyl citrate.

Other Biologically Active Ingredients

The formulations of the invention can be used in combination with any additional active ingredient described herein. Desirably, the small molecule EGFR inhibitor and the additional active ingredient are formulated together. The amount of an additional active ingredient included will depend on the desired effect and the active ingredient that is selected. In general, the amount of an additional active ingredient varies from about 0.0001% to about 20%, preferably from about 0.01% to about 10%, or even about 0.1% to about 5% by weight.

Other biologically active agents that can be used in the methods, kits, and compositions of the invention include antihistamines, anti-inflammatory agents, retinoids, anti-androgen agents, immunosuppressants, channel openers, antimicrobials, herbs (e.g., saw palmetto), extracts (e.g., Souhakuhi extract), vitamins (e.g., biotin), co-factors, psoralen, anthralin, and antibiotics.

Antihistamines

In certain embodiments, an antihistamine can be used in the compositions, methods, and kits of the invention. Useful antihistamines include, without limitation, Ethanolamines (e.g., bromodiphenhydramine, carbinoxamine, clemastine, dimenhydrinate, diphenhydramine, diphenylpyraline, and doxylamine); Ethylenediamines (e.g., pheniramine, pyrilamine, tripelennamine, and triprolidine); Phenothiazines (e.g., diethazine, ethopropazine, methdilazine, promethazine, thiethylperazine, and trimeprazine); Alkylamines (e.g., acrivastine, brompheniramine, chlorpheniramine, desbrompheniramine, dexchlorpheniramine, pyrrobutamine, and triprolidine); piperazines (e.g., buclizine, cetirizine, chlorcyclizine, cyclizine, meclizine, hydroxyzine); Piperidines (e.g., astemizole, azatadine, cyproheptadine, desloratadine, fexofenadine, loratadine, ketotifen, olopatadine, phenindamine, and terfenadine); and Atypical antihistamines (e.g., azelastine, levocabastine, methapyrilene, and phenyltoxamine). Both non-sedating and sedating antihistamines may be employed. Non-sedating antihistamines include loratadine and desloratadine. Sedating antihistamines include azatadine, bromodiphenhydramine; chlorpheniramine; clemizole;

cyproheptadine; dimenhydrinate; diphenhydramine; doxylamine; meclizine; promethazine; pyrilamine; thiethylperazine; and tripelennamine.

Other antihistamines suitable for use in the compositions, methods, and kits of the invention are acrivastine; ahistan; antazoline; astemizole; azelastine; bamipine; bepotastine; bietanautine; brompheniramine; carbinoxamine; cetirizine; cetoxime; chlorocyclizine; chloropyramine; chlorothen; chlorphenoxamine; cinnarizine; clemastine; clobenzepam; clobenztropine; clocinizine; cyclizine; deptropine; dexchlorpheniramine; dexchlorpheniramine maleate; diphenylpyraline; doxepin; ebastine; embramine; emedastine; epinastine; etymemazine hydrochloride; fexofenadine; histapyrrodine; hydroxyzine; isopromethazine; isothipendyl; levocabastine; mebhydroline; mequitazine; methafurylene; methapyrilene; metron; mizolastine; olapatadine; orphenadrine; phenindamine; pheniramine; phenyltoloxamine; p-methyldiphenhydramine; pyrrobutamine; setastine; talastine; terfenadine; thenyldiamine; thiazinamium; thonzylamine hydrochloride; tolpropamine; triprolidine; and tritoqualine.

Antihistamine analogs can be used in the compositions, methods, and kits of the invention. Antihistamine analogs include 10-piperazinylpropylphenothiazine; 4-(3-(2-chlorophenothiazin-10-yl)propyl)-1-piperazineethanol dihydrochloride; 1-(10-(3-(4-methyl-1-piperazinyl)propyl)-10H-phenothiazin-2-yl)-(9CI) 1-propanone; 3-methoxycyproheptadine; 4-(3-(2-Chloro-10H-phenothiazin-10-yl)propyl)piperazine-1-ethanol hydrochloride; 10,11-dihydro-5-(3-(4-ethoxycarbonyl-4-phenylpiperidino) propylidene)-5H-dibenzo(a,d)cycloheptene; aceprometazine; acetophenazine; alimemazin (e.g., alimemazin hydrochloride); aminopromazine; benzimidazole; butaperazine; carfenazine; chlorfenethazine; chlormidazole; cinprazole; desmethylastemizole; desmethylcyproheptadine; diethazine (e.g., diethazine hydrochloride); ethopropazine (e.g., ethopropazine hydrochloride); 2-(p-bromophenyl-(p'-tolyl)methoxy)-N,N-dimethyl-ethylamine hydrochloride; N,N-dimethyl-2-(diphenylmethoxy)-ethylamine methylbromide; EX-10-542A; fenethazine; fuprazole; methyl 10-(3-(4-methyl-1-piperazinyl)propyl)phenothiazin-2-yl ketone; lerisetron; medrylamine; mesoridazine; methylpromazine; N-desmethylpromethazine; nilprazole; northioridazine; perphenazine (e.g., perphenazine enanthate); 10-(3-dimethylaminopropyl)-2-methylthio-phenothiazine; 4-(dibenzo(b,e) thiepin-6(11H)-ylidene)-1-methyl-piperidine hydrochloride; prochlorperazine; promazine; propiomazine (e.g., propiomazine hydrochloride); rotoxamine; rupatadine; Sch 37370; Sch 434; tecastemizole; thiazinamium; thiopropazate; thioridazine (e.g., thioridazine hydrochloride); and 3-(10,11-dihydro-5H-dibenzo(a,d)cyclohepten-5-ylidene)-tropane.

Other compounds that are suitable for use in the compositions, methods, and kits of the invention are AD-0261; AHR-5333; alinastine; arpromidine; ATI-19000; bermastine; bilastin; Bron-12; carebastine; chlorphenamine; clofurenadine; corsym; DF-1-10550-1; DF-11062; DF-1111301; EL-301; elbanizine; F-7946T; F-9505; HE-90481; HE-90512; hivenyl; HSR-609; icotidine; KAA-276; KY-234; lamiakast; LAS-36509; LAS-36674; levocetirizine; levoprotiline; metoclopramide; NIP-531; noberastine; oxatomide; PR-881-884A; quisultazine; rocastine; selenotifen; SK&F-94461; SODAS-HC; tagorizine; TAK-427; temelastine; UCB-34742; UCB-35440; VUF-K-8707; Wy-49051; and ZCR-2060.

Still other compounds that can be used in the compositions, methods, and kits of the invention are described in U.S. Pat. Nos. 3,956,296; 4,254,129; 4,254,130; 4,282,233; 4,283,408; 4,362,736; 4,394,508; 4,285,957; 4,285,958; 4,440,933; 4,510,309; 4,550,116; 4,692,456; 4,742,175; 4,833,138; 4,908,372; 5,204,249; 5,375,693; 5,578,610; 5,581,011; 5,589,487; 5,663,412; 5,994,549; 6,201,124; and 6,458,958.

Antimicrobial Agents

In certain embodiments, an antimicrobial agent can be used in the compositions, methods, and kits of the invention. Useful antimicrobial agents include, without limitation, benzyl benzoate, benzalkonium chloride, benzoic acid, benzyl alcohol, butylparaben, ethylparaben, methylparaben, propylparaben, camphorated metacresol, camphorated phenol, hexylresorcinol, methylbenzethonium chloride, cetrimide, chlorhexidine, chlorobutanol, chlorocresol, cresol, glycerin, imidurea, phenol, phenoxyethanol, phenylethylalcohol, phenylmercuric acetate, phenylmercuric borate, phenylmercuric nitrate, potassium sorbate, sodium benzoate, sodium propionate, sorbic acid, and thiomersal.

The antimicrobial can be from about 0.05% to 0.5% by weight of the total composition, except for camphorated phenol and camphorated metacresol. For camphorated phenol, the preferred weight percentages are about 8% to 12% camphor and about 3% to 7% phenol. For camphorated metacresol, the preferred weight percentages are about 3% to 12% camphor and about 1% to 4% metacresol.

Anti-Inflammatory Agents

In certain embodiments, an antiinflammatory agent can be used in the compositions, methods, and kits of the invention. Useful antiinflammatory agents include, without limitation, Non-Steroidal Anti-Inflammatory Drugs (NSAIDs) (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin), COX-2 inhibitors (e.g., rofecoxib, celecoxib, valdecoxib, and lumiracoxib), and corticosteroids (e.g., alclometasone dipropionate, amcinonide, betamethasone dipropionate, betamethasone valerate, clobetasol propionate, desonide, desoximetasone, dexamethasone, diflorasone diacetate, flucinolone acetonide, flumethasone, fluocinonide, flurandrenolide, halcinonide, halobetasol propionate, hydrocortisone butyrate, hydrocortisone valerate, methylprednisolone, mometasone furoate, prednisolone, or triamcinolone acetonide).

Immunosuppressants

In certain embodiments, a nonsteroidal immunosuppressant can be used in the compositions, methods, and kits of the invention. Suitable immunosuppressants include cyclosporine, tacrolimus, rapamycin, everolimus, and pimecrolimus.

Cyclosporines

The cyclosporines are fungal metabolites that comprise a class of cyclic oligopeptides that act as immunosuppressants. Cyclosporine A is a hydrophobic cyclic polypeptide consisting of eleven amino acids. It binds and forms a complex with the intracellular receptor cyclophilin. The cyclosporine/cyclophilin complex binds to and inhibits calcineurin, a $Ca^{2+}$-calmodulin-dependent serine-threonine-specific protein phosphatase. Calcineurin mediates signal transduction events required for T-cell activation (reviewed in Schreiber et al., Cell 70:365-368, 1991). Cyclosporines and their functional and structural analogs suppress the T cell-dependent immune response by inhibiting antigen-triggered signal transduction. This inhibition decreases the expression of proinflammatory cytokines, such as IL-2.

Many different cyclosporines (e.g., cyclosporine A, B, C, D, E, F, G, H, and I) are produced by fungi. Cyclosporine A is a commercially available under the trade name NEORAL from Novartis. Cyclosporine A structural and functional analogs include cyclosporines having one or more fluorinated amino acids (described, e.g., in U.S. Pat. No. 5,227,467); cyclosporines having modified amino acids (described, e.g., in U.S. Pat. Nos. 5,122,511 and 4,798,823); and deuterated cyclosporines, such as ISAtx247 (described in U.S. Patent Application Publication No. 2002/0132763 A1). Additional cyclosporine analogs are described in U.S. Pat. Nos. 6,136, 357, 4,384,996, 5,284,826, and 5,709,797. Cyclosporine analogs include, but are not limited to, D-Sar ($\alpha$-SMe)$^3$ Val$^2$-DH-Cs (209-825), Allo-Thr-2-Cs, Norvaline-2-Cs, D-Ala(3-acetylamino)-8-Cs, Thr-2-Cs, and D-MeSer-3-Cs, D-Ser (O—CH$_2$CH$_2$—OH)-8-Cs, and D-Ser-8-Cs, which are described in Cruz et al., *Antimicrob. Agents Chemother.* 44:143 (2000).

Tacrolimus

Tacrolimus and tacrolimus analogs are described by Tanaka et al. (*J. Am. Chem. Soc.,* 109:5031 (1987)) and in U.S. Pat. Nos. 4,894,366, 4,929,611, and 4,956,352. FK506-related compounds, including FR-900520, FR-900523, and FR-900525, are described in U.S. Pat. No. 5,254,562; O-aryl, O-alkyl, O-alkenyl, and O-alkynylmacrolides are described in U.S. Pat. Nos. 5,250,678, 532,248, 5,693,648; amino O-aryl macrolides are described in U.S. Pat. No. 5,262,533; alkylidene macrolides are described in U.S. Pat. No. 5,284, 840; N-heteroaryl, N-alkylheteroaryl, N-alkenylheteroaryl, and N-alkynylheteroaryl macrolides are described in U.S. Pat. No. 5,208,241; aminomacrolides and derivatives thereof are described in U.S. Pat. No. 5,208,228; fluoromacrolides are described in U.S. Pat. No. 5,189,042; amino O-alkyl, O-alkenyl, and O-alkynylmacrolides are described in U.S. Pat. No. 5,162,334; and halomacrolides are described in U.S. Pat. No. 5,143,918.

Tacrolimus is extensively metabolized by the mixed-function oxidase system, in particular, by the cytochrome P-450 system. The primary mechanism of metabolism is demethylation and hydroxylation. While various tacrolimus metabolites are likely to exhibit immunosuppressive biological activity, the 13-demethyl metabolite is reported to have the same activity as tacrolimus.

Pimecrolimus

Pimecrolimus is the 33-epi-chloro derivative of the macrolactam ascomyin. Pimecrolimus structural and functional analogs are described in U.S. Pat. No. 6,384,073.

Rapamycin

Rapamycin structural and functional analogs include mono- and diacylated rapamycin derivatives (U.S. Pat. No. 4,316,885); rapamycin water-soluble prodrugs (U.S. Pat. No. 4,650,803); carboxylic acid esters (PCT Publication No. WO 92/05179); carbamates (U.S. Pat. No. 5,118,678); amide esters (U.S. Pat. No. 5,118,678); biotin esters (U.S. Pat. No. 5,504,091); fluorinated esters (U.S. Pat. No. 5,100,883); acetals (U.S. Pat. No. 5,151,413); silyl ethers (U.S. Pat. No. 5,120,842); bicyclic derivatives (U.S. Pat. No. 5,120,725); rapamycin dimers (U.S. Pat. No. 5,120,727); O-aryl, O-alkyl, O-alkyenyl and O-alkynyl derivatives (U.S. Pat. No. 5,258, 389); and deuterated rapamycin (U.S. Pat. No. 6,503,921). Additional rapamycin analogs are described in U.S. Pat. Nos. 5,202,332 and 5,169,851.

Retinoids

In certain embodiments, a retinoid can be used in the compositions, methods, and kits of the invention. Useful retinoids include, without limitation, 13-cis-retinoic acid, adapalene, all-trans-retinoic acid, and etretinate.

Channel Openers

In certain embodiments, a channel opener can be used in the compositions, methods, and kits of the invention. Useful channel openers include, without limitation, minoxidil, diazoxide, and phenyloin.

Anti-Androgens

In certain embodiments, an anti-androgen can be used in the compositions, methods, and kits of the invention. Useful anti-androgens include, without limitation, finasteride, flutamide, diazoxide, 11alpha-hydroxyprogesterone, ketoconazole, RU58841, dutasteride, fluridil, QLT-7704, and anti-androgen oligonucleotides.

Antibiotics

In certain embodiments, an antibiotic can be used in the compositions, methods, and kits of the invention. Useful antibiotics include, without limitation, penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, and trimethoprim.

Reepithelialization

In one aspect of this invention, the compositions of the invention are administered to a subject's skin (examples of the skin location are the head, for example, the scalp, the eyebrow, or a scarred region) while the skin is in a state of reepithelialization. Reepithelialization is the process that occurs during formation of a new epidermis and can be characterized for the purposes of this invention by the lack of hair follicle morphogenesis (e.g., if within the tissue some cells are in the pre-placode stage of hair follicle formation), an embryonic-like state, in which the follicle regenerates, or by lack of a stratum corneum.

State of Reepithelialization

Reepithelialization can be detected through inspection of the new epidermis where covering of the wound area by keratinocytes indicates reepithelialization. The presence of a keratinocytes can be seen with the naked eye as a white, glossy, shiny surface that gradually covers the open wound. Using a confocal microscope, keratinocytes can be visualized as a sheet of "cobblestone" looking cells. Reepithelialization can also be detected through the measurement of trans epidermal water loss (TEWL). TEWL decreases when the epithelial barrier is restored. Confocal scanning laser microscopy and/or optical coherence tomography can also be used to detect the state of reepithelialization, where the presence of keratinocytes indicates reepithelialization.

The presence of a stratum corneum can be determined though visual inspection, direct observation of papillary blood vessels using a capillary microscope, or through a colorimetric redox reaction of a compound that reacts in the presence of live cells. For example, 0.01% nitrazine yellow applied to the skin will remain yellow if a stratum corneum is present, and will turn greenish brown if not. In another example 0.01% bromcresol purple applied to the skin will stay yellow if the stratum corneum is present and will turn purple if the stratum corneum is not present.

The area of reepithelialization can be, for example, between 0-2 millimeters (mm) in width (e.g., 1 mm, 2 mm, 3 mm, or greater), 0-2 centimeters (cm) in width (e.g., 1 cm, 1.5 cm, and 2.0 cm) or greater. Optionally, the area of reepithelialization can be interfollicular.

In some aspects of the invention, it is desirable to administer the compounds of the invention at a particular phase of reepithelialization. Stages at which compounds of the invention may preferably be administered and/or activated include periods:
- after completion of the reepithelialization process (e.g., 3-12 days, or 9-11 days after having disrupted the skin),
- after or during the establishment of a stem cell population that will develop into a regenerated hair follicle (Ito et al, *Nature* 447, 316-320, May 2007),
- prior to the expression of hair follicle differentiation markers KRT17 and Lef1 for several days after wound closure (Ito et al, *Nature* 447, 316-320, May 2007),
- after or during expression of one or more proteins including KRT17, Lef-1, alkaline phosphatase, Wnt10b, and Shh (Ito et al, *Nature* 447, 316-320, May 2007),
- characterized by the absence of K10 expression (which is expressed in normal epidermis) and/or induction of expression of K16 and K17 (which are not expressed in normal epidermis) (Patel et al, *Journal of Investigative Dermatology*, 126, 2006),
- characterized by the elevation of one or more transcription factors including AP-1 and NF-κB, primary cytokines IL-1β and TNF-α, and matrix metalloproteases (Karimipour et al, Journal of the American Academy of Dermatology, 52, Issue 2, 2005),
- characterized by histologic changes (Freedman et al, Dermatologic Surgery, 27 Issue 12, December 2001), including, for example:
  thickening of the epidermis and dermis,
  flattening of rete pegs,
  vascular ectasia,
  perivascular inflammation,
  hyalinization of the papillary dermis with newly deposited collagen and elastic fibers,
  change in orientation, density, or packing of collagen and other structures,
- characterized by detachment of the scab. Depending on the depth of the abrasion process, it may be desirable for the compounds of the invention to be administered or activated prior to or after the detachment of a scab. Alternatively, hair follicles may start to form before the scab falls off, in the case of, for example, dermabrasion.

Alternatively the compounds of the invention can be administered prior to epidermal disruption. In such embodiments, the compound may be formulated for controlled release such that the therapeutically active compound is released during reepithelialization or during a particular phase of reepithelialization (e.g., as described above. The compound may also be formulated such that it becomes activated by an endogenous or exogenous stimulus (e.g., as described below).

Induction of Reepithelialization

The state of reepithelialization can be induced. Methods of inducing this state include the disruption of the subject's skin at the location where the compounds of the invention are going to be administered. Disruption can be achieved through abrasion (e.g., the rubbing or wearing away of skin), or through any method that results in disturbing the intactness of the epidermis or epidermal layer including burning (e.g., by inducing a sunburn) or perforating the epidermis or epidermal-layer. The disruption can either result in partial or complete removal of the epidermal layer at the intended location.

The disruption of the epithelial layer can be accomplished, for example, through mechanical, chemical, electromagnetic, electrical, or magnetic means. Mechanical means can be achieved through the use of, for example, sandpaper, a felt wheel, ultrasound, supersonically accelerated mixture of saline and oxygen, tape-stripping, or peels.

Chemical means of disruption of the epidermis can be achieved, for example, using phenol, trichloracetic acid, or ascorbic acid.

Electromagnetic means of disruption of the epidermis can be achieved, for example, by the use of a laser capable of inducing trans-epithelial injury (e.g., a Fraxel laser, a CO2 laser, or an excimer laser). Disruption can also be achieved through, for example, the use of visible, infrared, ultraviolet, radio, or X-ray irradiation.

Electrical or magnetic means of disruption of the epidermis can be achieved, for example, through the application of an electrical current or through electroporation. Electric or magnetic means can also include the induction of an electric or a magnetic field. For example, an electrical current can be induced in the skin by application of an alternating magnetic field. A radiofrequency power source can be coupled to a conducting element, and the currents that are induced will heat the skin, resulting in an alteration or disruption of the skin. In this embodiment, no external energy transfer is needed in order to cause a disruption Any of the previously mentioned means of disruption can be used to induce for example, a burn, excision, or microdermabrasion.

Optionally, the skin, following the epidermal disruption, is not contacted for a period of time with any substance (e.g., ointment, a bandage, or a device) that is normally administered to an abrasion or wound to prevent infection. Here the skin is not contacted with any substance until, for example, the epidermal disruption has healed (e.g., any time between 2 days and 3 weeks). Alternatively, the skin can be contacted with a cast or bandage (e.g., resulting in increased blood flow to the disrupted skin or decreased transdermal water loss or decreased mass transfer of gases into the skin and from the skin (e.g. oxygen, carbon dioxide, water vapor), decreased heat transfer from the skin (e.g. resulting in an increased temperature of the skin surface) or increased pressure on the skin.

Prior to disruption, the skin can depilated or epilated. The depilation or epilation can be accomplished through, for example, waxing, plucking, an abrasive material, a laser, electrolysis, a mechanical device, or thioglycolic acid.

The disruption of the epidermis can be induced between 3-12 days (e.g., 4-12, 5-12, 4-11, 6-11, 6-10, 6-9, 7-8, 5-11, 5-10, or 7-10 days) prior to the addition of the compositions of the invention.

Any of the above-described methods may be used to remove a precise amount of epidermal tissue. For example, the methods of abrasion described herein may be used to achieve:

Removal of the stratum corneum through removal of the first 10-30 µm of dead skin cells.

Removal of the stratum corneum and part or all of the epidermis by removing the first 30-100 µm of the skin. This is not deep enough to remove the sebaceous gland, bulge, or hair papilla of existing follicle structures.

Removal of the stratum corneum, the full epidermis, and part of the dermis down to approximately 500 µm. This process removes most of the sebaceous glands, which are at a depth beneath 500 µm.

Removal of the stratum corneum, the full epidermis, and part of the dermis down to approximately 800 µm. This process removes most of the glands, and the bulge regions, which are at a depth beneath 800 µm. (Dunkin et al., *Plastic Reconstructive Surgery,* 119 (6), May 2007)

Removal of the stratum corneum, the full epidermis, and part of the dermis down to approximately 2000-4000 µm. This process removes the sebaceous glands, the bulge regions, and most of the hair papillas, which are at a depth beneath 2000 µm.

Removal of the stratum corneum, the full epidermis, and the full dermis resulting in removal of up to 5 to 7 mm of skin. This process removes all the structures of the follicles, including the sebaceous gland, bulge, and papilla.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1

Depilation and Epidermal Abrasion Causes De Novo Hair Follicle Formation

Depilation and epidermal abrasion. Mice were anesthetized with an injection of sodium pentobarbital before the hair on the back was clipped and depilated with Nair (Carter-Wallace, New York, N.Y.), then epidermis was removed using a rotating felt wheel as described by Argyris T, *J. Invest. Dermatol.* 75: 360 (1980). After scrubbing with 70% ethanol and drying under an incandescent lamp, the basal and suprabasal layers in an area of 1.5 cm$^2$/cm of the inter-follicular epidermis were removed by careful abrasion with a felt wheel mounted on a Dremel Moto-tool (Racine, Wis.). After abrasion, the skin was shiny and smooth, and there was no blood. One day later, the abraded area was covered by a fibrin crust, which fell off after 3-7 days, exposing the newly regenerated epidermis. A group of control mice was sacrificed immediately after abrasion to confirm microscopically the complete removal of the interfollicular epidermis.

Immunohistochemistry. Skin samples were fixed in PBS-buffered 10% formalin. Six-micron thick paraffin sections were cut and stained, where applicable, with antibodies.

BrdU labeling. The protocol described by Bickenbach and colleagues (Bickenbach et al, Cell Tiss Kinet 19: 325-333, 1986; Bickenbach et al, Exp Cell Res 244, 184-195, 1998) was used. Mice were injected with 50 milligrams per kilogram (mg/kg) bodyweight 5-bromo-2'-deoxyuridine (BrdU) every 12 hours for a total of four injections.

Figure 2:
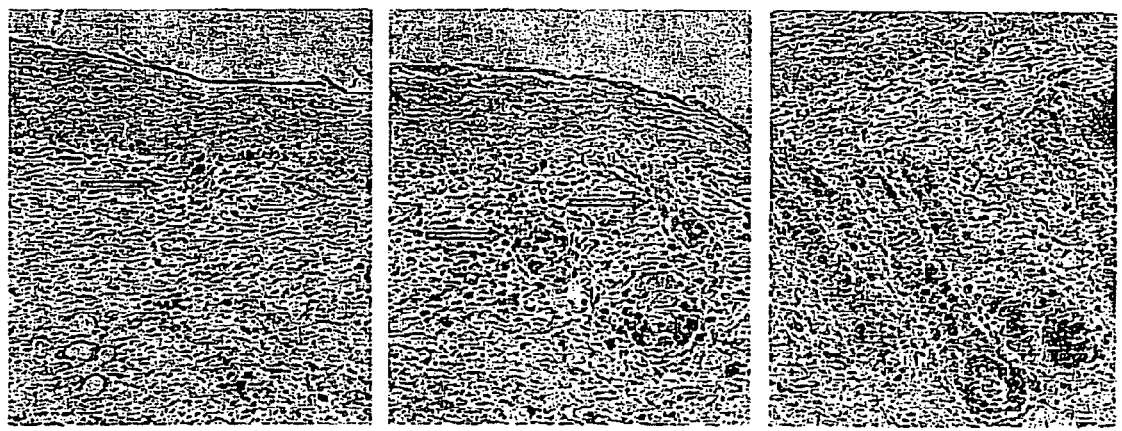
FIG. 2. BrdU labeling of HF following epidermal abrasion. HF at progressive stages of development are depicted in the left, center, and right panels.

Results: An area of the backs of 50-day old mice was subjected to depilation and removal of the epidermis using a rotating felt wheel. Fifteen days later, HF placodes, hair germs and other signs of follicle neogenesis were present (FIG. 1; arrow indicates a hair germ). Morphology of the follicles was similar to embryonic follicle development. To further characterize proliferation in the new follicles, the skin was labeled with BrdU 60 minutes before sacrifice. As depicted in FIG. 2, the proliferation pattern was similar to developing follicles in the embryo.

These findings demonstrate that (a) disruption of the epidermis causes generation of new HF, and that this generation of new HF can occur (b) in adult subjects and (c) during telogen (50-day-old mice are in the second telogen stage of the hair cycle).

Example 2

Induction of a Large Excisional Wound, but not a Small Punch Wound, Causes De Novo Hair Follicle Formation Punch wound and excisional wound induction. The backs of 21-day-old mice were depilated as described for Example 1 and sterilized with alcohol, followed by 1% iodine solution. Punch wounds, 4 mm in diameter, were induced using a dermal biopsy punch, down to, but not through, the muscle fascia. Excisional wounds were full thickness and 1 cm in diameter; skin and panniculus carnosus was excised using fine surgical scissors.

Figure 3:
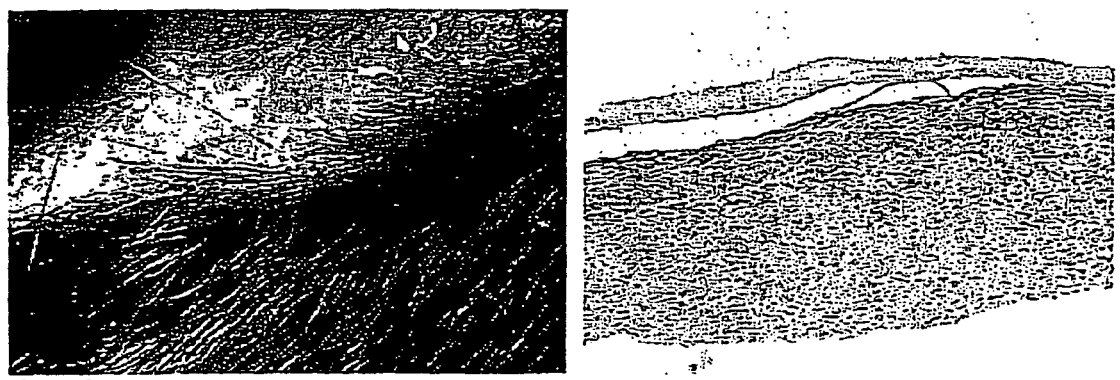
FIG. 3. The wound site did not contain HF immediately after re-epithelialization. Top view (left panel) and tissue section (right panel) of the site 10 days after wound induction.
Figure 4:
FIG. 4. Appearance of hair germs 12 days after wound induction. Arrow indicates hair germ.
Figure 5:
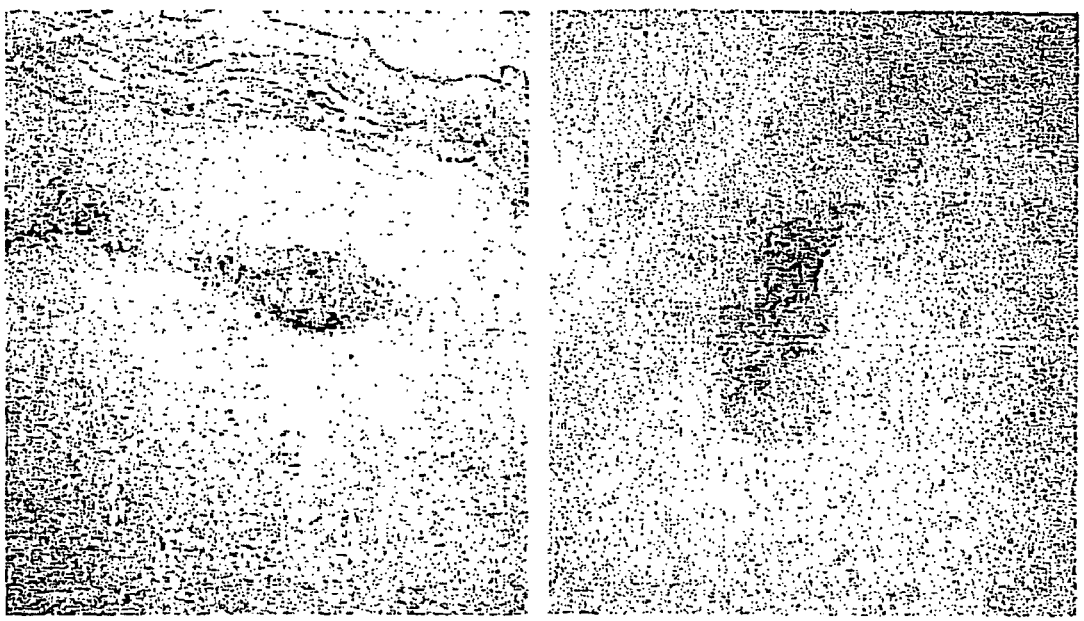
FIG. 5. Epidermal Disruption-Induced HF neogenesis (EDIHN)-induced hair germs express K17. Two different hair germs are depicted in the left and right panels.
Figure 6:
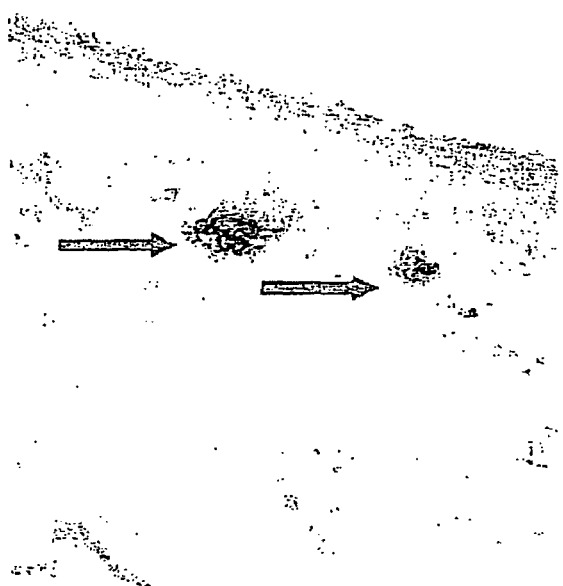
FIG. 6. EDIHN-induced hair germs contain dermal papilla (DP) cells, as evidenced by alkaline phosphatase (AP) staining. Arrows indicate DP cells. Left panel: hair germs. Right panel: HF at a further developmental stage.
Figure 6:
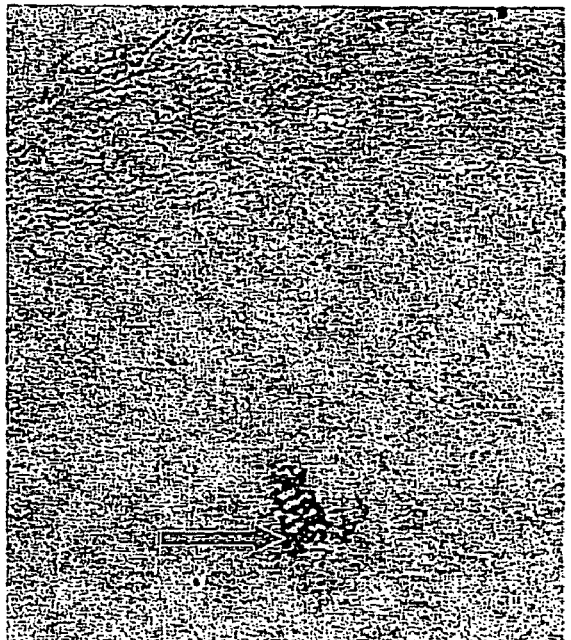

Results: To test whether wounding could induce HF formation, punch wounds or excisional wounds were induced in mice. Both types of wounds exhibited contraction and re-epithelialization following wound induction; however, unlike the mice receiving punch wounds, the mice receiving excisional wounds also exhibited scar formation within 10 days of wound induction (FIG. 3, left panel). No follicles were evident at this time point (FIG. 3, right panel). 12 days after wound induction, hair germs, with similar morphology to fetal hair germs, were observed in the wound site, following BrdU pulse labeling (FIG. 4). Several markers were used to verify that the observed structures were HF. The structures exhibited staining with anti-keratin 17 (K 17), an HF marker (FIG. 5), and staining with anti-alkaline phosphatase at the 12 day time point verified that the structures had dermal papilli containing fibroblasts, as expected for HF (FIG. 6; HF at earlier and later stages are depicted in the left and right panels, respectively).

Figure 7:
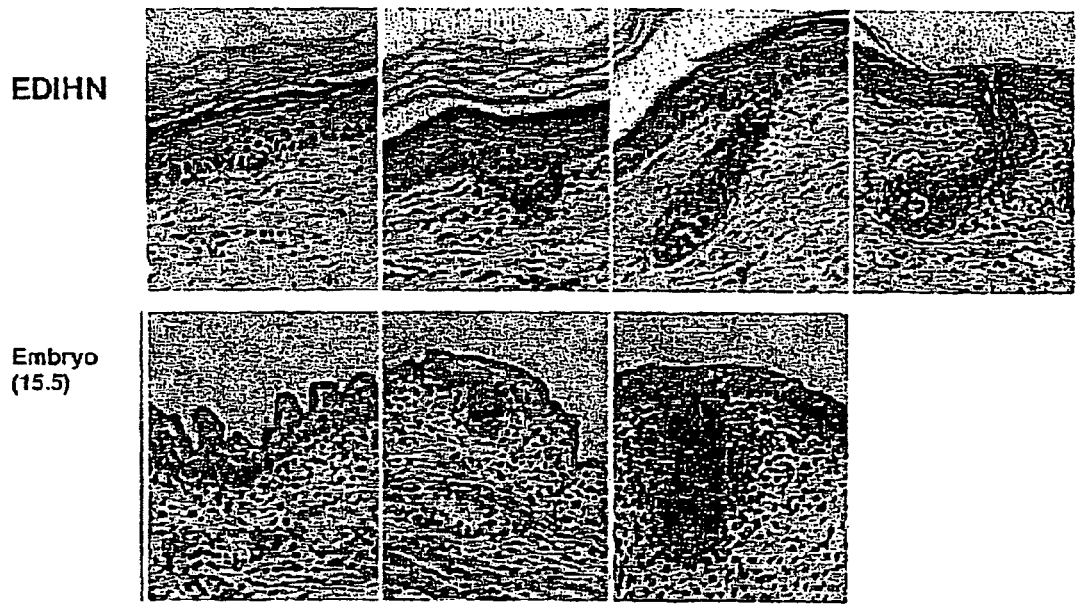
FIG. 7. Histological comparison between EDIHN-induced and embryonic HF. Top left, second from left, third from left, and right panels: Progressive stages of EDIHN-induced HF development. Bottom left, center, and right panels: Progressive stages of and embryonic HF development.
Figure 8:
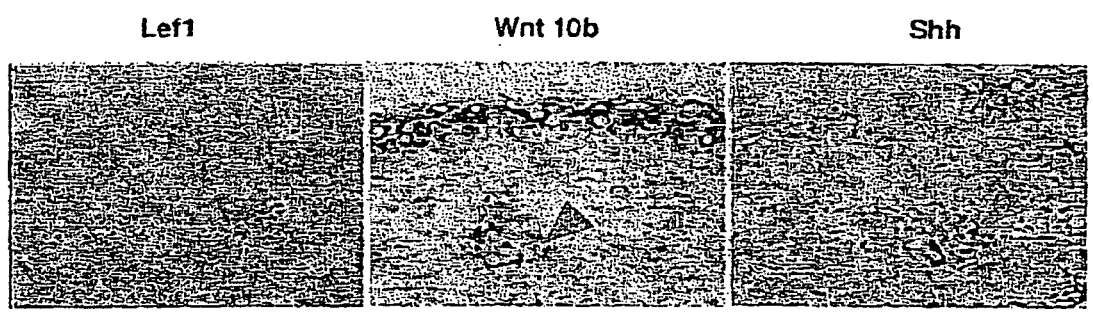
FIG. 8. Induction of several markers of embryonic HF development, Lef1 (left-panel), wingless/int (Wnt) 10b (center panel), and sonic hedgehog (Shh; right panel), by EDIHN. HF structures are indicated by arrowheads.
Figure 9:
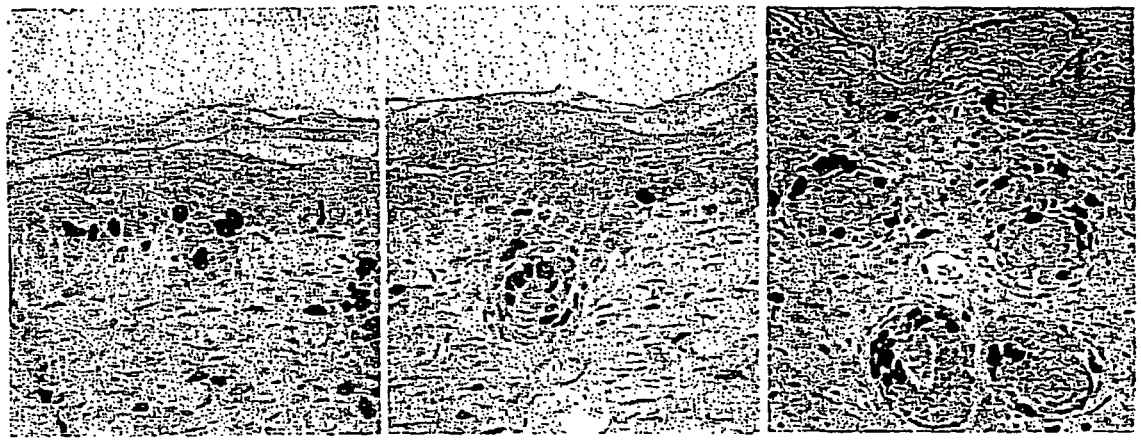
FIG. 9. Proliferative activity during EDIHN, as evidenced by BrdU pulse-labeling. Progressive stages of HF development are depicted in the left, center, and right panels.
Figure 10:
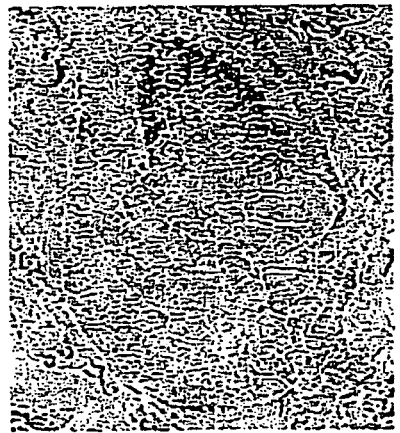
FIG. 10. Induction of HF markers S100A3 (left panel; tissue section parallel to HF axis) and S100A6 (right panel; cross-sectional view of follicle) by EDIHN.
Figure 10:
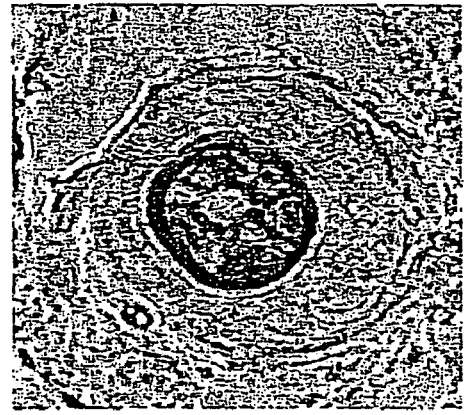

The HF generated by wound induction were further characterized by morphological comparison to embryonic HF, following BrdU staining; a clear correspondence in morphology was observed at various stages (FIG. 7). In addition, several markers of embryonic HF development, namely Lef1, wingless/int (Wnt) 10b, and sonic hedgehog (Shh), were also induced in the epidermal disruption-induced HF neogenesis (EDIHN) (FIG. 8). Additional BrdU staining (FIG. 9) and staining for HF markers S100A3 and S100A6 (FIG. 10; left panel: tissue section parallel to HF axis; right panel: cross-sectional view of follicle) provided further verification that the development of the EDIHN follicles closely paralleled embryonic HF development.

These findings provide further evidence that disruption of the epidermis causes generation of new HF, and that this generation of new HF can occur (b) in adult subjects and (c) during telogen (21-day-old mice are in the first telogen stage of the hair cycle).

Example 3

EDIHN-Induced Hair Follicles Generate Hairs

Figure 11:
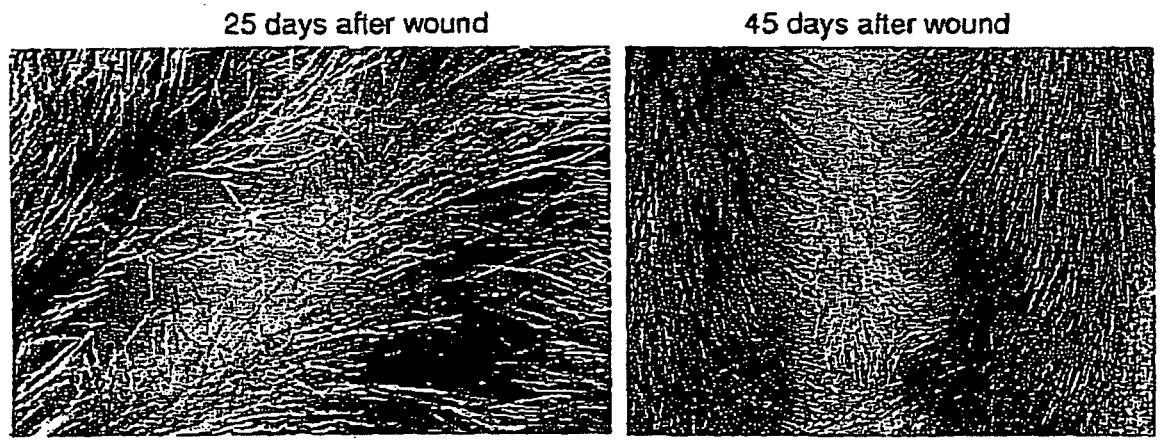
FIG. 11. New hair growth 25 days (left panel) and 45 days (right panel) after wound induction.

At 25 and 45 days after wound induction, wound sites contained new hairs (FIG. 11, left and right panels, respectively). New hairs appeared to lack pigmentation, except when the wnt pathway was inhibited, using Dkk-1 (Dickkopf-1) during the first nine days after wounding (see Example 10).

These findings indicate that EDIHN-induced HF function normally; i.e., are capable of generating hairs.

Example 4

EDIHN Hair Follicles Retain the Ability to Enter into Cyclical Hair Growth

BrdU labeling. 50 mg/kg bodyweight BrdU (Sigma) was injected twice per day for 3 days beginning 20 days after wounding. BrdU was detected 40 days after wounding (17 day chase).

Figure 12:
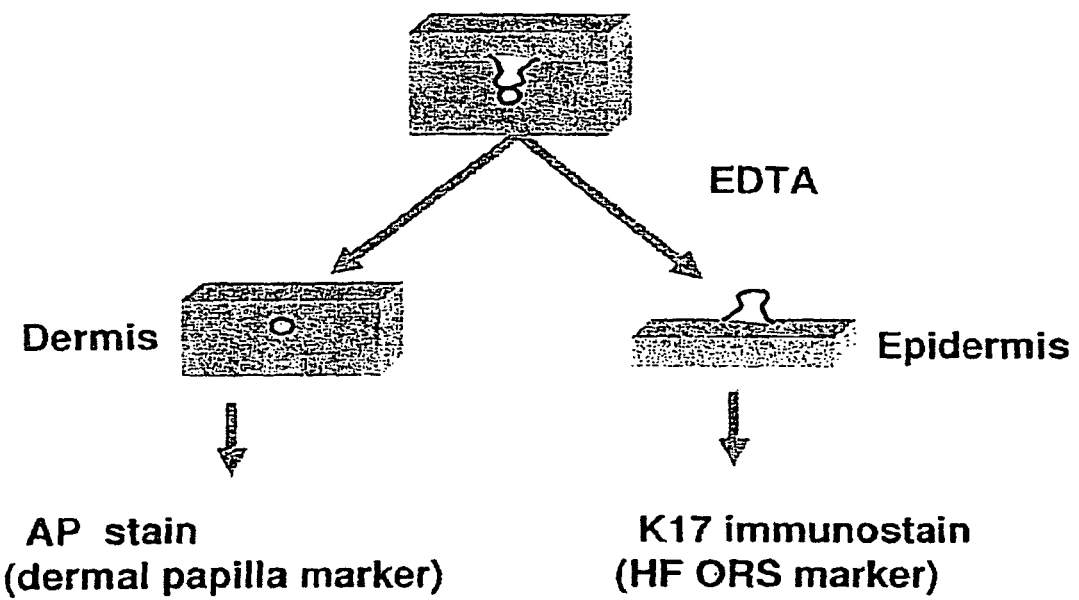
FIG. 12. Schematic of whole-mount EDIHN assay.

Whole mounting and immunofluorescence. HF whole mounts were obtained by incubating fresh skin with EDTA (20 mM in PBS) at 37° C. overnight, then separating the epidermis and dermis. Epidermis was then fixed in 10% formalin for 10 min, room temperature (RT). Dermis was fixed in acetone overnight, RT. After rinsing with PBS, whole mounts were stained with antibodies for immunohistochemistry (schematically depicted in FIG. 12) and were imaged using a Leica confocal microscope.

Figure 13:
FIG. 13. Repopulation of stem cells in the bulge of EDIHN-induced HF, as evidenced by retention of BrdU label following a chase period. Left panel: lower magnification: 50×. Right panel: higher magnification: 400×.
Figure 14A:
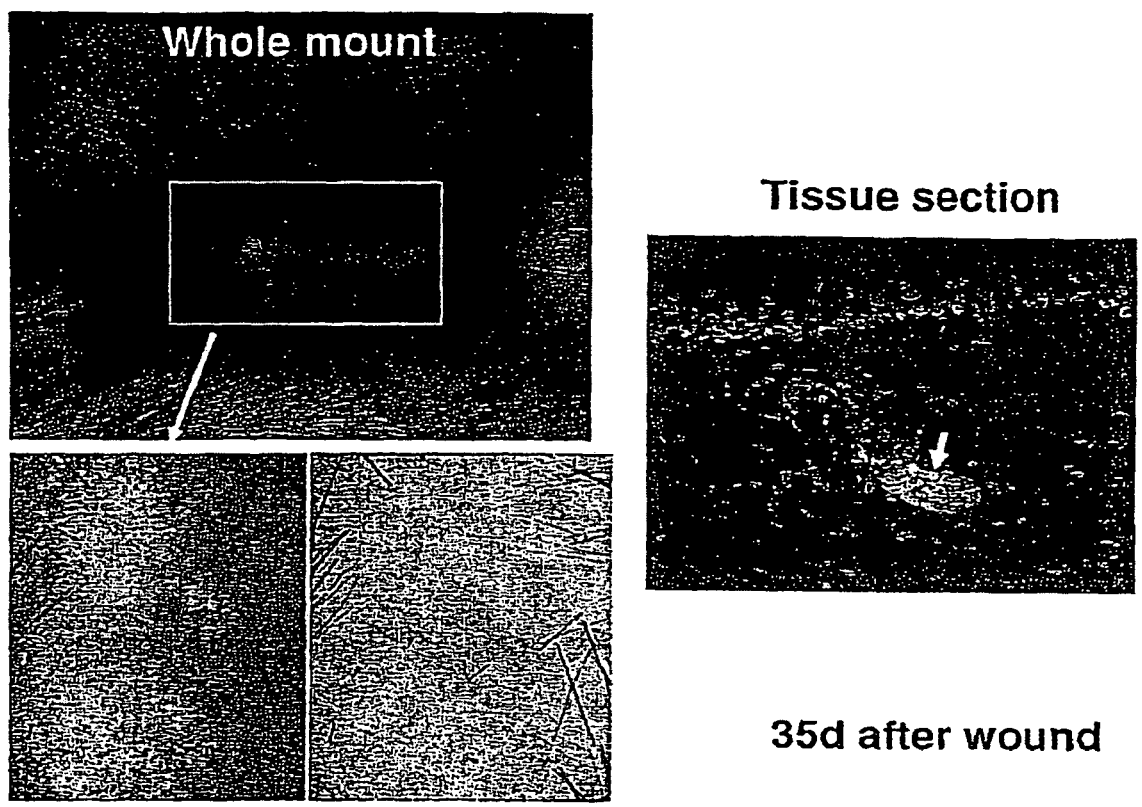
FIG. 14A. Stem cells in EDIHN-induced HF express K15. Left top panel: Top view of wound site. Bottom, far left panel: epidermis whole mount; bottom, second from left panel: same as [bottom, far left] panel but viewed under white light; right panel: tissue sections.

Results: To determine whether EDIHN-induced HF contain normal levels of HF stem cells, mouse skin was examined for the presence of label-retaining cells at 21 days after wound induction. Retention of BrdU during a long chase period is, under these conditions, one of the hallmarks of HF stem cells. Normal numbers and placement of label-retaining cells (in the bulge of the HF) were observed (FIG. 13). To verify that the label-retaining cells were HF stem cells, K15-eGFP mice were utilized. In these mice, eGFP (enhanced green fluorescent protein) is expressed from the K15 promoter; thus, expression of eGFP identifies HF stem cells. As depicted in FIG. 14A, eGFP-expressing cells were observed in tissue sections (right side) of newly formed hair follicles 35 days following wound induction. eGFP-expressing cells were also seen in the epidermis whole mounts (bottom, far left panel) indicating the conversion of epidermal cells into cells with hair follicle stem cell characteristics. ([bottom, second from left] panel is same as [bottom, far left] panel but viewed under white light) This finding shows that the observed label-retaining cells exhibited HF stem cell properties.

Figure 14B:
FIG. 14B. Neogenesis HF proceed to next hair cycle.

To determine whether EDIHN-induced HF cycle normally, mounts were prepared from additional mice at 35, 38 and 45 days after wounding. As depicted in FIG. 14B, the EDIHN-induced HF entered the resting phase, telogen, and then re-entered a new anagen stage.

Figure 15:
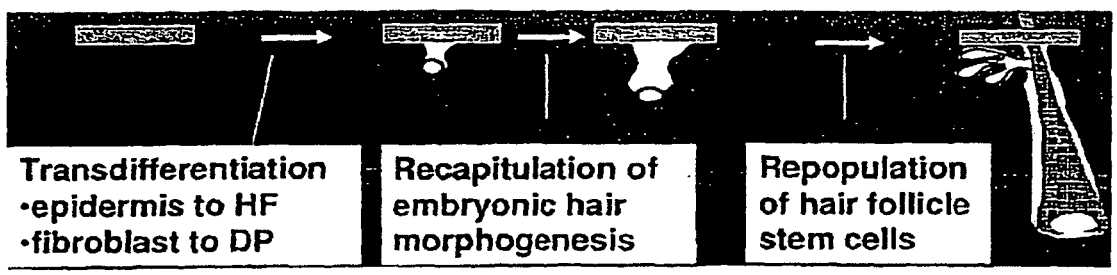
FIG. 15. Schematic of creation of new HF by EDIHN.

In summary, the findings of this Example show that EDIHN-induced HF contain HF stem cells, as do embryonically generated HF. The presence of the HF stem cells shows that EDIHN-induced HF retain the ability to enter into cyclical hair growth in the same manner as embryonically generated HF. The findings also show that wounding induces epidermal cells to assume a hair follicle stem cell state (expressing K15-eGFP). This model is shown schematically in FIG. 15. The findings of Examples 2, 3, and 4 show that EDIHN-induced HF are fully functional and thus able to restore hair growth to a subject in need.

Example 5

EDIHN Induces New Hair Follicles in Mice at the Telogen Stage of the Hair Cycle

Figure 16:
FIG. 16. No new HF are evident 11 days after wound induction in 21-day-old mice. Top panel: macroscopic examination; bottom left panel: AP staining of the dermis; bottom right panel: K17 staining of the epidermis.
Figure 16:
Figure 17:
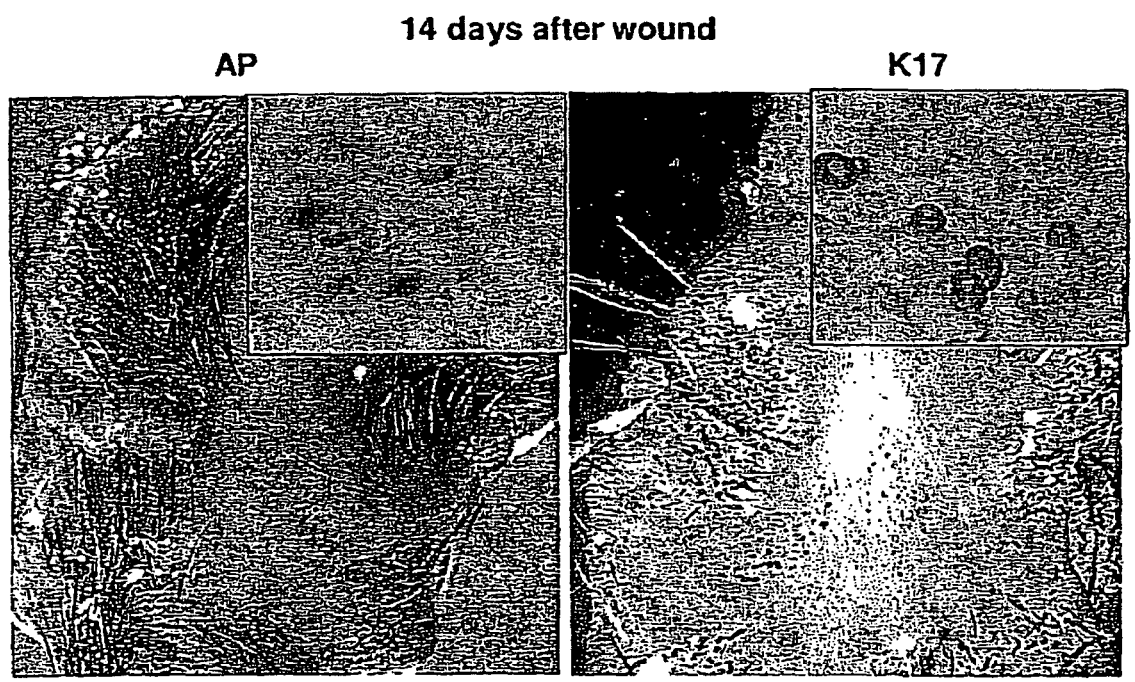
FIG. 17. 14 days after wound induction, new HF have begun to form as evidenced by AP staining of the dermis (left panel) and K17 staining of the epidermis (right panel). Main panels: 10× magnification. Inserts: 80× magnification.
Figure 18:
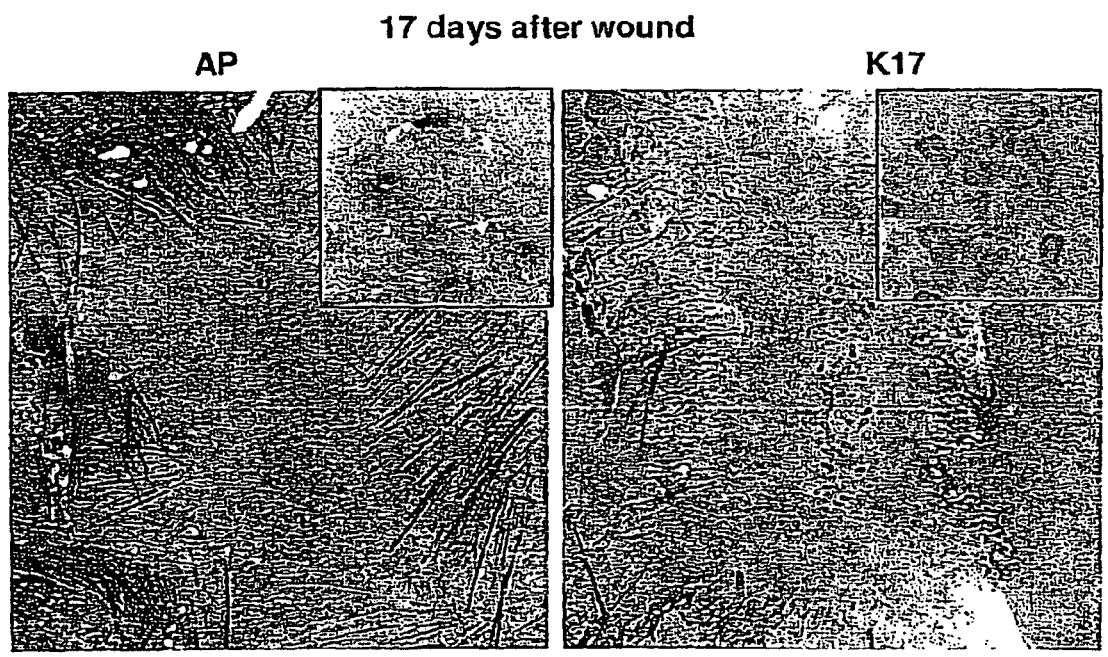
FIG. 18. 17 days after wound induction, new HF are more developed. Left panel: AP staining of the dermis; right panel: K17 staining of the epidermis. Main panels: 10× magnification. Inserts: 80× magnification.

To determine whether EDIHN was induced new hair follicles in mice wounded at the telogen stage of the hair cycle, 21-day-old mice were subjected to EDIHN using a 1-cm excisional wound, as described in Example 2. Skin was then examined by whole-mount assay for indications of new HF. As depicted in FIG. 16, after 11 days, new HF were not evident by macroscopic examination (top panel), AP staining of the dermis (bottom left panel), or K17 staining of the epidermis (bottom right panel). After 14 days, as depicted in FIG. 17, dermal papilla cells were detected in the dermis (left panel) and HF stem cells in the epidermis (right panel), demonstrating that new follicles were being formed. After 17 days, the new follicles were more developed, as shown by examination of the dermis and epidermis (FIG. 18, left and right panels, respectively). This method induced formation of an average of 49 new follicles in the wound, a number that was consistent over three separate experiments, as depicted in Table 2.

To determine whether EDIHN was induced new hair follicles in mice wounded at the telogen stage of the hair cycle, 21-day-old mice were subjected to EDIHN using a 1-cm excisional wound, as described in Example 2. Skin was then examined by whole-mount assay for indications of new HF. As depicted in FIG. 16, after 11 days, new HF were not evident by macroscopic examination (top panel), AP staining of the dermis (bottom left panel), or K17 staining of the epidermis (bottom right panel). After 14 days, as depicted in FIG. 17, dermal papilla cells were detected in the dermis (left panel) and HF stem cells in the epidermis (right panel), demonstrating that new follicles were being formed. After 17 days, the new follicles were more developed, as shown by examination of the dermis and epidermis (FIG. 18, left and right panels, respectively). This method induced formation of an average of 49 new follicles in the wound, a number that was consistent over three separate experiments, as depicted in Table 2.

TABLE 2

Results of three separate experiments performed on 21-day-old mice.

| Sample | Expt 1 | Expt 2 | Expt 3 | | |
|---|---|---|---|---|---|
| 1 | 24 | 70 | 55 | | |
| 2 | 29 | 52 | 25 | | |
| 3 | 27 | 85 | 53 | | |
| 4 | 102 | 25 | 80 | | |
| 5 | 53 | 27 | 23 | Avg of expts | Std dev of expts |
| Average | 47 | 51.8 | 47.2 | 48.67 | 2.71 |
| Std dev | 32.8 | 26.3 | 23.7 | | |

The findings of this Example demonstrate that EDIHN is capable of inducing formation of new HF in mice at the telogen stage of the hair cycle, despite that fact that these mice do not contain HF at the anagen stage during wounding.

Example 6

In Adult Mice, Induction of Anagen Increases the Efficiency of EDIHN

The experiment described in Example 5 was repeated with mice of different ages, and therefore at different stages of the hair cycle. To ensure that wound scarring occurred, larger wounds were in induced in the older mice. As depicted in Table 3, adult mice at telogen, such as 8-week-old mice, exhibited lower efficiencies of HF formation by EDIHN.

TABLE 3

Efficiency of HF formation by EDIHN in adult mice at various stages of the hair cycle.

| Age | Wound size | Days after wound | Mice exhibiting EDIHN | Hair cycle |
|---|---|---|---|---|
| 3 wk | 1 cm | 20 | 25/25 (100%) | Telogen |
| 4 wk | 1 cm | 20 | 5/5 (100%) | Early anagen |
| 5 wk | 1 cm | 20 | 1/2 (50%) | Anagen |
| 8 wk | 1.5 cm | 30 | 16/35 (46%) | Telogen |
| 14 wk | 1.5 cm | 30 | 1/2 (50%) | N/A* |
| 20 wk | 1.5 cm | 30 | 2/2 (100%) | N/A* |

*The second telogen lasts approximately 40 days in mice. Thus, 14-week-old and 20-week-old mice contained a mixture of telogen and anagen HF.

Figure 19:
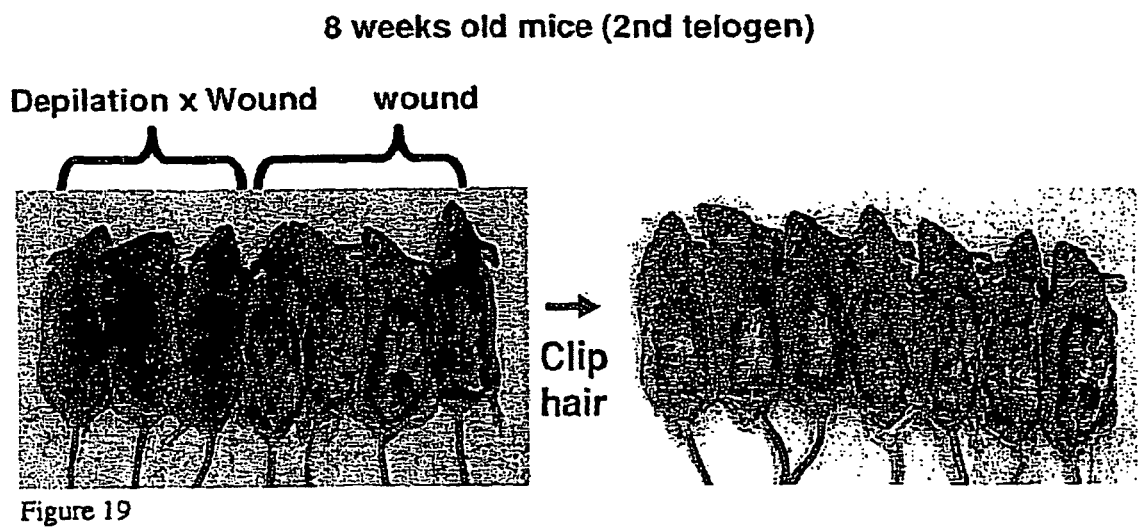
FIG. 19. Wounds closed similar in mice subjected to depilation, then wounding (left 3 mice in each panel) vs. wounding alone (right 4 mice in each panel). Left panel: immediately following wounding. Right panel: 10 days following wounding.
Figure 20:
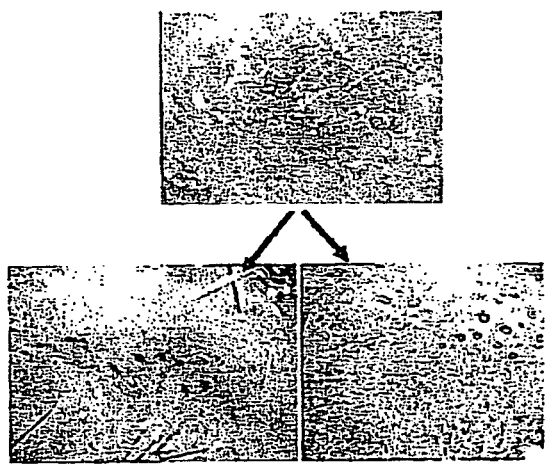
FIG. 20. Anagen induction by depilation prior to wounding enhances the efficiency of EDIHN.
Figure 20:
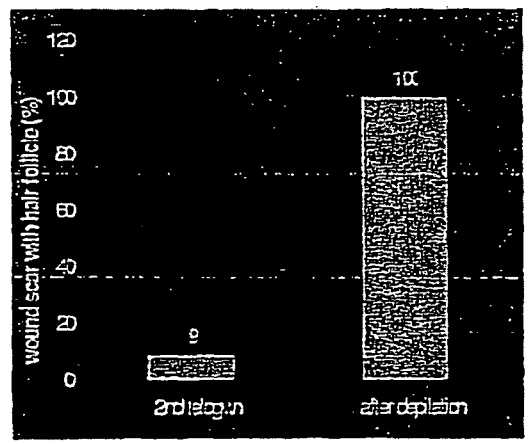

To determine whether experimental induction of anagen increased the efficiency of EDIHN, 8-week-old mice were depilated several days prior to wound induction. As depicted in FIG. 19, the wounds closed similarly whether or not they were preceded by depilation. As depicted in FIG. 20A-B, the depilated mice exhibited enhanced EDIHN relative to the non-depilated mice depicted in the previous Example by a factor of 11-fold.

The findings of this Example demonstrate that anagen induction enhances EDIHN. In addition, these findings show that EDIHN is capable of not only forming new HF, but also of activating anagen in pre-existing HF in the telogen stage.

Example 7

EDIHN Induces New Hair Follicles in Human Skin

Grafting. Discarded human adult scalp from the preauricular area obtained from plastic surgery was grafted onto immunodeficient (scid) mice. The graft was bandaged and allowed to heal, then was used in the wound healing study 3 months after grafting.

Figure 21A:
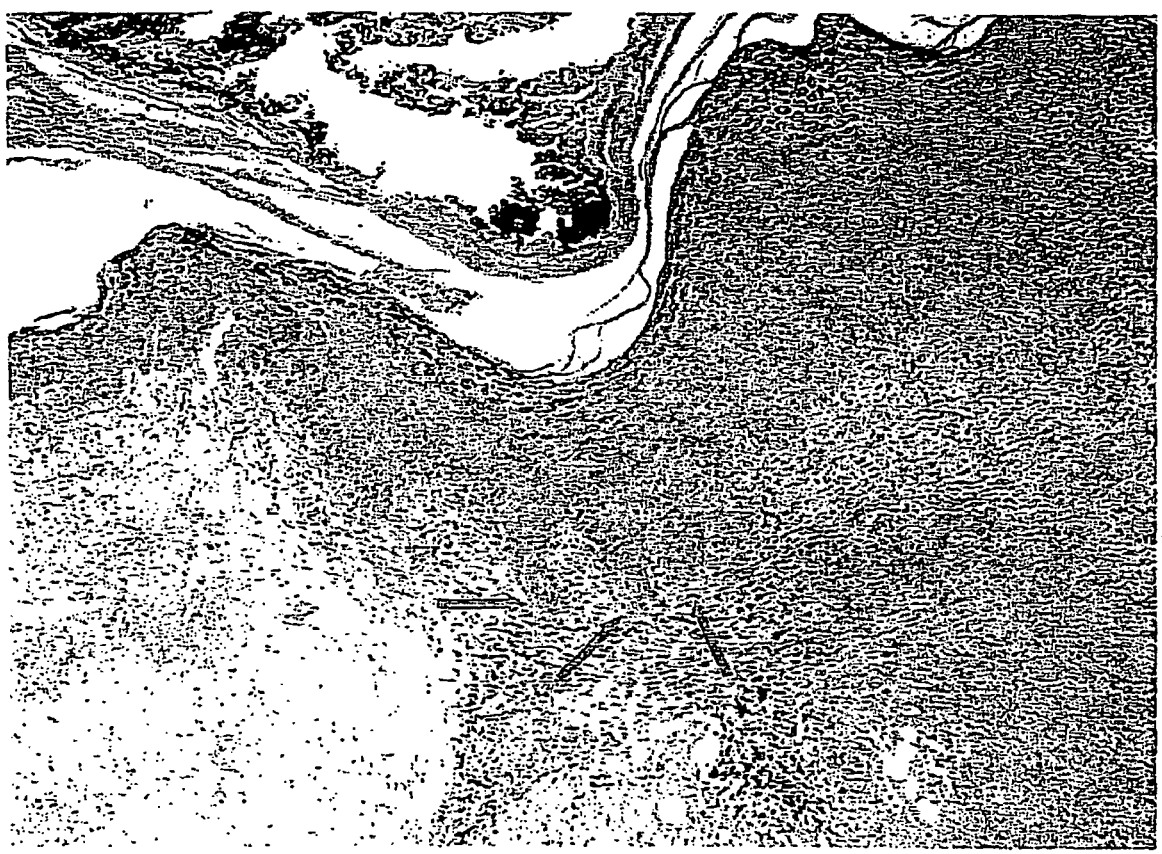
FIG. 21A. EDIHN in human skin grafted to immunodeficient (scid) mice, seven days after induction of an excisional wound. Arrows indicate new HF.

Results: To determine whether human skin responded to EDIHN as did mouse skin, human skin was grafted onto SCID (immuno-deficient) mice and subjected to depilation by plucking and wound induction three days later. Seven days following wound induction, formation of new HF was observed in the human skin (FIG. 21A; arrows indicate new HF) by hematoxylin and eosin staining of paraffin embedded tissue sections.

Figure 21B:
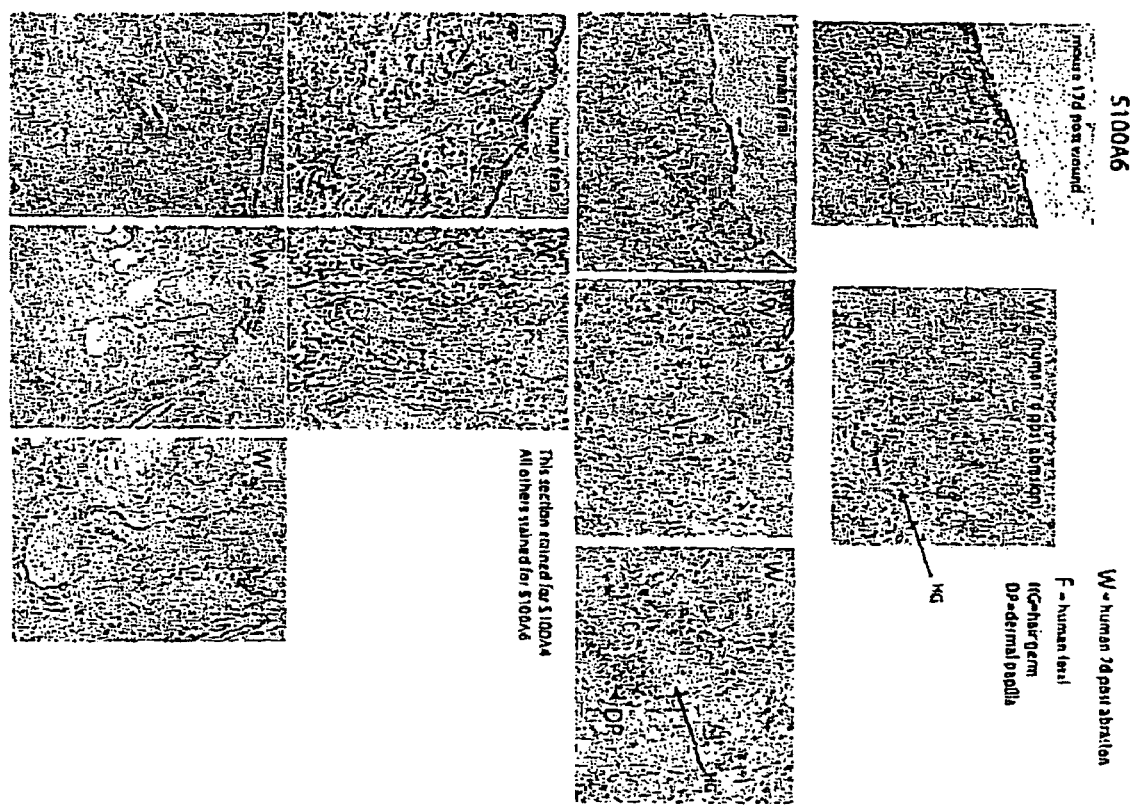
FIG. 21B. Dermal abrasion of human skin grafts results in EDIHN. Human adult skin (W) was grafted onto mice, abraded, and examined seven days later, by staining for S100A6 (first, second, and fourth rows) or S100A4 (third row). Hair germs (HG) and dermal papilla (DP) are indicated. Human fetal skin (F) with normal developing hair follicles is shown for comparison. Mouse skin 17d post wounding was included as a control (top left panel).

In additional experiments, adult human skin was grafted onto mice, abraded, and examined at 7 days post-abrasion. New HF were generated in the human skin, which mimicked normal hair follicle formation during fetal development, as evidenced by staining for S100A6 or S100A4 (FIG. 21B).

The results of this Example show that EDIHN can be used to generate hair growth in human skin as for mouse skin.

Example 8

Molecular Pathways Activated During HF Stem Cell Activation

Isolation and activation of HF stem cells. K15-eGFP mice were depilated in order to induce formation of new HF. Activated hair follicle stem cells were isolated from K15-eGFP mice using fluorescence-activated cell sorting (FACS) two days after depilation and 5 mg (micrograms) total RNA from the cell population was isolated, reverse-transcribed and hybridized to an Affymetrix (Santa Clara, Calif.) array MG_U74v2 chip. Scanned chip images were analyzed using Affymetrix Microarray Suite 5.0 and GeneSpring software (Silicon Genetics) to detect fold-change differences between activated HF stem cells (HFSCs) and non-activated (telogen) HFSCs. Values were normalized before computing fold-changes and differences between non-activated "bs-line" and activated ("expt") samples.

Results: To identify molecular pathways up-regulated during HF stem cell activation, activated HF stem cells were isolated, and the gene expression patterns of the cells were analyzed to detect up-regulated transcripts. The transcripts (Accession Nos. AW047343, AF053235, M26005, AA681998, AF057156, AI845584, AA614971, AV374591, U04443, Y07836, M21285, V00756, Y14296, X16490, AW120868, C78850, D67076, M61007, C85523, AW122030, U57524, U05809, AW212475, V00835, AV374868, M21285, U74683, X61800, U20735, U19118, AW049031, M93275, AB000713, U20735, U83148, L10244, U88328, X82786, AW122523, AI642048, L07264, M15668, AI047508, AJ001418, AI838080, AF072127, X80417, AI847051, U09504, U22033, AF033034, AA960603, U47737, L00039, D21099, AF026481, J04596, X81580, AI314958, AF058798, AW046627, AI848050, AF065441, AF022992, AF064088, AI787713, AI853531, X14678, AI854358, X67668, K02236, X51829, AW048937, AV139913, M32490, AI121305, U35374, X15643, AI849109, U70132, M13805, AV138783, K02927, X07699, X57800, M35247, AI553024, X16995, AF038562, Y11666; U40930, D26090; AI787627, M33988, AI845182, AA619207, AW125783, J04103, D90146, AI563854, AF017128, X67644, AA980204, AI843232, U59807, AI152659, AI850090, AF064635, AI843106, AF033186, Z50159, X78683, X68193, AA062013, AI465965, U50413, AW120502, X62940, U60020, L32752, AI840013, AB020424, AI848453, AU040563, X89749, AW125390, X05862, AW046181, U10118, AW212775, AI846302, M22998, X64837, AI843119, AI837786, U41465, U70494, D17666, X14897, AJ006289, X12944, AW061302, U67328, AI604314, AI845121, AW047756, AI838021, AW122893, M59821, M13805, AI845886, X53157, U19118, AF062071, U10404, U07634, X04663, X61232, X14309, U42386, U51126, AF093853, Z19521, U04354, M35244, AW121930, AI852632, U70475, U09659, AW124785, AF071315, D49733, X80899, D83203, Z20410, A1839906, AI843448, AW125336, AW123802, AI835771, X53584, M32599, AF035644, Y00629, AW125380, U68564, AW125346, X61232, D20333, AB025218, U84411, M62362, AA032310, M94087, AI847609, AI853294, M33934, X16202, A1661431, AI839109, AI849135, M32459, AI841389, X03039, AW049795, D87691, AI117211, Y00520, AA638002, Z22661, X99644, AI843895, M38724, AW122989, AI844810, AA940430, M38381, AF014371, Z30939, U28208, and AV218217) were up-regulated at least 2-fold in the activated HF stem cells relative to the cells prior to activation. In some cases, the sequence is a genomic sequence that contains the sequence of the transcript. Data pertaining to the up-regulation of the transcripts and further information about them is provided in FIG. 22.

Thus, the transcripts identified in this Example, the proteins they encode, and the pathways in which the proteins participate, contribute significantly to induction of epidermal cells to differentiate into HF stem cells. Activation of the transcripts, proteins, and pathways depicted in Table 4 is thus a method for enhancing EDIHN. In addition, inhibition of the transcripts, proteins, and pathways depicted in Table 4 is thus a method for preventing EDIHN and eliminating hair follicles. In addition, inhibition of the transcripts, proteins, and pathways depicted in Table 5 is a method for enhancing EDIHN. In addition, activation of the transcripts, proteins, and pathways depicted in Table 5 is thus a method for enhancing EDIHN.

Example 9

Molecular Pathways Activated During Induction of Epidermal Cells to Differentiate into HF Stem Cells The gene expression pattern of HF stem cells was analyzed as described in Example 8 and compared to non-bulge basal keratinocytes. 157 genes were differentially expressed in the HF stem cells, as assessed by microarray analysis and quantitative polymerase chain reaction (qPCR). A group of selected genes with increased expression in HF stem cells is depicted in Table 4. A group of selected genes with decreased expression in HF stem cells is depicted in Table 5.

TABLE 4

Genes up-regulated in HF stem cells.

| Gene Name/Protein name | GenBk Acces #. | | Fold Incr. |
|---|---|---|---|
| Cd34/Cd 34 antigen | AI847784, AI173145 | Cell surface proteins | 43 (189) |
| S100a4/ S100A4 (mts) | X15986 | Calcium-related | 35 (144) |
| Id2 helix-loop-helix protein | AF077861 | Transcription Factors and related genes | 11 (25) |
| Id4 | AJ001972 | Transcription Factors and related genes | 4 (12) |
| Peg3/ Paternally expressed gene 3 zinc finger protein | AF038939 | Transcription Factors and related genes | 12 |
| Fz2/ Frizzled 2 | AW123618 | Growth Factors, Receptors and Related genes | 9 (17) |
| Dkk3/ Dickkopf3 | AJ243964 | Growth Factors, Receptors and Related genes | 6 (22) |
| Sfrp1/ Secreted frizzled-related protein 1 | U88566 | Growth Factors, Receptors and Related genes | 6 |
| Dab2/ Disabled homolog 2 | U18869 | Growth Factors, Receptors and Related genes | 15 |
| Cktsf1b1/ Gremlin, Cysteine knot superfamily 1, BMP antagonist 1 | AF045801 | Growth Factors, Receptors and Related genes | 12 (12) |
| Fgfr1/ Fibroblast growth factor receptor 1 | U22324 | Growth Factors, Receptors and Related genes | 10 |
| Fgf1/ Fibroblast growth factor 1 | M30641 | Growth Factors, Receptors and Related genes | 10 |
| Gpr49/ G protein-coupled receptor 49 FEX | AF110818 | Growth Factors, Receptors and Related genes | 64 (377) |
| Igfbp5/ insulin-like growth factor binding protein 5 | L12447 | Growth Factors, Receptors and Related genes | 37 |
| Myoc/ trabecular meshwork induced gluco-corticoid protein | AF041335 | Growth Factors, Receptors and Related genes | 111 |
| Itm2a/E25 putative Integral membrane protein 2A | L38971 | Growth Factors, Receptors and Related genes | 30 |
| Eps8/ epidermal growth factor receptor pathway substrate 8 | L21671 | Growth Factors, Receptors and Related genes | 15 |
| Fyn/Fyn proto-oncogene | M27266 | Growth Factors, Receptors and Related genes | 10 |
| Col6a1/ Procol-lagen, type VI, alpha 1 | X66405 | Structurally-related | 36 |
| Tnc/ Tenascin C | AV230686 X56304 | Structurally-related | 17 |
| Krt2-6a/Keratin complex 2, basic, gene 6a (keratin 6a) | K02108 | Structurally-related | 10 |
| Potassium channel, subfamily K, member 2 | AI849601 | Channel-related | 14 |
| Skd3/ Suppressor of K+ transport defect 3 | AI837887 | Channel-related | 4 |
| Clic4/ Chloride intracellular channel 4 (mito-chondrial) | AI845237 | Channel-related | 3 |
| Col18a1/ Endostatin (alpha 1(XVIII) collagen) | L22545 | Channel-related | 5 |

Numbers in parentheses are the fold increase as determined by quantitative real time PCR.

TABLE 5

Genes down-regulated in HF stem cells.

| Gene Name/Protein name | GenBk Acces #. | | Fold Incr. |
|---|---|---|---|
| GNA-14 Mouse G protein alpha subunit (GNA-14) | M80631 | Growth Factors, Receptors and Downstream genes | 32 |
| Ly6/Lympho-cyte antigen 6 complex | X04653 | Growth Factors, Receptors and Downstream genes | 12 |
| Bmp4/Bone morphogenetic protein 4 | L47480 | Growth Factors, Receptors and Downstream genes | 11 |
| IL1r2/Inter-leukin 1 receptor, type II | AV223216 X59769 | Growth Factors, Receptors and Downstream genes | 11 |
| Wnt3a/wing-less-related MMTV integration site 3A | X56842 | Growth Factors, Receptors and Downstream genes | 4 |
| Il12rb2/ Interleukin 12 receptor, beta 2 | U64199 | Growth Factors, Receptors and Downstream genes | 3 |
| Wnt10a/Wing-less-related MMTV integration site 10a | U61969 | Growth Factors, Receptors and Downstream genes | 3 |
| Ifngr2/Inter-feron-gamma receptor precursor | M28233 | Growth Factors, Receptors and Downstream genes | 3 |
| Fgfbp1/ Fibroblast growth factor binding protein 1 | AF065441 | Growth Factors, Receptors and Downstream genes | 3 |
| Klf5/Kruppel-like factor 5 | AA611766 | Transcription Factors and Related Genes | 5 |
| Gata3/GATA binding protein 3 | X55123 | Transcription Factors and Related Genes | 4 |
| Stimulated by retinoic acid 14, basic-helix-loop-helix protein | Y07836 | Transcription Factors and Related Genes | 3 |
| Mki67/antigen identified by monoclonal antibody Ki67 | X82786 | Cell Cycle Related | 4 |
| Cks2/CDC28 protein kinase regulatory subunit 2, sim to cdk regulatory subunit 2 | AA681998 | Cell Cycle Related | 4 |
| Ccng2/ Cyclin G2 | U95826 | Cell Cycle Related | 3 |
| Prc1/Protein regulator of cytokinesis 1 DNA segment, Chr 7 | AA856349 | Cell Cycle Related | 3 |

Thus, the transcripts identified in this Example, the proteins they encode, and the pathways in which the proteins participate, contribute significantly to induction of epidermal cells to differentiate into HF stem cells. Activation of the transcripts, proteins, and pathways depicted in Table 4 is thus a method for enhancing EDIHN. In addition, inhibition of the transcripts, proteins, and pathways depicted in Table 4 is thus a method for preventing EDIHN and eliminating hair follicles. In addition, inhibition of the transcripts, proteins, and pathways depicted in Table 5 is a method for enhancing EDIHN. In addition, activation of the transcripts, proteins, and pathways depicted in Table 5 is thus a method for enhancing EDIHN.

Example 10

Expression of WNT-1 Inhibitors During the First Nine Days After Wounding Causes Pigmentation of New HF In this Example, doubly transgenic mice expressing both tetO-Dkk1 and K5-rtTA were utilized. When these mice are fed chow formulated with 1 g/kg doxycycline (BioServ, Laurel, Md.), they express Dkk1, under the control of the K5 promoter, in the basal epidermis. The control mice also received doxycycline, but they were K5-rtTA negative and thus did not express Dkk1.

Figure 23A:
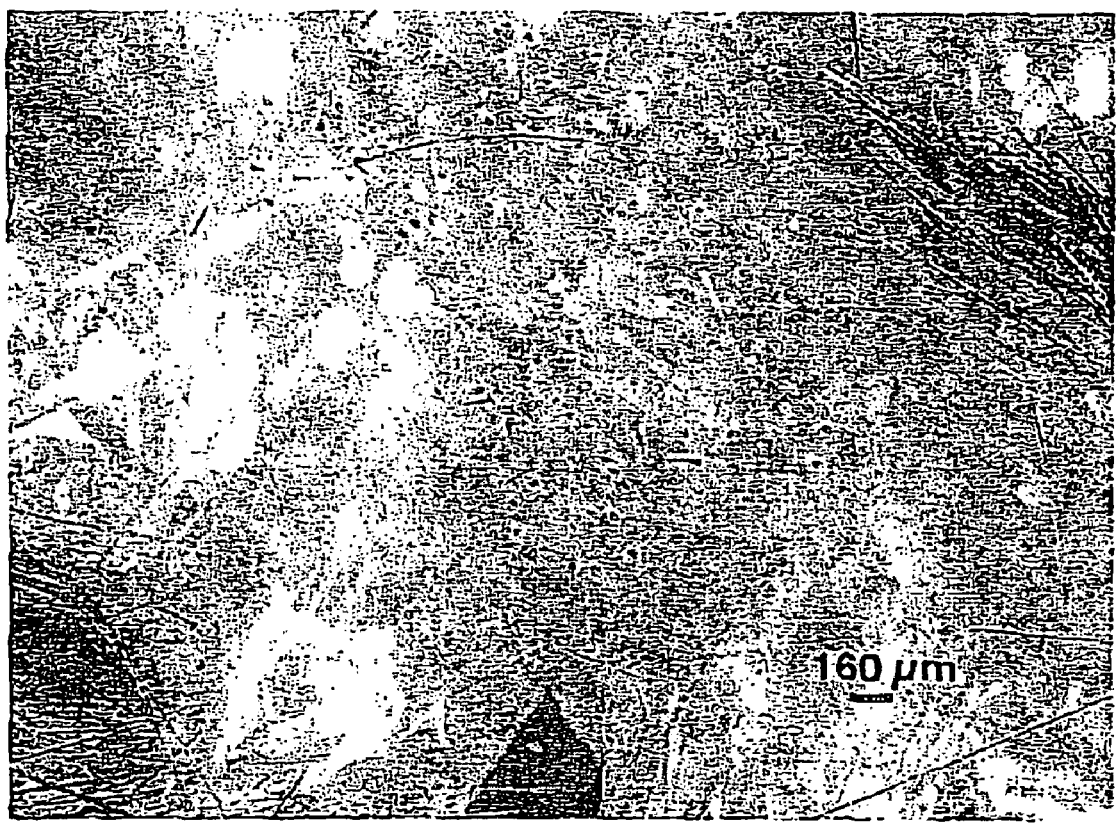
FIG. 23A. 3.2× magnification.
Figure 23B:
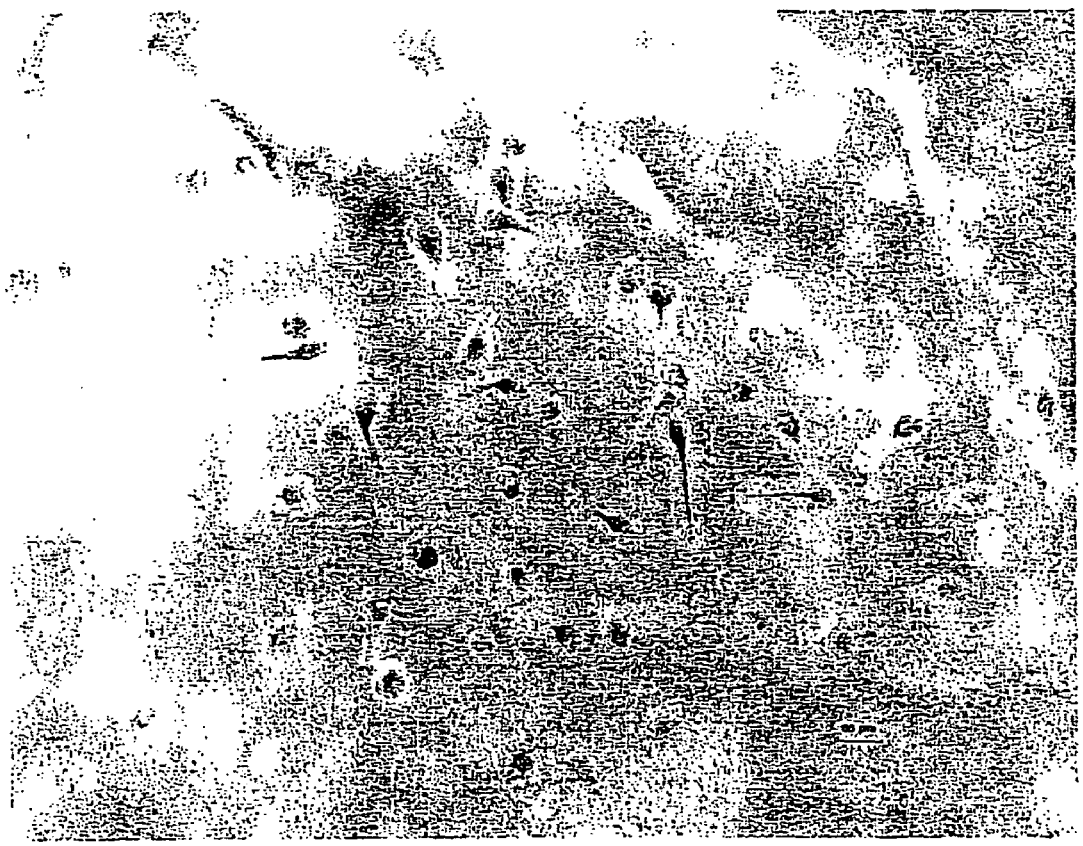
FIG. 23B. 8× magnification.
Figure 24:
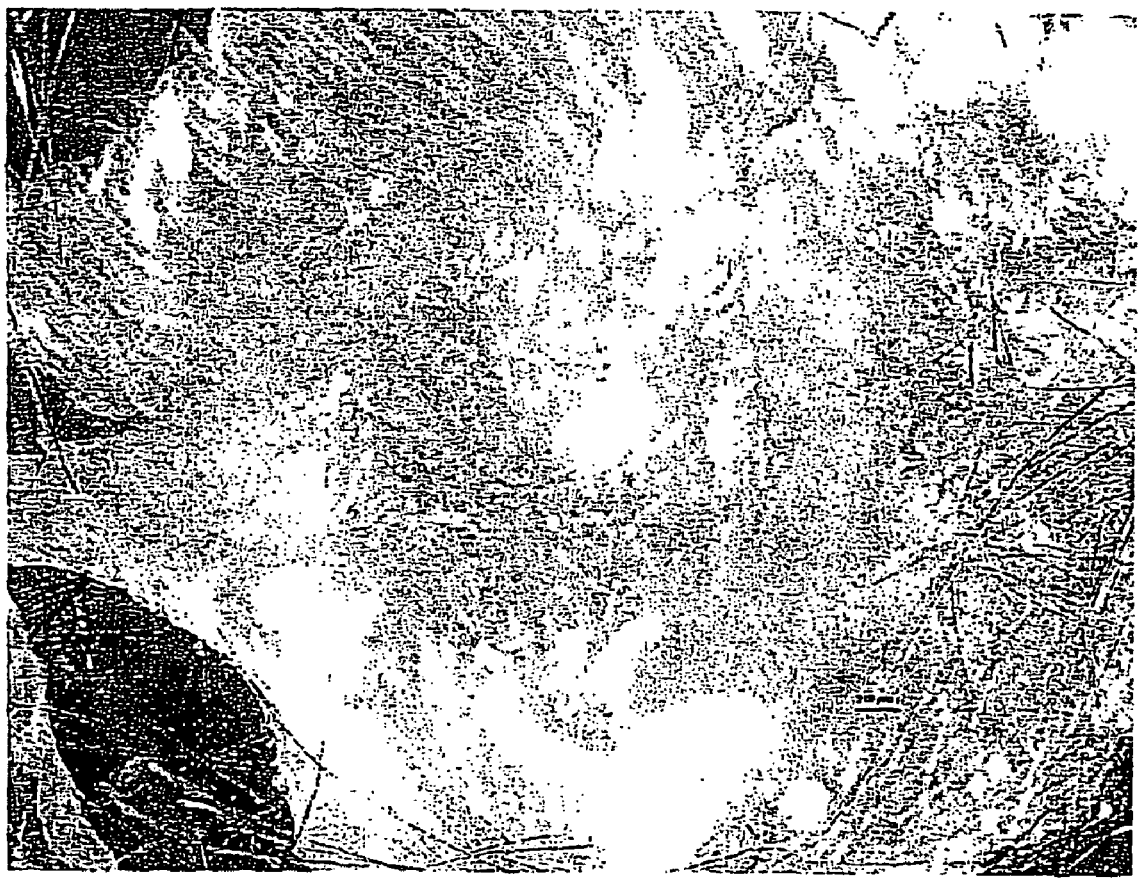
FIG. 24. Control mice lacked pigmented HF.
Figure 25A:
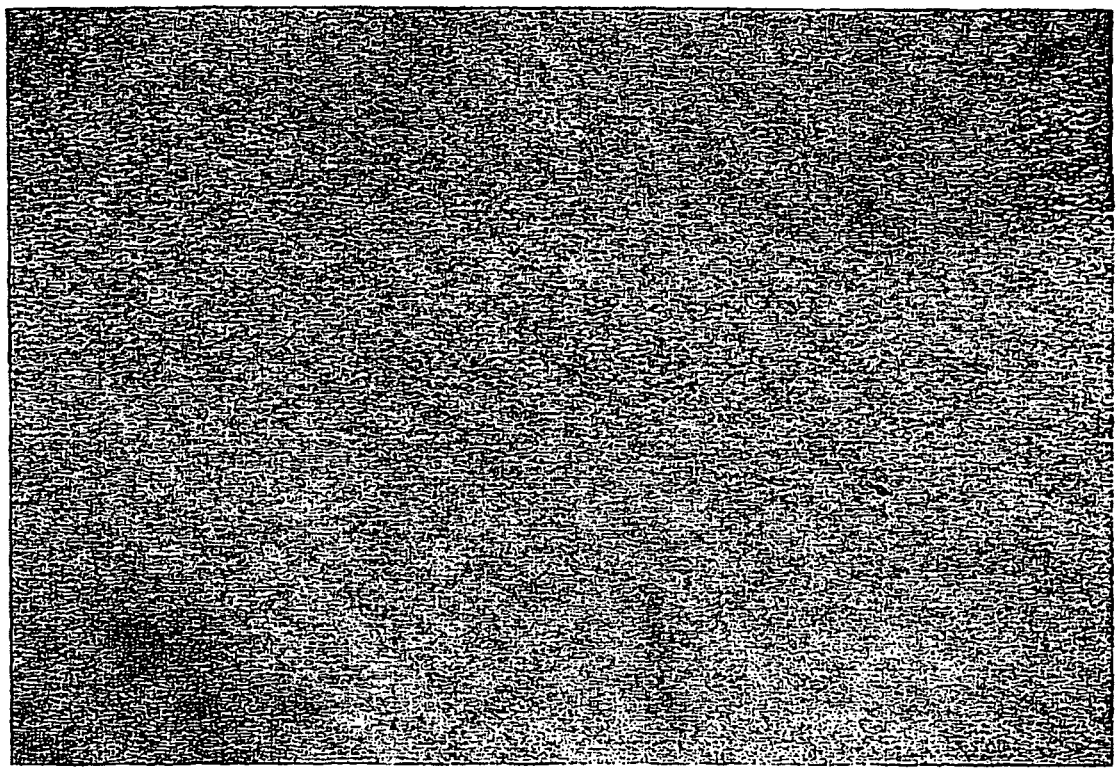
FIG. 25A. K17 staining of wounded skin of representative mouse treated with EGF. Magnification is 4×.
Figure 25B:
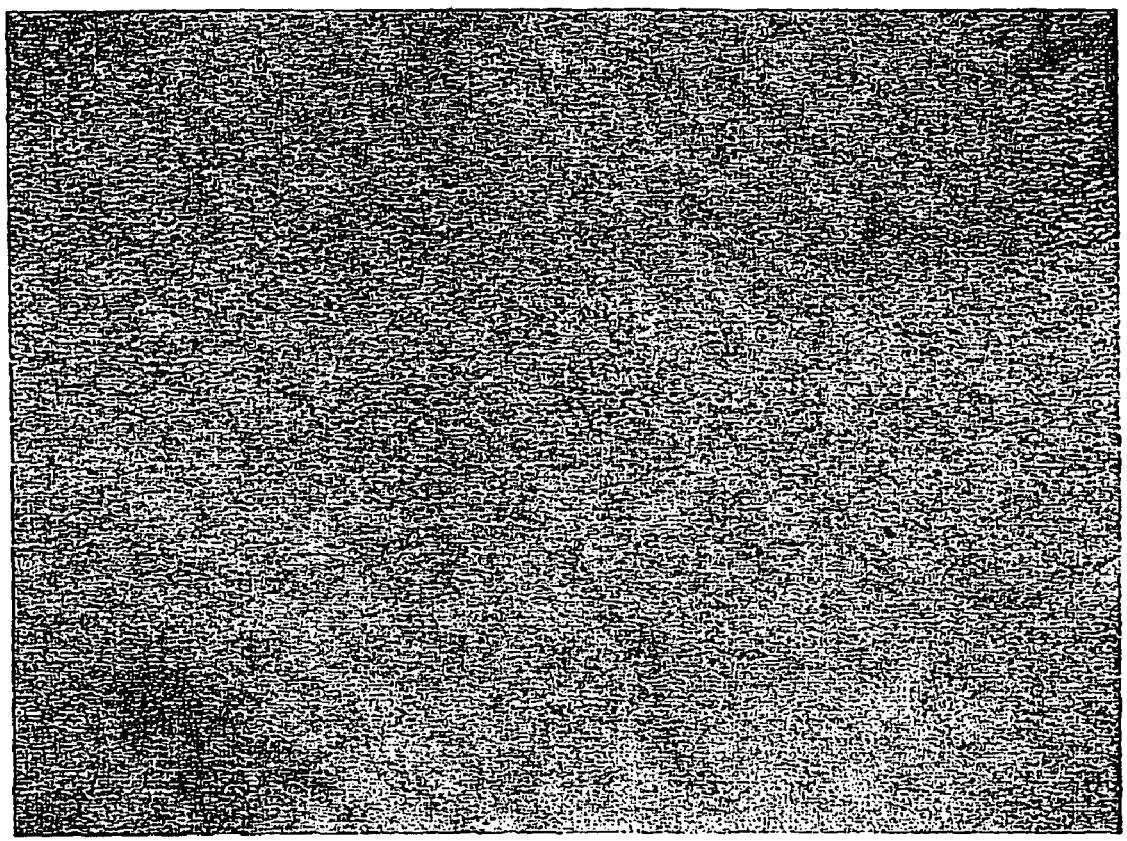
FIG. 25B. High magnification view (10×) of skin depicted in (A).
Figure 25C:
FIG. 25C. K17 staining of wounded skin of representative control mouse that received no EGF after wounding. Magnification is 4×.
Figure 25D:
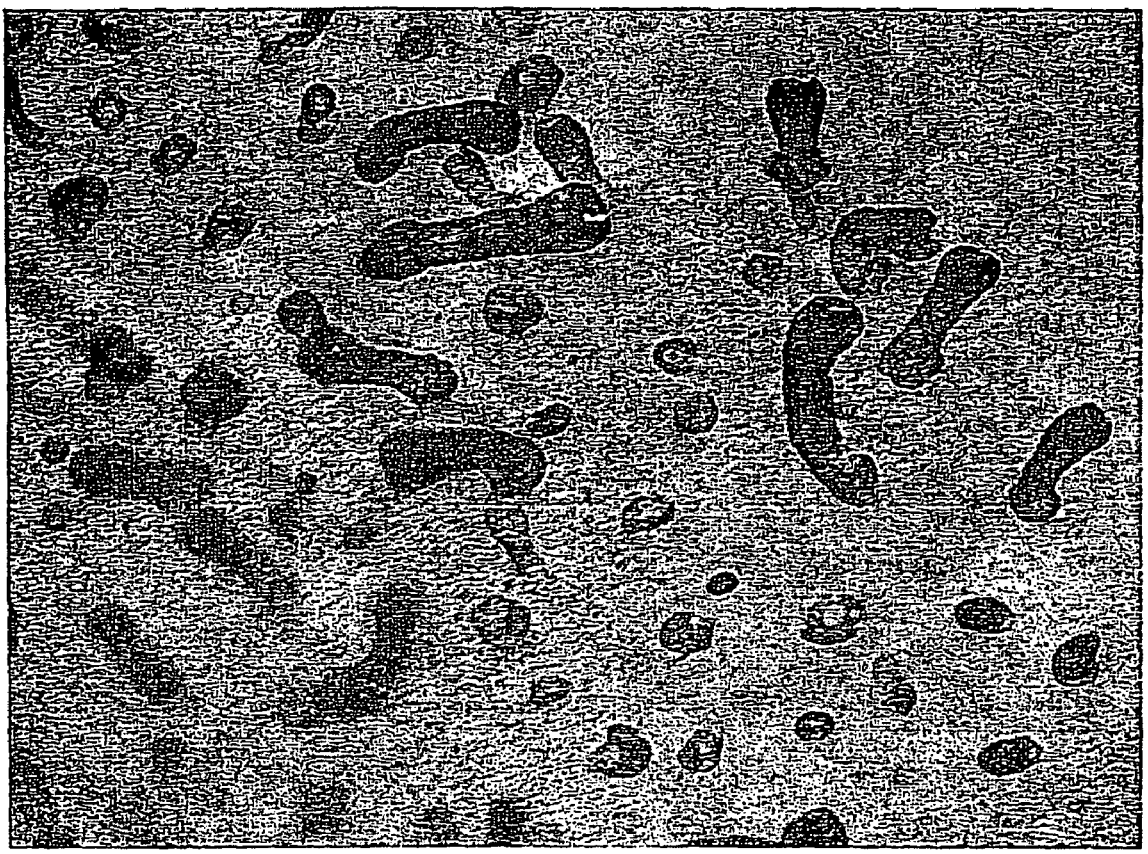
FIG. 25D. Higher magnification view (10×) of skin depicted in (D).

Results: A 1 cm2 wound was induced on the lower back of the doubly transgenic mice at 21 days or 50 days old. Mice were placed on doxycycline-containing chow immediately after wounding to induce Dkk1 expression, and then doxycycline was discontinued after completion of the re-epithelialization at 9 days after wounding. Dkk1 expression inhibits Wnt activity, which in turn induces follicle pigmentation. At 22 days after wounding, pigmented HF were observed in the excised skin after preparing the epidermal sheet (FIG. 23A-B). Control mice lacked pigmented HF (FIG. 24).

In other experiments, continued expression of Dkk1 after the 9-day period inhibited formation of new HF.

The findings of this Example show that pigmented HF can be produced by suppressing expression of Wnt1 or by inducing expression of Dkk1 during the period of re-epithelialization, then inducing expression of Wnt1. In addition, the findings of this Example show that factors that inhibit neonatal hair follicle formation (e.g., Dkk1) also inhibit EDIHN, thus further supporting the notion that hair follicles formed by EDIHN are similar to normal hair follicles.

Example 11

Inhibition of EDIHN by Epidermal Growth Factor Injection 21 day-old mice were wounded as described in previous Examples. Starting from day 11 after wounding, a time point corresponding to the point at which the wound had recently re-epithelialized, 10 mL of 1 mg/ml EGF was injected into the wound bed. EGF was injected once per day after this point for a total of 5 days. Three days later, the skin was collected, and whole-mount EDIHN assays were performed. EGF prevented HF formation as assessed by gross morphology. In addition, whole mounts of control and treated skin were analyzed with anti-K17 antibody immunostaining. All mice injected with EGF (n=4) exhibited no new HF formation (FIGS. 25 A-B), while control mice (n=2) had many new HF, as expected. (FIGS. 25 C-D).

In an additional experiment, recombinant EGF (1 microgram (mcg)/microliter (mcl)) was injected at days 11, 13 and 15 after wounding. Skin was collected at 18 days after wounding and stained for K17 and alkaline phosphotase. Once again, administration of EGF inhibited EDIHN.

The findings of this Example show that EGF inhibits HF formation. Thus, inhibiting EGF, EGFR, or one of the pathways in which they participate increases EDIHN-induced HF formation.

Example 12

Enhancement of EDIHN by Inhibition of EGF Receptor

Figure 26A:
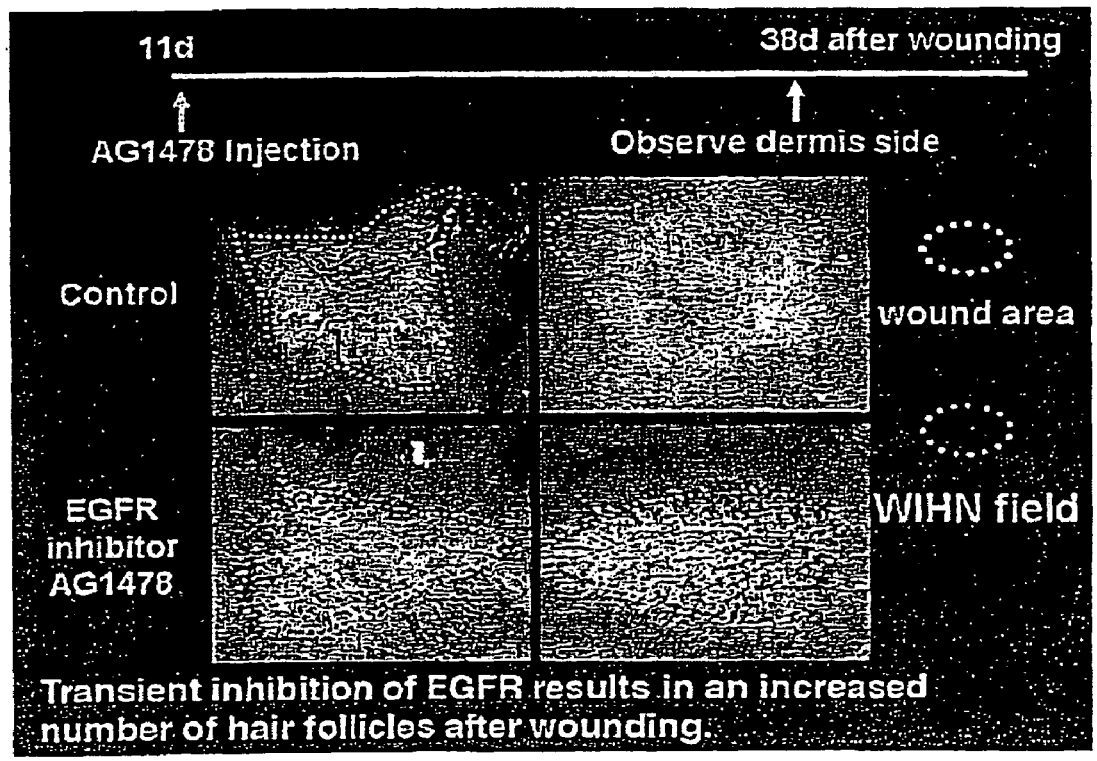
FIG. 26A. Top: skin of 2 control mice. Outer dashed line indicates the extent of the wounded area after contraction and healing; inner dashed line indicates the area of neogenesis. Bottom: skin of 2 treated mice, in which the wounded area and area of neogenesis largely coincide, with the exception of a small area on the left side of the encircled area in each panel.
Figure 26B:
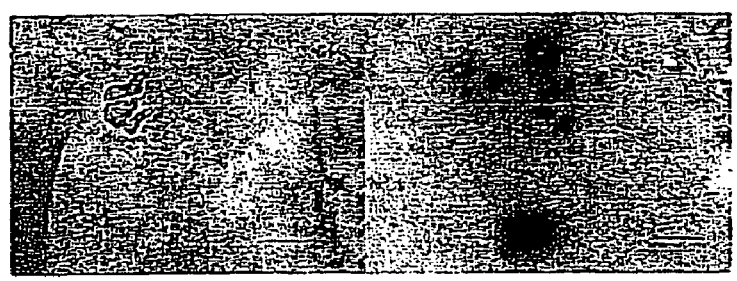
FIG. 26B. Large hair follicles developed in the wounded area in the AG1478-injected mice. Left panel: epidermis stained for K17, with three large hair follicles next to each other. Right panel: dermis stained for AP with large coalescing DP areas. Scale Bars: 200 μm.

To determine the effect of administration of EGF receptor inhibitors on DIHN, the inhibitor AG1478 (150 μM in 10 μL volume) was administered as a single injection 11 days after incisional wounding (1 cm2) to the middle of the wound near the skin surface. EGF receptor inhibitor administration led to generation of more and larger hair follicles compared with control mice that were wounded only (FIG. 26A). As shown in FIG. 26B, large hair follicles developed in the wounded area in the AG1478-injected mice. Left panel: epidermis stained for K17, with three large hair follicles next to each other. Right panel: dermis stained for AP with large coalescing dermal papilla areas.

The findings of this Example confirm the results of the previous Example, and show that more and larger HF can be generated when EDIHN comprises, or is followed by, administration of EGFR inhibitors, or with compounds with a similar mechanism of action; e.g., Hedgehog protein and androgen antagonists.

Example 13

Enhancement of EDIHN by Expression of a β-Catenin Activator

Figure 27A:
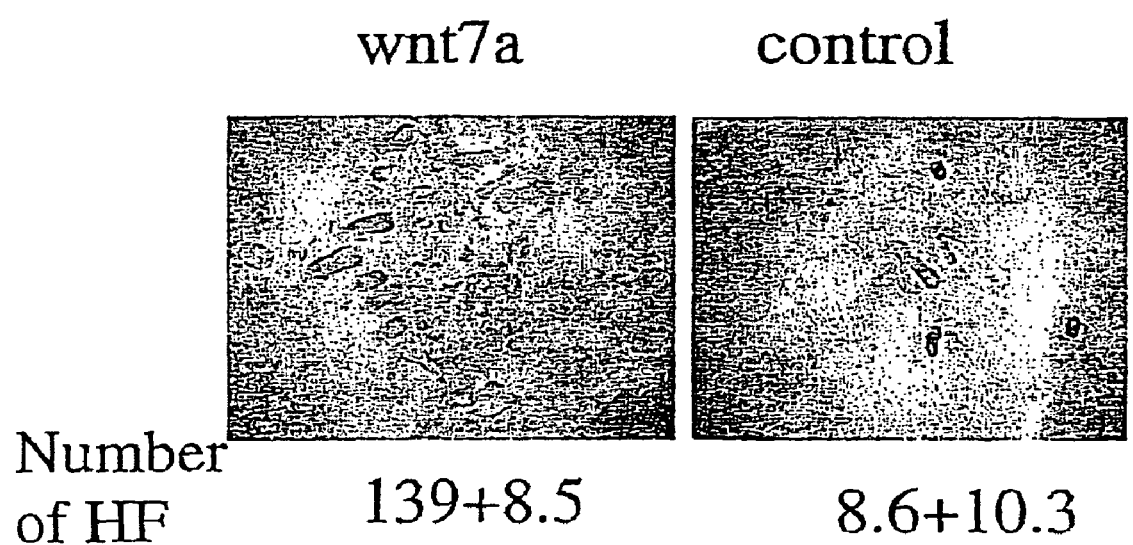
FIG. 27A. Increased hair follicle formation in K14-Wnt7a mice. Left panel: Wnt7a transgenic mice. Right panel: control (wild-type) mice.
Figure 27B:
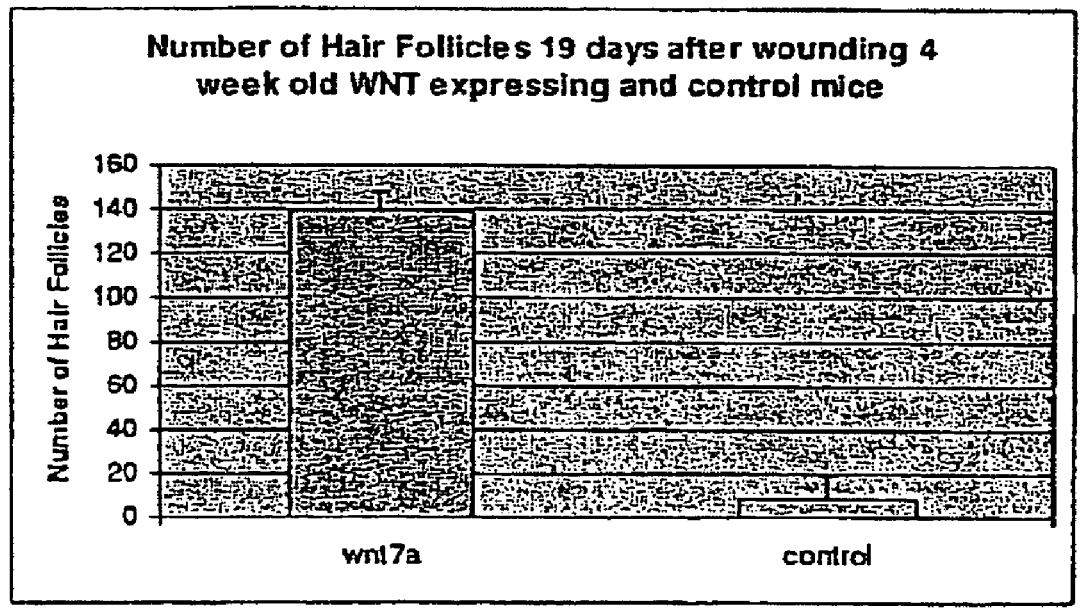
FIG. 27B. Quantiation of experiment with 4 week old mice.
Figure 27C:
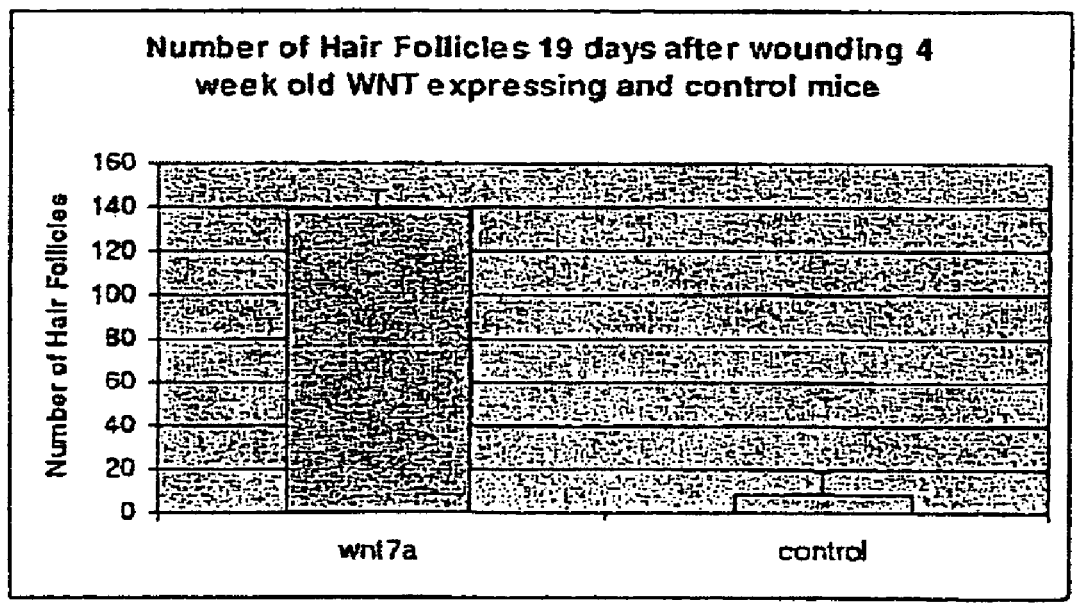
FIG. 27C. Quantiation of experiment with 3 week old mice.

To determine the effect of administration of β-catenin activators on EDIHN, K14-Wnt7 transgenic mice, which overexpress the β-catenin pathway activator, Wnt7, in the epidermis, were subjected to EDIHN, then HF formation was measured 19 days after wounding. In each of 2 separate experiments, with 4 week old and 3 week old mice, the transgenic mice developed significantly larger numbers of HF compared to control, non-transgenic littermate mice (FIG. 27 A-C).

Thus, administration of β-catenin activators leads to an increase in EDIHN. The findings of Examples 11-13 show that new HF can be generated by (a) disrupting the epidermis; and (b) administering a factor that promotes a differentiation of an uncommitted epidermal cell into a HF cell.

Example 14

Enhancement of EDIHN by Administration of FGF

To determine the effect of fibroblast growth factor (FGF) on EDIHN, recombinant FGF is administered 11 days after incisional wounding, as described in Example 11. FGF administration enhances HF formation, showing that new HF can be generated by (a) disrupting the epidermis; and (b) administering FGF, a nucleotide encoding FGF, or a factor that increases signaling by FGF.

Example 15

Enhancement of EDIHN by Administration of EDAR

To determine the effect of fibroblast growth factor (FGF) on EDIHN, K14-Eda-A1 transgenic mice, which overexpress (ectodysplasin-A1) Eda-A1 in the epidermis, are subjected to EDIHN, then HF formation is measured 19 days after wounding as described in Example 13. The transgenic mice develop significantly larger numbers of HF compared to control, non-transgenic littermate mice, showing that new HF can be generated by (a) disrupting the epidermis; and (b) administering a factor that enhances signaling by ectodysplasin.

Example 16

Enhancement of EDIHN by Administration of Minoxidil

To determine the effect of minoxidil on EDIHN, recombinant FGF is administered 11 days after incisional wounding, as described in Example 11. Minoxidil administration enhances HF formation, showing that new HF can be generated by (a) disrupting the epidermis; and (b) administering a minoxidil.

Example 17

Removal of HF by Abrasion and Administration of EGF

Hair-bearing regions of the epidermis of mice is abraded, as described in Example 1, then administering recombinant EGF, as described in Example 1. This method prevents hair re-growth in the abraded areas, showing that hair can be removed by (a) disrupting the epidermal layer; and (b) administering EGF, a nucleotide encoding EGF, or a factor that increases signaling by EGF.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method for stimulating a hair growth on the skin of a subject, said method comprising the steps of:

(a) inducing reepithelialization of the skin of said subject; and
(b) contacting the cells of said skin with a composition comprising from 0.001% to 0.1% (w/v) of a compound selected from the group consisting of: leflunomide, gefitinib, erlotinib, lapatinib, canertinib, vandetanib, CL-387785, PKI166, pelitinib, HKI-272, HKI-357, and the leflunomide metabolite A771726 in an amount sufficient to generate hair follicles or stimulate hair growth on said skin.

2. The method of claim 1, wherein step (a) is performed less than two weeks prior to step (b).

3. The method of claim 1, wherein said small molecule EGFR inhibitor is gefitinib.

4. The method of claim 1, wherein said small molecule EGFR inhibitor is erlotinib.

5. The method of claim 1, wherein said small molecule EGFR inhibitor is leflunomide.

6. The method of claim 1, wherein said small molecule EGFR inhibitor is the leflunomide metabolite A771726.

7. The method of claim 1, wherein said skin is the skin of the subject's scalp or eyebrow.

8. The method of claim 1, wherein said subject suffers from balding of the scalp.

9. The method of claim 1, wherein said contacting is performed during the night.

10. The method of claim 1, wherein said contacting is performed during the day.

11. The method of claim 1, wherein said subject suffers from androgenetic alopecia.

12. The method of claim 1, wherein said subject suffers from discoid lupus erythematosis.

13. The method of claim 1, wherein said subject suffers from congenital hypotrichosis.

14. The method of claim 1, wherein said subject suffers from lichen planopilaris.

15. The method of claim 1, wherein said subject suffers from scarring alopecia.

16. The method of claim 1, further comprising the step of administering to said subject an additional biologically active agent selected from an antihistamine, an anti-inflammatory, a retinoid, an anti-androgen, an immunosuppressant, a channel opener, an antibiotic, and an antimicrobial.

17. The method of claim 1, wherein said small molecule EGFR inhibitor is administered to said subject once or twice daily.

* * * * *